US008993515B2

(12) United States Patent
Lubell et al.

(10) Patent No.: US 8,993,515 B2
(45) Date of Patent: Mar. 31, 2015

(54) PEPTIDOMIMETICS COMPRISING N-AMINO CYCLIC UREA RESIDUES AND USES THEREOF

(71) Applicants: Valorisation-Recherche, Limited Partnership, Montreal (CA); RSEM, Limited Partnership, Montreal (CA)

(72) Inventors: William D. Lubell, Montreal (CA); Sylvain Chemtob, Cote-St-Luc (CA); Huy Ong, Mont-Royal (CA); Robert Hopewell, Montreal (CA); Caroline Proulx, Richmond Hill (CA); Kim Beauregard, Boucherville (CA); Yesica Garcia-Ramos, Barcelona (ES); Ngoc-Duc Doan, Montreal (CA)

(73) Assignees: Valorisation-Recherche, Limited Partnership, Montreal (CA); RSEM, Limited Partnership, Montreal (CA)

( * ) Notice: Subject to any disclaimer, the term of this patent is extended or adjusted under 35 U.S.C. 154(b) by 0 days.

(21) Appl. No.: 13/910,647

(22) Filed: Jun. 5, 2013

(65) Prior Publication Data
US 2014/0024606 A1 Jan. 23, 2014

Related U.S. Application Data

(60) Provisional application No. 61/655,682, filed on Jun. 5, 2012.

(30) Foreign Application Priority Data

Jun. 5, 2012 (CA) ..................... 2779949

(51) Int. Cl.
*A61K 38/27* (2006.01)
*C07K 7/06* (2006.01)
*C07K 7/00* (2006.01)
*A61K 38/00* (2006.01)

(52) U.S. Cl.
CPC ...... *C07K 7/06* (2013.01); *C07K 7/00* (2013.01); *A61K 38/00* (2013.01)
USPC .......................................... 514/5.1

(58) Field of Classification Search
None
See application file for complete search history.

(56) References Cited

PUBLICATIONS

Andrée et al.—Aza-peptides II. X-ray structures of aza-alanine and aza-asparagine-containing peptides. J. Pept. Res. 1997, 49(6), pp. 556-562.
Andre et al.—Aza-peptides. III. Experimental structural analysis of aza-alanine and aza-asparagine-containing peptides. J. Pept. Res. 1997, 50(5), pp. 372-381.
Armarego et al.—Purification of Laboratory Chemicals. Butterworth-Heinemann, 1996, p. 381.
Austin et al.—A template for stabilization of a peptide α-Helix: synthesis and evaluation of conformational effects by circular dichroism and NMR. J. Am. Chem. Soc. 1997, 119, pp. 6461-6472.
Ball et al.—Conformationla constraints: nonpeptide β-turn mimics. J. Mol. Recogn. 1990, 3, pp. 55-64.
Baures et al.—Design, synthesis, x-ray analysis, and dopamine receptor-modulating activity of mimics of the "C5" hydrogen-bonded conformation in the peptidomimetic . . . J. Med. Chem. 1994, 37(22), pp. 3677-3683.
Bolduc et al.—Modified peptide monolayer binding his-tagged biomolecules for small ligand screening with SPR biosensors. Analyst. 2011, 136, pp. 3142-3148.
Bourguet et al.—Solution-phase submonomer diversification of aza-dipeptide building blocks and their application in aza-peptide and aza-DKP synthesis. J. Pept. Sci. 2010, 16, pp. 284-296.
Boutard et al.—Structure-activity analysis of the growth hormone secretagogue GHRP-6 by alpha- and beta-amino gamma-lactam positional scanning. Chem. Biol. Drug. Des. 2010, 75, 40-50.
Boutard et al.—Examination of the active secondary structure of the peptide 101.10, an allosteric modulator of the interleukin-1 receptor . . . J. Peptide Sci. 2011, 17, pp. 288-296.
Bowers et al.—On the actions of the growth hormone-releasing hexapeptide, GHRP. Endocrinology. 1991, 128, pp. 2027-2035.
Bronson et al.—Discovery of the first antibacterial small molecule inhibitors of MurB. Bioorg. Med. Chem. Lett. 2003, 13, pp. 873-875.
Burgey et al.—Benzodiazepine calcitonin gene-related peptide (CGRP) receptor antagonist: optimization of the 4-substituted piperidine. Bioorg. Med. Chem. Lett. 2006, 16, pp. 5052-5056.
Carling et al.—1-(3-cyanobenzylpiperidin-4-yl)-5-methyl-4-phenyl-1,3-dihydroimidazol-2-one: A selective high-affinity antagonist for the human . . . J. Med. Chem. 1999, 42, pp. 2706-2715.
Chiu et al.—Synthesis of imidazolidinediones and oxazolidinediones from cyclizatino of propargylureas and propargyl carbamates. J. Med. Chem. 1979, 22(6), pp. 746-748.
Cliff et al.—Synthesis of 4,4'-biimodazoles. Synthesis 1994, 681.
Congiu et al.—Design, synthesis, and in-vitro antitumor activity of new 1,4-diarylimidazole-2-ones and their 2-thione analogues. Bioorg. Med. Chem. Lett. 2008, 18, pp. 989-993.
Crisma et al.—Peptide models for beta-turns. A circular dichroism study. Int. J. Peptide Protein Res. 1984, 23, pp. 411-419.
Damewood et al.—Nonpeptidic inhibitors of human leukocyte elastase. 2. Design, synthesis, and in vitro activity of a series . . . J. Med. Chem. 1994, 37, pp. 3303-3312.
Demers et al.—Identification of the growth hormone-releasing peptide binding site in CD26 : a photoaffinity cross-linking study. Biochem. J. 2004, 382, pp. 417-424.
Durant—Guanidine derivatives acting at histaminergic receptors. Chem. Soc. Rev. 1985, 84, 375.
Easton et al.—Reactions of acetylenic amines. VIII. Cyclization of acetylenic ureas. J. Org. Chem. 1964, 29, pp. 1851-1855.

(Continued)

*Primary Examiner* — Thomas S Heard
(74) *Attorney, Agent, or Firm* — Nixon & Vanderhye P.C.

(57) ABSTRACT

Novel peptidomimetics comprising N-amino cyclic urea residues are disclosed. Use of such peptidomimetics for modulating the activity of CD36 or IL-1 receptor in a cell, and for treating CD36- or IL-1-related disease, disorder or condition is also described.

19 Claims, 10 Drawing Sheets

(56) References Cited

PUBLICATIONS

Falb et al.—In situ generation of Fmoc-amino acid chlorides using bis-(trichloromethyl) carbonate and its utilization for difficult couplings in solid-phase peptide synthesis. J. Pept. Res. 1999, 53, pp. 507-517.

Freidinger et al.—Bioactive conformation of luteinizing hormone-releasing hormone: evidence from a conformationally constrained analog. Science. 1980, 210, pp. 656-658.

Freidinger et al.—Protected lactam-brideged dipeptides for use as conformational constraints in peptides. J. Org. Chem. 1982, 47, pp. 104-109.

Freidinger—Synthesis of □-lactam-constrained tryptophyllysine derivatives. J. Org. Chem. 1985, 50, pp. 3631-3633.

Fritz et al.—Stereoselective synthesis of imidazolidin-2-ones via Pd-catalyzed alkene carboamination. Scope and limitations. Tetrahedron. 2008, 64(29), pp. 6838-6852.

Giannis et al.—Peptidomimetics for receptor ligands-discovery, development, and medical perspectives. Chem., Int. Ed. 1993, 32, pp. 1244-1267.

Hafner et al.—Synthesis of symmetrically and unsymmetrically substituted N, N'-diaryl-imidazolin-2-ones by copper-catalyzed arylmamidation under microwave-assisted and conventional conditions. Synthesis, 2007, No. 9, pp. 1403-1411.

Harb et al.—The role of the scavenger receptor CD36 in regulating mononuclear phagocyte trafficking to atherosclerotic lesions and vascular inflammation. Cardiovasc Res. 2009 ;83(1): pp. 42-51.

Hirao et al.—An unnatural base pair between imidazole-2-on and 2-amino-6-(2-thienyl)purine in replication and transcription. Nucleic Acids Res. Suppl. 2002, 2, pp. 37-38.

Hirao et al.—A two-unnatural-base-pair system toward the expansion of the genetic code. J. Am. Chem. Soc. 2004,), pp. 13298-13305.

Jamieson et al.—Positional scanning for peptide secondary structure by systematic solid-phase synthesis of amino lactam peptides. J. Am. Chem. Soc. 2009, 131, pp. 7917-7927.

Jimenez et al.—Signals leading to apoptosis-dependent inhibition of neovascularization by thrombospondin-1. Nat Med 6, pp. 41-48 (2000).

Jimenez et al.—c-Jun N-terminal kinase activation is required for the inhibition of neovascularization by thrombospondin-1. Oncogene 7, pp. 3443-3448 (2001).

Kemp et al.—Synthesis and conformational analysis of epindolidione-derived peptide models for β-sheet formation. J. Org. Chem. 1990, 55, pp. 4650-4657.

Kemp et al.—The structure and energetics of helix formation by short template peptides in aqueous solution. 2. Characterization . . . J. Am. Chem. Soc. 1996, 118, pp. 4240-4248.

Lecoq et al.—Crystal state conformation of three azapetides containing the azaproline residue, A β-turn regulator. Biopolymers. 1993, 33(7), pp. 1051-1059.

Lee et al.—A theoretical study of conformational properties of N-methyl azapetide derivatives. J. Am. Chem. Soc. 2002, 124, pp. 11881-11893.

Lei et al.—Palladium(II)-catalyzed tandem intramolecular aminopalladation of alkynes and conjugate addition. Synthesis of oxazolidiones, imidazolidiones, and lactams. Org. Lett. 2000, 2(17), pp. 2699-2702.

Loughlin et al.—Beta-strand mimetics. Chem. Rev. 2004, 104, pp. 6085-6117.

Marraud et al.—Crystal structures of peptides and modified peptides. Biopolymers (Peptide Science) 1996, 40(1), pp. 45-83.

Momany et al.—Conformational energy studies and in vitro and in vivo activity data on growth hormone-releasing peptides. Endocrinology. 1984, 114(5), pp. 1531-1536.

Nowick—Exploring β-sheet structure and interactions with chemical model systems—Accounts of Chemical Research 2008, 41, pp. 1319-1330.

Okamura et al.—CD36 regulates oxidative stress and inflammation in hypercholesterolemic CKD. J Am Soc Nephrol. 2009, 20(3): pp. 495-505.

Peshkov et al.—Tetrasubstituted 2-imidazolones via Ag(I)-catalyzed cycloisomerization of propargylic ureas. J. Org. Chem. 2011, 76, pp. 5867-5872.

Picard et al.,—CD36 plays an important role in the clearance of oxLDL and associated age-dependent sub-retinal deposits. Aging Dec. 2010; 2(12): pp. 981-989.

Proulx et al.—Copper-catalyzed N-arylation of semicarbazones for the synthesis of aza-arylglycine-containing aza-peptides. Org. Lett. 2010. 12(13), pp. 2916-2919.

Proulx et al.—Aza-1,2,3-triazole 3-alamine synthesis via copper-catalyzed 1,3-dipolar cycloaddition on aza-progargyglycine. J. Org. Chem. 2010. 75(15), pp. 5385-5387.

Proulx et al.—Azapeptides and their therapeutic potential. Future Medicinal Chemistry. 2011, 3(9), pp. 1139-1164.

Quiniou et al.—Development of a ovel noncompetitive antagonist of IL-1 receptor. J. Immunol. 2008, 180, pp. 6977-6987.

Rai et al.—Tuning the β-turn segment in designed peptide β-hairpins: construction of a stable type I' β-turn nucleus and hairpin-helix transition promoting segments. Peptide Sci. 2006, 88, pp. 350-361.

Ronga et al.—Insertion of multiple α-Amino ?-lactam (Agl) residues into a peptide sequence by solid-phase synthesis on synphase lanterns. Biopolymers. 2010, 94, pp. 183-191.

Sabatino et al.—Exploring side-chain diversity by submonomer solid-phase aza-peptide synthesis. Org. Lett. 2009, 11, pp. 3650-3653.

Sabatino et al.—Structure-Activity Relationships of GHRP-6 Azapeptide Ligands of the CD36 Scavenger Receptor by Solid-Phase Submonomer Azapeptide Synthesis. J. Am. Chem. Soc. 2011, 133, pp. 12493-12506.

Shaw et al.—Caprolactams as potent CGRP receptor antagonists for the treatment of migraine. Bioorg. Med. Chem. Lett. 2007, 17, pp. 4795-4798.

Smith et al.—Antioxidant properties of 2-imidazolones and 2-imidazolthiones. Biochem. Pharmacol. 1987, 36, pp. 1457-1460.

Smith et al.—Design, synthesis, and crystal structure of a pyrrolionone-based peptodomimetic possessing the conformation . . . J. Am. Chem. Soc. 1992, 114, pp. 10672-10674.

St-Cyr et al.—Crystal-state structural analysis of β-hydroxy-?-lactam constrained ser/thr peptidomimetics. Heterocycles. 2010, 82(1), pp. 729-737.

Van Esseveldt et al.—Novel approach to 5-substituted proline derivatives using a silver-catalyzed cyclization as the key step. J. Org. Chem. 2005, 70, pp. 1791-1795.

Veale et al.—Nonpeptidic inhibitors of human leukocyte elastase. 5. Design, synthesis, and x-ray crystallography . . . J. Med. Chem. 1995, 38, pp. 98-108.

Verniest et al.—Gold- and silver-mediated cycloisomerizations of N-propargylamides. Org. Lett. 2008, 10(19), pp. 4379-4382.

Watanabe et al.—5-aryl-imidazolin-2-ones as a scaffold or potent antioxidant and memory-improving activity. Bioorg. Med. Chem. Lett. 2008, 18, pp. 1478-1483.

Wiltulski et al.—Hydroboration and Suzuki-Miyaura coupling reactions with the electronically modulated variant of an Ynamine: the synthesis of (E)-β-arylenamides. Tetrahedron 2000, 56, pp. 8473-8480.

Wolf et al.—Palladium-catalyzed cyclization reactions of acetylene-containing amino acids. Adv. Synth. Catal. 2002, 344, pp. 70-83.

Wolfe et al.—Stereoselective synthesis of Freidinger lactams using oxaziridines derived from amino acids. J. Org. Chem. 1997, 62, pp. 654-663.

Xue et al.—Synthesis and biological evaluation of imidazole-2-one derivatives as potential antitumor agents. Bioorganic & Medicinal Chemistry 16 (2008) pp. 2550-2557.

Zhang et al.—Combining gold(I)/gold(III) catalysis and C-H functionalization: a formal intramolecular [3+2] annulation towards tricyclic indolines and mechanistic studies. Chem. Int. Ed. 2011, 50, pp. 1-6.

Zouikri et al.—Azaproline as a β-turn-inducer residue opposed to proline. J. Pept. Res. 1998, 52, pp. 19-26.

PEPTIDOMIMETICS COMPRISING N-AMINO CYCLIC UREA RESIDUES AND USES THEREOF

CROSS REFERENCE TO RELATED APPLICATIONS

This application claims the benefit of U.S. Provisional Application Ser. No. 61/655,682, and Canadian Patent Application serial No. 2,779,949, both filed Jun. 5, 2012, which are incorporated herein by reference.

FIELD OF THE INVENTION

The present invention generally relates to peptidomimetics, and more particularly to geometrically restricted peptide analogs.

BACKGROUND OF THE INVENTION

Precise three-dimensional folding of proteins and peptides is important for function. Identification of such biologically active conformations is critical for developing therapeutics based on peptide structures. Geometrically restricted analogs are thus valuable tools, because they reduce energetic costs for folding into binding conformations, and may thereby improve potency, receptor selectivity and metabolic stability.

Synthesis and analysis of constrained peptidomimetics is useful for characterizing the active conformation of biologically relevant peptides. Optimally constrained analogues may exhibit enhanced affinity, because such pre-organized peptides experience less loss of entropy upon receptor binding. In addition, rigid peptide analogues may avoid conformations prone to undesirable effects and exhibit improved pharmacological properties, such as enhanced stability and bioavailability.

The present description refers to a number of documents, the content of which is herein incorporated by reference in their entirety.

SUMMARY OF THE INVENTION

In a first aspect, the present invention provides a peptidomimetics comprising an N-amino cyclic urea residue.

In another aspect, the present invention provides a peptidomimetic of the sequence A:

$Z^1$-Xaa$^1$-Xaa$^2$-Xaa$^3$-Xaa$^4$-Xaa$^5$-Xaa$^6$-$Z^2$ (A);

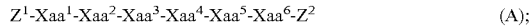

wherein Xaa$^1$ is D-His, L-His, D-Ala, L-Ala or an N-amino cyclic urea residue; Xaa$^2$ is D-Trp, L-Trp, a Trp analog, or an N-amino cyclic urea residue; Xaa$^3$ is D-Ala, L-Ala, D-Pro, L-Pro, D-Lys, L-Lys, or an N-amino cyclic urea residue; Xaa$^4$ is D-Trp, L-Trp, a Trp analog or an N-amino cyclic urea residue; Xaa$^5$ is D-Phe, L-Phe or an N-amino cyclic urea residue; Xaa$^6$ is D-Lys, L-Lys or an N-amino cyclic urea residue; $Z^1$ is H or an amino-terminal modifying group; and $Z^2$ is a carboxyl group or a carboxy-terminal modifying group; and wherein at least one of Xaa$^1$ to Xaa$^6$ is an N-amino cyclic urea residue, or a pharmaceutically acceptable salt thereof. In an embodiment, the peptidomimetic of the sequence A binds to CD36 and modulates (e.g., inhibits) CD36 activity, for example TLR2 activation.

In another aspect, the present invention provides a peptidomimetic of the sequence B:

$Z^1$-Xaa$^7$-Xaa$^8$-Xaa$^9$-Xaa$^{10}$-Xaa$^{11}$-Xaa$^{12}$-Xaa$^{13}$-$Z^2$ (B),

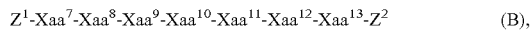

wherein Xaa$^7$ is D-Arg, L-Arg or an N-amino cyclic urea residue; Xaa$^8$ is D-Tyr, L-Tyr or an N-amino cyclic urea residue; Xaa$^9$ is D-Thr, L-Thr or an N-amino cyclic urea residue; Xaa$^{10}$ is D-Val, L-Val or an N-amino cyclic urea residue; Xaa$^{11}$ is D-Glu, L-Glu or an N-amino cyclic urea residue; Xaa$^{12}$ is D-Leu, L-Leu or an N-amino cyclic urea residue; Xaa$^{13}$ is D-Ala, L-Ala or an N-amino cyclic urea residue; $Z^1$ is H or an amino-terminal modifying group; and $Z^2$ is H or a carboxy-terminal modifying group; and wherein at least one of Xaa$^7$ to Xaa$^{13}$ is an N-amino cyclic urea residue, or a pharmaceutically acceptable salt thereof. In an embodiment, the peptidomimetic of the sequence B binds to IL-1R and modulates (e.g., inhibits) IL-1R activity.

In an embodiment, the N-amino cyclic urea residue is of any one of formulas I to IX:

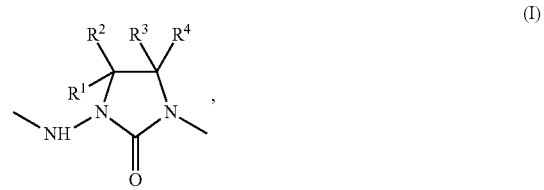

(I)

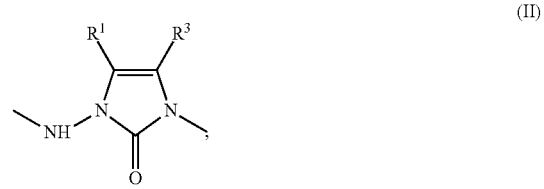

(II)

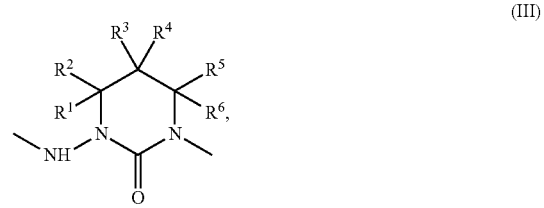

(III)

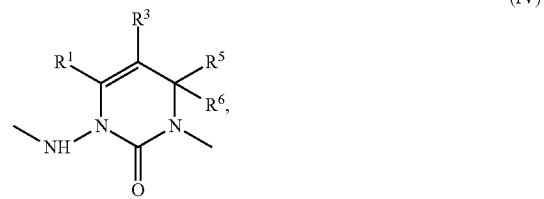

(IV)

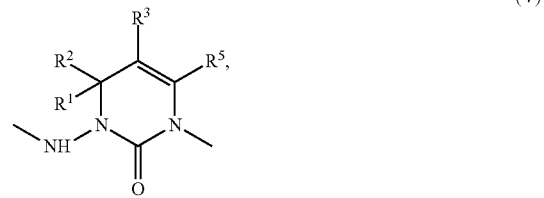

(V)

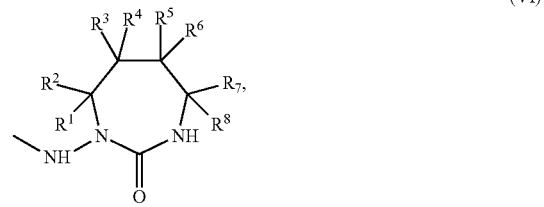

(VI)

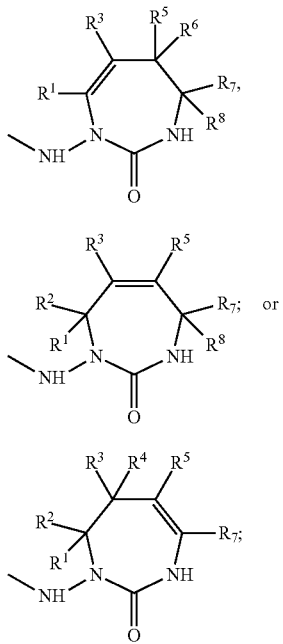

wherein $R^1$, $R^2$, $R^3$, $R^4$, $R^5$, $R^6$, $R^7$ and $R^8$ are each independently R, halogen, —OR, —SR, —N(R)$_2$, —CN, —NO$_2$, —C(O)R, —CO$_2$R, —C(O)N(R)$_2$, —C(O)C(O)R, —C(O)CH$_2$C(O)R, —S(O)R, —SO$_2$R, —SO$_2$N(R)$_2$, —NRC(O)R, —NRC(O)N(R)$_2$, —NRSO$_2$R, —NRSO$_2$N(R)$_2$, —N(R)N(R)$_2$, —C=NN(R)$_2$, —C=NOR, —OC(O)R, or —OC(O)N(R)$_2$; wherein R is independently hydrogen or an optionally substituted group selected from $C_{1-6}$ aliphatic; phenyl; a 3- to 7-membered saturated or partially unsaturated carbocyclic ring; a 5- to 6-membered monocyclic heteroaryl ring having 1-3 heteroatoms independently selected from nitrogen, oxygen, and sulfur; or a 4- to 7-membered saturated or partially unsaturated heterocyclic ring having 1-3 heteroatoms independently selected from nitrogen, oxygen, and sulfur, or wherein two adjacent Rx groups (e.g., $R^1$ and $R^2$; $R^3$ and $R^4$; $R^5$ and $R^6$; and $R^7$ and $R^8$) and the carbon atom to which they are bound forms a C=O, C=S or C=NR group.

In an embodiment, $R^1$, $R^2$, $R^3$, $R^4$, $R^5$, $R^6$, $R^7$ and $R^8$ are each independently H, an alkyl or an arylalkyl, substituted or unsubstituted; saturated or unsaturated; branched or unbranched.

In an embodiment, the alkyl is a $C_1$ to $C_6$ alkyl, in a further embodiment a $C_1$ to $C_3$ alkyl, such as methyl.

In an embodiment, the arylalkyl is CH$_2$-Ph.

In an embodiment, the N-amino cyclic urea residue is of formula I. In a further embodiment, $R^1$, $R^2$, $R^3$ and $R^4$ are H.

In an embodiment, the N-amino cyclic urea residue is of formula II. In a further embodiment, $R^1$ and $R^3$ are H. In another embodiment, $R^1$ is H and $R^3$ is a $C_1$ to $C_6$ alkyl or an arylalkyl. In another embodiment $R^1$ is a substituted or unsubstituted aryl (e.g., phenyl), and $R^3$ is a $C_1$ to $C_6$ alkyl, preferably methyl. In a further embodiment, $R^1$ is a substituted aryl (e.g., phenyl), for example a phenyl substituted with a nitro (NO$_2$) group or with a $C_1$ to $C_6$ alkyl (substituted or unsubstituted), e.g., an alkyl substituted with one or more halogens, such as trifluoromethyl.

In an embodiment, the N-amino cyclic urea residue is of formula III. In a further embodiment, $R^1$, $R^2$, $R^3$, $R^4$, $R^5$ and $R^6$ are H.

In an embodiment, the N-amino cyclic urea residue is of formula VIII. In a further embodiment, $R^1$, $R^2$, $R^3$, $R^5$, $R^7$ and $R^8$ are H.

In an embodiment, the peptidomimetic or salt thereof comprises one N-amino cyclic urea residue. In an embodiment, Xaa$^1$, Xaa$^2$, Xaa$^3$, Xaa$^4$ or Xaa$^5$ is said N-amino cyclic urea residue. In a further embodiment, Xaa$^4$ is said N-amino cyclic urea residue.

In an embodiment, Xaa$^2$ is D-Trp. In another embodiment, Xaa$^5$ is D-Phe. In an embodiment, Xaa$^1$ is His, Xaa$^2$ is D-Trp, Xaa$^3$ is Ala, Xaa$^5$ is D-Phe and Xaa$^6$ is Lys.

In an embodiment, the peptidomimetic is a compound having one of the following formulas: His-D-Trp-Ala-(N-amino-4-methyl-5-phenyl-imidazol-2-one)-L-Phe-Lys-NH$_2$, His-D-Trp-Ala-(N-amino-4-methyl-5-phenyl-imidazolin-2-one)-DL-Phe-Lys-NH$_2$, His-D-Trp-Ala-(N-amino-4-methyl-5-p-toluoyl-imidazol-2-one)-DL-Phe-Lys-NH$_2$, His-D-Trp-Ala-(N-amino-4-methyl-5-m-trifluoromethylphenyl-imidazol-2-one)-DL-Phe-Lys-NH$_2$, His-D-Trp-Ala-(N-amino-4-methyl-5-p-nitrophenyl-imidazol-2-one)-DL-Phe-Lys-NH$_2$, His-D-Trp-Ala-(N-amino-imidazolidin-2-one)-D-Phe-Lys-NH$_2$, His-D-Trp-Ala-(N-amino-4-methyl-imidazolin-2-one)-D-Phe-Lys-NH$_2$, His-D-Trp-Ala-(N-amino-4-benzyl-imidazolin-2-one)-D-Phe-Lys-NH$_2$, His-D-Trp-Lys-(N-amino-4-methyl-imidazol-2-one)-D-Phe-Lys-NH$_2$, Ala-D-Trp-Lys-(N-amino-4-methyl-imidazolin-2-one)-D-Phe-Lys-NH$_2$, His-D-Trp-D-Lys-(N-amino-4-methyl-imidazolin-2-one)-D-Phe-Lys-NH$_2$, Ala-D-Trp-D-Lys-(N-amino-4-methyl-imidazolin-2-one)-D-Phe-Lys-NH$_2$, His-D-Trp-Pro-(N-amino-4-methyl-imidazolin-2-one)-D-Phe-Lys-NH$_2$, Ala-D-Trp-Pro-(N-amino-4-methyl-imidazolin-2-one)-D-Phe-Lys-NH$_2$, His-D-Trp-D-Pro-(N-amino-4-methyl-imidazolin-2-one)-D-Phe-Lys-NH$_2$, or Ala-D-Trp-D-Pro-(N-amino-4-methyl-imidazolin-2-one)-D-Phe-Lys-NH$_2$, or a pharmaceutically acceptable salt thereof.

In an embodiment, Xaa$^9$ is said N-amino cyclic urea residue.

In embodiments, Xaa$^7$ is D-Arg, Xaa$^8$ is D-Tyr, Xaa$^{10}$ is D-Val, Xaa$^{11}$ is D-Glu, Xaa$^{12}$ is D-Leu, and/or Xaa$^{13}$ is D-Ala.

In an embodiment, $Z^1$ is H. In another embodiment, $Z^1$ is an amino-terminal modifying group, and wherein said amino-terminal modifying group is (i) an acyl group (R—CO—), wherein R is a hydrophobic moiety, or (ii) an aroyl group (Ar—CO—), wherein Ar is an aryl group.

In an embodiment, $Z^2$ is a carboxyl group. In another embodiment, $Z^2$ is a carboxy-terminal modifying group, wherein said carboxy-terminal modifying group is a hydroxamate group, a nitrile group, an amide group, an alcohol or CH$_2$OH, in a further embodiment NH$_2$.

In another aspect, the present invention provides the above-mentioned peptidomimetic of sequence A for modulating the activity of CD36 in a cell.

In another aspect, the present invention provides the above-mentioned peptidomimetic of sequence A for the preparation of a medicament for modulating the activity of CD36 in a cell.

In another aspect, the present invention provides the above-mentioned peptidomimetic of sequence A for the treatment of a CD36-related disease, disorder or condition in a subject.

In another aspect, the present invention provides the above-mentioned peptidomimetic of sequence A for the preparation of a medicament for the treatment of a CD36-related disease, disorder or condition in a subject.

In another aspect, the present invention provides the use of the above-mentioned peptidomimetic of sequence A for modulating the activity of CD36 in a cell.

In another aspect, the present invention provides the use of the above-mentioned peptidomimetic of sequence A for the preparation of a medicament for modulating the activity of CD36 in a cell.

In another aspect, the present invention provides the use of the above-mentioned peptidomimetic of sequence A for the treatment of a CD36-related disease, disorder or condition in a subject.

In another aspect, the present invention provides the use of the above-mentioned peptidomimetic of sequence A for the preparation of a medicament for the treatment of a CD36-related disease, disorder or condition in a subject.

In another aspect, the present invention provides method (e.g., in vitro) of modulating the activity of CD36 in a cell, the method comprising contacting the cell with the above-mentioned peptidomimetic of sequence A.

In another aspect, the present invention provides method of treating a CD36-related disease, disorder or condition, the method comprising administering to a subject in need thereof the above-mentioned peptidomimetic of sequence A.

In an embodiment, the above-mentioned CD36-related disease, disorder or condition is atherosclerosis, age-related macular degeneration, fibrinogenesis in chronic kidney disease or myocardial ischemia/reperfusion injury.

In another aspect, the present invention provides the above-mentioned peptidomimetic of formula B for modulating the activity of an IL-1 receptor in a cell.

In another aspect, the present invention provides the above-mentioned peptidomimetic of sequence B for the preparation of a medicament for modulating the activity of an IL-1 receptor in a cell.

In another aspect, the present invention provides the above-mentioned peptidomimetic of sequence B for the treatment of an IL-1-related disease, disorder or condition in a subject.

In another aspect, the present invention provides the above-mentioned peptidomimetic of sequence B for the preparation of a medicament for the treatment of an IL-1-related disease, disorder or condition in a subject.

In another aspect, the present invention provides the use of the above-mentioned peptidomimetic of sequence B for modulating the activity of an IL-1 receptor in a cell.

In another aspect, the present invention provides the use of the above-mentioned peptidomimetic of sequence B for the preparation of a medicament for modulating the activity of an IL-1 receptor in a cell.

In another aspect, the present invention provides the use of the above-mentioned peptidomimetic of sequence B for the treatment of an IL-1-related disease, disorder or condition in a subject.

In another aspect, the present invention provides the use of the above-mentioned peptidomimetic of sequence B for the preparation of a medicament for the treatment of an IL-1-related disease, disorder or condition in a subject.

In another aspect, the present invention provides method (e.g., in vitro) of modulating the activity of an IL-1 receptor in a cell, the method comprising contacting the cell with the above-mentioned peptidomimetic of sequence B.

In another aspect, the present invention provides method of treating an IL-1-related disease, disorder or condition, the method comprising administering to a subject in need thereof the above-mentioned peptidomimetic of sequence B.

In an embodiment, the above-mentioned an IL-1-related disease, disorder or condition is an inflammatory disease, disorder or condition. In a further embodiment, the above-mentioned inflammatory disease, disorder or condition is rheumatoid arthritis, inflammatory bowel disease, septic shock, osteoarthritis, psoriasis, encephalitis, glomerulonephritis, respiratory distress syndrome, Reiter's syndrome, systemic lupus erythematosus, scleroderma, Crohn's disease, ulcerative colitis, inflammatory joint disease, cachexia in certain leukemias, Alzheimer's disease, numerous types of cancers, diabetes mellitus (type I), pulmonary hypertension, stroke, periventricular leucopenia, meningitis, CNS demyelinating diseases, multiple sclerosis, acute disseminated encephalomyelitis (ADEM), idiopathic inflammatory demyelinating disease, transverse myelitis, Devic's disease, progressive multifocal leukoencephaly, Guillain-Barre syndrome, chronic inflammatory demyelinating polyneuropathy, anti-MAG neuropathy, inflammatory bowel disease, sepsis, septic shock, adult respiratory distress syndrome, pancreatitis, trauma-induced shock, asthma, bronchial asthma, allergic rhinitis, cystic fibrosis, stroke, acute bronchitis, chronic bronchitis, acute bronchiolitis, chronic bronchiolitis, gout, spondylarthropathris, ankylosing spondylitis, Reiter's syndrome, psoriatic arthropathy, enterapathric spondylitis, juvenile arthropathy or juvenile ankylosing spondylitis, reactive arthropathy, infectious or post-infectious arthritis, gonoccocal arthritis, tuberculous arthritis, viral arthritis, fungal arthritis, syphilitic arthritis, Lyme disease, arthritis associated with vasculitic syndromes, polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury, miscellaneous forms of arthritis, neuropathic joint disease, hemarthrosis, Henoch-Schonlein purpura, hypertrophic osteoarthropathy, multicentric reticulohistiocytosis, arthritis associated with certain diseases, surcoilosis, hemochromatosis, sickle cell disease and other hemoglobinopathies, hyperlipoproteineimia, hypogammaglobulinemia, hyperparathyroidism, acromegaly, familial Mediterranean fever, Behat's Disease, systemic lupus erythrematosis, and relapsing polychondritis, inflammatory conditions resulting from harmful stimuli, such as pathogens, damaged cells, or irritants, sarcoidosis, disseminated intravascular coagulation, atherosclerosis, Kawasaki's disease, macrophage activation syndrome (MAS), HIV, graft-versus-host disease, Sjogren's syndrome, vasculitis, autoimmune thyroiditis, dermatitis, atopic dermatitis, myasthenia gravis, inflammatory conditions of the skin, cardiovascular system, nervous system, liver, kidney and pancreas, cirrhosis, eosinophilic esophagitis, cardiovascular disorders, disorders associated with wound healing, respiratory disorders, chronic obstructive pulmonary disease, emphysema, acute inflammatory conditions, atopic inflammatory disorders, bacterial, viral, fungal or protozoan infections, pulmonary diseases, systemic inflammatory response syndrome (SIRS), hemophagocytic lymphohistiocytosis (HLH), juvenile rheumatoid arthritis, osteoarthritis, psoriatic arthritis, lupus nephritis, lupus-associated arthritis, ankylosing spondylitis, and/or autoimmune diseases.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 3B shows the circular dichroism spectra of S- and R-31a;

DISCLOSURE OF INVENTION

Figure 1:
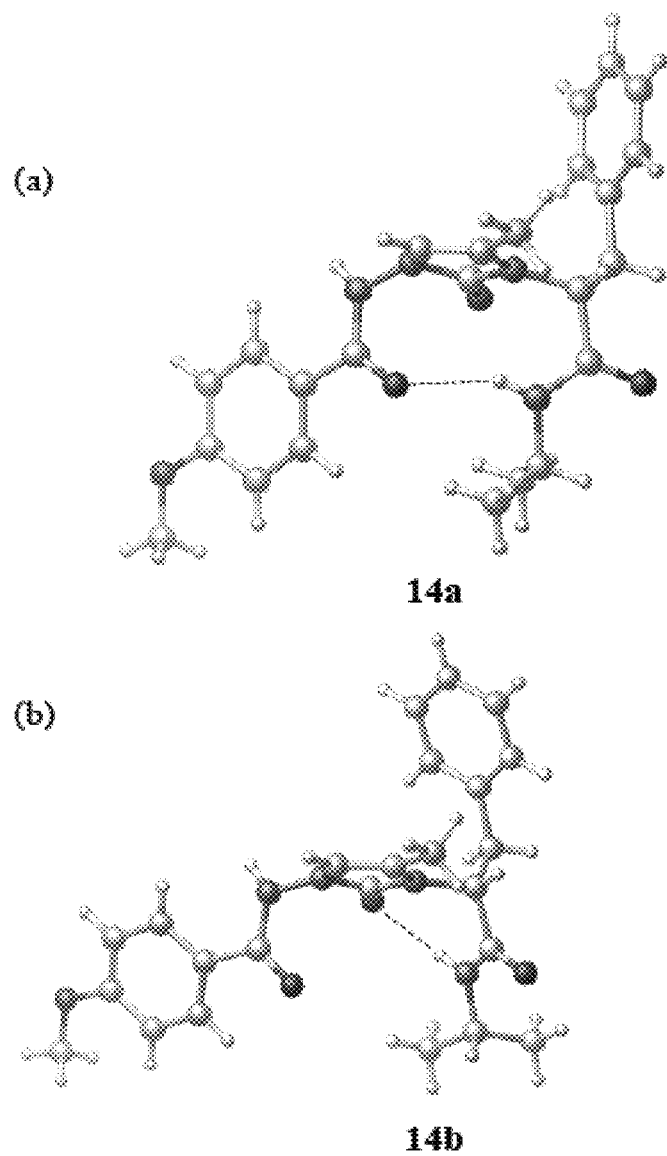
FIG. 1 shows X-ray structures of N-acyl amino imidazolin-2-one isopropyl amide 14. (a) Broken line represents an inferred hydrogen bond between the C(O) of the PMP ketone and the NH of the isopropyl amide. (b) Broken line represents an inferred hydrogen bond between the C(O) of the imidazolin-2-one and the NH of the isopropyl amide.

In the studies described herein, the present inventors have demonstrated the synthesis of N-amino cyclic urea peptidomimetics. N-Amino cyclic urea residues were introduced into the interleukin-1 (IL-1) receptor negative modulator 101.10, a D-heptapeptide having the sequence D-Arg-D-Tyr-D-Thr-D-Val-DGlu-D-Leu-D-Ala-NH$_2$ and a synthetic Growth Hormone-Releasing Peptide-6 (His-D-Trp-Ala-Trp-D-Phe-Lys-NH$_2$) with affinity for the ghrelin and CD36 receptors.

Accordingly, in a first aspect, the present invention provides a peptidomimetic comprising at least one N-Amino cyclic urea residue.

The present invention also provides a peptidomimetic of the sequence A:

$$Z^1\text{-Xaa}^1\text{-Xaa}^2\text{-Xaa}^3\text{-Xaa}^4\text{-Xaa}^5\text{-Xaa}^6\text{-}Z^2 \quad (A);$$

wherein Xaa$^1$ is D-His, L-His, D-Ala, L-Ala or an N-amino cyclic urea residue; Xaa$^2$ is D-Trp, L-Trp, a Trp analog, or an N-amino cyclic urea residue; Xaa$^3$ is D-Ala, L-Ala, D-Pro, L-Pro, D-Lys, L-Lys, or an N-amino cyclic urea residue; Xaa$^4$ is D-Trp, L-Trp, a Trp analog or an N-amino cyclic urea residue; Xaa$^5$ is D-Phe, L-Phe or an N-amino cyclic urea residue; Xaa$^6$ is D-Lys, L-Lys or an N-amino cyclic urea residue; Z$^1$ is H or an amino-terminal modifying group; and Z$^2$ is a carboxyl group or a carboxy-terminal modifying group; and wherein at least one of Xaa$^1$ to Xaa$^6$ is an N-amino cyclic urea residue. In an embodiment, the Trp analog is an alkyl tryptophan (e.g., a D- or L-tryptophan residue substituted with an alkyl), in an embodiment a D-2-alkyl tryptophan (D-2-$C_1$-$C_3$alkyl tryptophan), for example 2-methyl D-tryptophan (2MeD-Trp or Mrp) (see, e.g., U.S. Pat. No. 5,955,421).

The present invention also provides a peptidomimetic of the sequence B $$Z^1\text{-Xaa}^7\text{-Xaa}^8\text{-Xaa}^9\text{-Xaa}^{10}\text{-Xaa}^{11}\text{-Xaa}^{12}\text{-Xaa}^{13}\text{-}Z^2 \quad (B),$$

wherein Xaa$^7$ is D-Arg, L-Arg or an N-amino cyclic urea residue; Xaa$^8$ is D-Tyr, L-Tyr or an N-amino cyclic urea residue; Xaa$^9$ is D-Thr, L-Thr or an N-amino cyclic urea residue; Xaa$^{10}$ is D-Val, L-Val or an N-amino cyclic urea residue; Xaa$^{11}$ is D-Glu, L-Glu or an N-amino cyclic urea residue; Xaa$^{12}$ is D-Leu, L-Leu or an N-amino cyclic urea residue; Xaa$^{13}$ is D-Ala, L-Ala or an N-amino cyclic urea residue; Z$^1$ is H or an amino-terminal modifying group; and Z$^2$ is H or a carboxy-terminal modifying group; and wherein at least one of Xaa$^7$ to Xaa$^{13}$ is an N-amino cyclic urea residue, or a pharmaceutically acceptable salt thereof.

In an embodiment, the above-mentioned peptidomimetic comprises three (3) N-amino cyclic urea residues or less. In further embodiments, the above-mentioned peptidomimetic comprises two (2) N-amino cyclic urea residues or less, in a further embodiment one. In an embodiment, the above-mentioned peptidomimetic comprises at least two (e.g., at least three, four, five or six) contiguous amino acids that appear in the native sequence of the peptides (D/L)His-(D/L)Trp-(D/L)Ala-(D/L)Trp-(D/L)Phe-(D/L)Lys or (D/L)Arg-(D/L)Tyr-(D/L)Thr-(D/L)Val-(D/L)Glu-(D/L)Leu-(D/L)Ala.

In an embodiment, the above-mentioned N-amino cyclic urea residue is of any one of formulas I to IX:

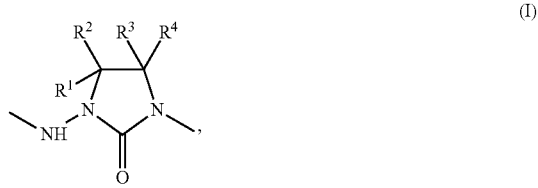

(I)

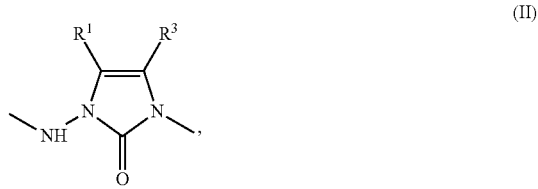

(II)

-continued (III) 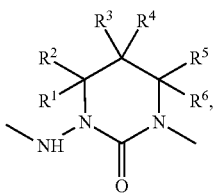

(IV) 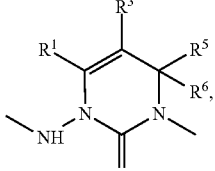

(V) 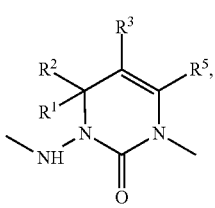

(VI) 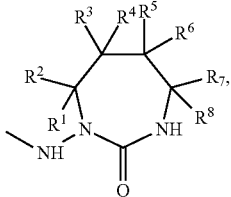

(VII) 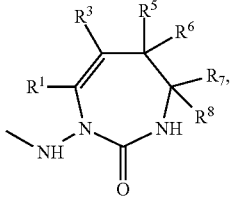

(VIII) 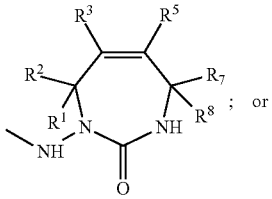 ; or (IX) 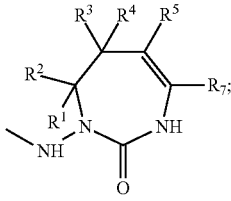

wherein $R^1$, $R^2$, $R^3$, $R^4$, $R^5$, $R^6$, $R^7$ and $R^8$ are each independently R, halogen, —OR, —SR, —N(R)$_2$, —CN, —NO$_2$, —C(O)R, —CO$_2$R, —C(O)N(R)$_2$, —C(O)C(O)R, —C(O)CH$_2$C(O)R, —S(O)R, —SO$_2$R, —SO$_2$N(R)$_2$, —NRC(O)R, —NRC(O)N(R)$_2$, —NRSO$_2$R, —NRSO$_2$N(R)$_2$, —N(R)N(R)$_2$, —C=NN(R)$_2$, —C=NOR, —OC(O)R, or —OC(O)N(R)$_2$; wherein R is independently hydrogen or an optionally substituted group selected from C$_{1-6}$ aliphatic; aryl (e.g., phenyl); a 3- to 7-membered saturated or partially unsaturated carbocyclic ring; a 5- to 6-membered monocyclic heteroaryl ring having 1-3 heteroatoms independently selected from nitrogen, oxygen, and sulfur; or a 4- to 7-membered saturated or partially unsaturated heterocyclic ring having 1-3 heteroatoms independently selected from nitrogen, oxygen, and sulfur, or wherein two adjacent Rx groups (e.g., $R^1$ and $R^2$, $R^3$ and $R^4$; $R^5$ and $R^6$; and $R^7$ and $R^8$) and the carbon atom to which they are bound forms a double bond, for example C=O, C=S or C=NR group, wherein R is as defined above.

In an embodiment, $R^1$, $R^2$, $R^3$, $R^4$, $R^5$, $R^6$, $R^7$ and $R^8$ are each independently H, an alkyl, a heteroalkyl, an aryl, a heteroaryl, an arylalkyl or a heteroarylalkyl, substituted or unsubstituted; saturated or unsaturated; branched or unbranched. In an embodiment, $R^1$, $R^2$, $R^3$, $R^4$, $R^5$, $R^6$, $R^7$ and $R^8$ are each independently H, an alkyl or an arylalkyl, substituted or unsubstituted; saturated or unsaturated; branched or unbranched.

In embodiments, at least one of $R^1$, $R^2$, $R^3$, $R^4$, $R^5$, $R^6$, $R^7$ and $R^8$ corresponds to a side chain of an amino acid, in particular to the side chain of the amino acid that is replaced by the N-amino cyclic urea residue in the sequence.

Accordingly, in embodiments, if Xaa$^1$ is replaced by the N-amino cyclic urea residue, at least one of $R^1$, $R^2$, $R^3$, $R^4$, $R^5$, $R^6$, $R^7$ and $R^8$ is the side chain of histidine:

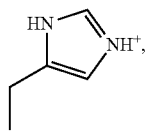

if Xaa$^2$ is replaced by the N-amino cyclic urea residue, at least one of $R^1$, $R^2$, $R^3$, $R^4$, $R^5$, $R^6$, $R^7$ and $R^8$ is the side chain of tryptophan:

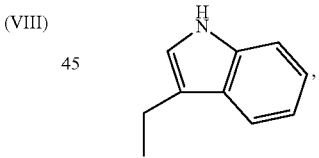

if Xaa$^3$ is replaced by the N-amino cyclic urea residue, at least one of $R^1$, $R^2$, $R^3$, $R^4$, $R^5$, $R^6$, $R^7$ and $R^8$ is the side chain of alanine (CH$_3$), etc.

In another embodiment, the N-amino cyclic urea residue is of formula X:

(X) 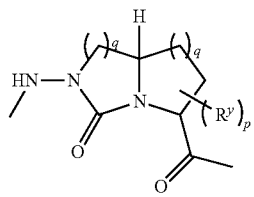

wherein:
each $R^y$ is independently —R, halogen, —OR, —SR, —N(R)$_2$, —CN, —NO$_2$, —C(O)R, —CO$_2$R, —C(O)N(R)$_2$, —C(O)C(O)R, —C(O)CH$_2$C(O)R, —S(O)R, —SO$_2$R, —SO$_2$N(R)$_2$, —NRC(O)R, —NRC(O)N(R)$_2$, —NRSO$_2$R, —NRSO$_2$N(R)$_2$, —N(R)N(R)$_2$, —C=NN(R)$_2$, —C=NOR, —OC(O)R, or —OC(O)N(R)$_2$;

each R is independently hydrogen or an optionally substituted group selected from C$_{1-6}$ aliphatic; phenyl; a 3- to 7-membered saturated or partially unsaturated carbocyclic ring; a 5- to 6-membered monocyclic heteroaryl ring having 1-3 heteroatoms independently selected from nitrogen, oxygen, and sulfur; or a 4- to 7-membered saturated or partially unsaturated heterocyclic ring having 1-3 heteroatoms independently selected from nitrogen, oxygen, and sulfur; or two R groups attached to the same nitrogen atom may be taken together with their intervening atoms to form a 4- to 7-membered saturated or partially unsaturated heterocyclic ring having 1-2 heteroatoms independent selected from nitrogen, oxygen, and sulfur; p is 0, 1, or 2; and each q is independently 0, 1, 2, or 3.

In some embodiments, p of is 0. In other embodiments, p is 1 or 2. In some embodiments, each q of formula (X) is 1 or 2.

In an embodiment, the N-amino cyclic urea residue is of formula I. In an embodiment, the N-amino cyclic urea residue is of formula I, wherein R$^1$, R$^2$, R$^3$ and R$^4$ are H. In another embodiment, the N-amino cyclic urea residue is of formula I, wherein R$^1$, R$^2$ and R$^3$ are H and R$^4$ is a C$_1$ to C$_6$ alkyl or an arylalkyl.

In another embodiment, the N-amino cyclic urea residue is of formula II (4-imidazolin-2-one derivative). In an embodiment, the N-amino cyclic urea residue is of formula II, wherein R$^1$ and R$^3$ are H (4-imidazolin-2-one). In another embodiment, the N-amino cyclic urea residue is of formula II, wherein R$^1$ is H and R$^3$ is a C$_1$ to C$_6$ alkyl or an arylalkyl.

In an embodiment, the above-mentioned alkyl is a C$_1$ to C$_6$ alkyl, for example a C$_1$ to C$_4$ alkyl, in further embodiment methyl, acetyl or propyl. In a further embodiment, the above-mentioned alkyl is a methyl.

In an embodiment, the above-mentioned arylalkyl is R$^9$-aryl, wherein R$^9$ is a C$_1$ to C$_6$ alkyl, for example a C$_1$ to C$_4$ alkyl, and the aryl is a carbocyclic ring system having 6 carbon atoms optionally substituted with one, two, three, four, five or six substituents located at any position of the ring. In a further embodiment, the aryl is phenyl. In a further embodiment, the above-mentioned arylalkyl is CH$_2$-Phenyl (benzyl).

In another embodiment, the N-amino cyclic urea residue is of formula III. In a further embodiment, the N-amino cyclic urea residue is of formula III, wherein R$^1$, R$^2$, R$^3$, R$^4$, R$^5$ and R$^6$ are H.

In another embodiment, the N-amino cyclic urea residue is of formula VIII. In a further embodiment, the N-amino cyclic urea residue is of formula VIII, wherein R$^1$, R$^2$, R$^3$, R$^5$, R$^7$ and R$^8$ are H.

As used herein, the term "arylalkyl" means an alkyl group (e.g., a lower alkyl group) where one of the hydrogens is substituted with aryl (e.g., benzene, naphthalene, anthracene, or phenanthrene). Exemplary arylalkyl groups include benzyl and phenethyl. Arylalkyl groups may be unsubstituted or substituted with, for example, 1, 2, 3, 4, 5, 6, or 7 substituent groups located at any position (i.e., on the sp$^2$ or the sp$^3$ hybridized carbons of the group).

As used herein, the term "aryl" means mono- or bicyclic carbocyclic ring system having 6 to ten carbon atoms forming one or two aromatic rings and is exemplified by phenyl, naphthyl, 1,2-dihydronaphthyl, 1,2,3,4-tetrahydronaphthyl, fluorenyl, indanyl, indenyl, tolyl, alkyloxyphenyl, alkyloxycarbonylphenyl, halophenyl and the like, and may be optionally substituted with one, two, three, four, five or six substituents located at any position of the ring.

As used herein, the term "heteroarylalkyl" means an alkyl group (e.g., a lower alkyl group) where one of the hydrogens is substituted with heteroaryl. Heteroarylalkyl groups may be unsubstituted or substituted with, for example, 1, 2, 3, 4, 5, 6, or 7 substituent groups.

The term "heteroaryl," as used herein, represents that subset of heterocycles, as defined herein, which are aromatic: i.e., they contain 4n+2 pi electrons within the mono- or multicyclic ring system. Illustrative examples of heteroaryl groups include, but are not limited to, pyridyl, pyridazinyl, pyrazinyl, pyrimidinyl, triazinyl, quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridines, benzothiaxolyl, benzofuranyl, benzothienyl, indolyl, isothiazolyl, pyrazolyl, indazolyl, imidazolyl, triazolyl, tetrazolyl, oxazolyl, isoxazolyl, oxadiazolyl, thiadiazolyl, pyrrolyl, thiazolyl, furyl, thienyl and the like. Five- or six-membered monocyclic heteroaryl rings include: pyridyl, pyridazinyl, pyrazinyl, pyrimidinyl, triazinyl, isothiazolyl, pyrazolyl, imidazolyl, triazolyl, tetrazolyl, oxazolyl, isoxazolyl, oxadiazolyl, thiadiazolyl, pyrrolyl, thiazolyl, furyl, thienyl and the like. Eight- to ten-membered bicyclic heteroaryl rings having one to four heteroatoms include: quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridinyl, benzothiaxolyl, benzofuranyl, benzothienyl, indolyl, indazolyl, and the like. Heteroaryls may be unsubstituted or substituted with 1, 2, 3, 4, 5, or 6 substituents.

The terms "alkyl" as used herein, are inclusive of both straight chain and branched chain saturated groups of from 1 to 18 carbons, unless otherwise specified. The term "lower alkyl" as used herein means alkyl groups of from 1 to 7 carbon atoms that consist of a straight, branched or cyclic configuration. Lower alkyls may include 1, 2, 3, 4, 5, 6, or 7 carbon atoms. Examples of lower alkyl groups include, but are not limited to: methyl, ethyl, propyl, isopropyl, n-, sec-, iso- and tert-butyl, pentyl, isoamyl, hexyl, heptyl, cyclopropyl, cyclobutyl, cyclopentyl, cyclohexyl, cyclobutylmethyl, and cycloheptyl, among others. A lower alkyl may be optionally substituted.

The term "heteroalkyl" refers to an alkyl as described above in which at least one carbon of the alkyl is replaced by a heteroatom, for example N, O, P, B, S, Si, Sb, Al, Sn, As, Se or Ge.

The term "alkenyl" as used herein, represents monovalent straight or branched chain groups of, unless otherwise specified, from 2 to 7 carbons containing one or more carbon-carbon double bonds. The radical may be a linear or branched chain, in the E or Z form, and optionally substituted with one to three substituents. Illustrative examples of alkenyl groups include, but are not limited to, vinyl, 1-propenyl, 2-propenyl, isopropenyl, 1-butenyl, 2-butenyl, isobutenyl, 2-methyl-1-propenyl, 1-pentenyl, 2-pentenyl, 4-methyl-2-pentenyl, 1,3-pentadienyl, 2,4-pentadienyl, 1,3-butadienyl and the like.

As used herein, the term "alkynyl" means monovalent, unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$) alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or optionally substituted with one or two suitable substituents.

Where a group may be optionally substituted, optional substituents include, but are not limited to: hydroxy (—OH), —CN, —$NO_2$, halogen (i.e., —F, —Cl, —Br, or —I), —$CO_2$H, —$CO_2$(lower alkyl), —$CO_2$(lower alkoxyalkyl), -(lower alkyl), -(lower alkoxyalkyl), —O(lower alkyl), —O(lower alkoxyalkyl), —NH(lower alkyl), —NH(lower alkoxyalkyl), —N(lower alkyl)$_2$, and —N(lower alkoxyalkyl)$_2$. In some embodiments, a substituted group may have 1, 2, 3, 4, 5, 6, 7, 8, or 9 substituents located at any position. In some embodiments, a substituent group that includes lower alkyl or lower alkoxy is further substituted.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments, aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

"Carbocyclo", or "carbocyclic", used alone or as part of a larger moiety, refer to a saturated or partially unsaturated cyclic aliphatic monocyclic or bicyclic ring systems, as described herein, having from 3 to 10 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl, tetrahydronaphthyl, decalin, or bicyclo[2.2.2]octane, where the radical or point of attachment is on an aliphatic ring.

As used herein, "amino acid" refers to a compound comprising an amino functional group and a carboxylic functional group. Types of amino acids include "α-amino acids," wherein the amino and carboxylic groups are attached to the same carbon. In "p-amino acids" the carbon to which the amino group is attached is adjacent to the carbon to which the carboxylic group is attached, and in "γ-amino acids," there is an additional intervening carbon. Amino acids can have the L-configuration (for example, natural amino acids have the L-configuration) or the D-configuration. Amino acids include natural amino acids and unnatural amino acids. A "natural amino acid" refers to an amino acid that is naturally produced or found in a mammal. Natural amino acids can be encoded by the standard genetic code or may result from, for example, post-translational modifications. Natural amino acids include the twenty proteinogenic L-amino acids (Alanine (A), Cysteine (C), Serine (S), Threonine (T), Aspartic Acid (D), Glutamic Acid (E), Asparagine (N), Glutamine (Q), Histidine (H), Arginine (R), Lysine (K), Isoleucine (I), Leucine (L), Methionine (M), Valine (V), Phenylalanine (F), Tyrosine (Y), Tryptophan (W), Glycine (G), and Proline (P)). Preferred natural amino acids for use in any of the compositions and methods of the invention include L-phenylalanine and L-proline. An "unnatural amino acid" is an amino acid that is not naturally produced (e.g., encoded by the genetic code or resulting from a posttranslational modification) or naturally found in a mammal. Unnatural amino acids include amino acids that normally do not occur in proteins (e.g., an α-amino acid having the D-configuration, or a (D,L)-isomeric mixture thereof), homologues of naturally occurring amino acids, an α,α-disubstituted analogue of a naturally occurring amino acid, or an α-amino acid wherein the amino acid side chain has been shortened by one or two methylene groups or lengthened to up to 10 carbon atoms.

Other amino acids include for example non-genetically encoded forms of amino acids, as well as a conservative substitution of an L-amino acid. Naturally-occurring non-genetically encoded amino acids include, for example, beta-alanine, 3-amino-propionic acid, 2,3-diamino propionic acid, alpha-aminoisobutyric acid (Aib), 4-amino-butyric acid, N-methylglycine (sarcosine), hydroxyproline, ornithine (e.g., L-ornithine), citrulline, t-butylalanine, t-butylglycine, N-methylisoleucine, phenylglycine, cyclohexylalanine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, L-homoarginine (Hoarg), N-acetyl lysine, 2-amino butyric acid, 2-amino butyric acid, 2,4-diaminobutyric acid (D- or L-), p-aminophenylalanine, N-methylvaline, homocysteine, homoserine (HoSer), cysteic acid, epsilon-amino hexanoic acid, delta-amino valeric acid, or 2,3-diaminobutyric acid (D- or L-), etc. These amino acids are well known in the art of biochemistry/peptide chemistry.

The term "pharmaceutically acceptable salt," as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M. Berge et al. describe pharmaceutically acceptable salts in detail in *J Pharmaceutical Sciences* 66: 1-19, 1977. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

In an embodiment, $Xaa^1$, $Xaa^2$, $Xaa^3$, $Xaa^4$ and/or $Xaa^5$ are/is an N-amino cyclic urea residue. In an embodiment, $Xaa^1$, $Xaa^2$, $Xaa^3$, $Xaa^4$ or $Xaa^5$ is an N-amino cyclic urea residue. In a further embodiment, $Xaa^1$ is an N-amino cyclic urea residue. In another further embodiment, $Xaa^2$ is an N-amino cyclic urea residue. In another further embodiment, $Xaa^3$ is an N-amino cyclic urea residue. In another further embodiment, $Xaa^4$ is an N-amino cyclic urea residue. In another further embodiment, $Xaa^5$ is an N-amino cyclic urea residue.

In an embodiment, $Xaa^1$, $Xaa^2$, $Xaa^3$, $Xaa^4$, $Xaa^5$ and $Xaa^6$ are all L-amino acids. In another embodiment, $Xaa^1$, $Xaa^2$, $Xaa^3$, $Xaa^4$, $Xaa^5$ and $Xaa^6$ are all D-amino acids. In another embodiment, at least one of $Xaa^1$, $Xaa^2$, $Xaa^3$, $Xaa^4$, $Xaa^5$ and $Xaa^6$ is a D-amino acid. In a further embodiment, $Xaa^2$ is D-Trp and/or $Xaa^5$ is D-Phe.

In an embodiment, $Xaa^7$, $Xaa^8$, $Xaa^9$, $Xaa^{10}$, $Xaa^{11}$, $Xaa^{12}$ and/or $Xaa^{13}$ are/is an N-amino cyclic urea residue. In an embodiment, $Xaa^7$, $Xaa^8$, $Xaa^9$, $Xaa^{10}$, $Xaa^{11}$, $Xaa^{12}$ or $Xaa^{13}$ is an N-amino cyclic urea residue. In a further embodiment, $Xaa^7$ is an N-amino cyclic urea residue. In another further embodiment, $Xaa^8$ is an N-amino cyclic urea residue. In another further embodiment, $Xaa^9$ is an N-amino cyclic urea residue. In another further embodiment, $Xaa^{10}$ is an N-amino cyclic urea residue. In another further embodiment, $Xaa^{11}$ is an N-amino cyclic urea residue. In another further embodiment, $Xaa^{12}$ is an N-amino cyclic urea residue. In another further embodiment, $Xaa^{13}$ is an N-amino cyclic urea residue.

In an embodiment, $Xaa^7$, $Xaa^8$, $Xaa^9$, $Xaa^{10}$, $Xaa^{11}$, $Xaa^{12}$ and $Xaa^{13}$ are all L-amino acids. In another embodiment, at least one of $Xaa^7$, $Xaa^8$, $Xaa^9$, $Xaa^{10}$, $Xaa^{11}$, $Xaa^{12}$ and $Xaa^{13}$ is a D-amino acid. In another embodiment, $Xaa^7$, $Xaa^8$, $Xaa^9$, $Xaa^{10}$, $Xaa^{11}$, $Xaa^{12}$ and $Xaa^{13}$ are all D-amino acids.

In embodiments, $Z^1$ is H (i.e. the peptidomimetic has a "native" $NH_2$ terminal), or an amino-terminal modifying group, in an embodiment a straight chained or branched alkyl group of one to eight carbons, or an acyl group (R—CO—), wherein R is a hydrophobic moiety (e.g., acetyl, propionyl, butanyl, iso-propionyl, or iso-butanyl), or an aroyl group (Ar—CO—), wherein Ar is an aryl group. In an embodiment, the acyl group is a $C_1$-$C_{16}$ or $C_3$-$C_{16}$ acyl group (linear or branched, saturated or unsaturated), in a further embodiment, a saturated $C_1$-$C_6$ acyl group (linear or branched) or an unsaturated $C_3$-$C_6$ acyl group (linear or branched), for example an acetyl group ($CH_3$—CO—, Ac).

In embodiment, $Z^2$ is a carboxyl group (i.e., the native carboxy terminal of the peptide), or a carboxy-terminal modifying group (e.g., attached via an ester linkage), in an embodiment, an hydroxamate group, a nitrile group, an amide (primary, secondary or tertiary) group, an aliphatic amine of one to ten carbons such as methyl amine, iso-butylamine, iso-valerylamine or cyclohexylamine, an aromatic or arylalkyl amine such as aniline, napthylamine, benzylamine, cinnamylamine, or phenylethylamine, an alcohol or $CH_2OH$. In a further embodiment, $Z^2$ is an amide, more particularly $NH_2$.

The present invention includes all tautomers and stereoisomers of the peptidomimetics of sequence A or B, either in admixture or in pure or substantially pure form. The compounds of the present invention can have asymmetric centers at the carbon atoms, and therefore the peptidomimetics of sequence A or B can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

In some embodiments, a peptidomimetic of the present invention comprises one or more modifications to increase protease resistance, plasma protein binding, serum stability, intracellular penetration, and/or bioavailability, such as N- and/or C-terminal acetylation, glycosylation, attachment to proteins such as albumin, covalent attachment of fatty acids (e.g., $C_6$-$C_{18}$), biotinylation, amidation, or PEGylation, as well as substitution with D-amino acid or unnatural amino acid, and/or cyclization of the peptide.

In an embodiment, the above-mentioned peptidomimetic is substantially pure. A compound is "substantially pure" when it is separated from the components that naturally accompany it. Typically, a compound is substantially pure when it is at least 60%, more generally 75%, 80% or 85%, preferably over 90% and more preferably over 95% (96, 97, 98 or 99%), by weight, of the total material in a sample. Purity can be measured using any appropriate method such as column chromatography, gel electrophoresis, HPLC, etc.

In other aspects, the present invention provides N-amino cyclic urea containing peptidomimetics of other CD36 modulatory peptides (i.e. in which one or more amino acids are replaced with the N-amino cyclic urea residues defined above). CD36 modulatory peptides comprising aza inter-amino acid linkage (azapeptides) are described, for example, in PCT publication No. WO2008/157738 and U.S. Patent Pub. No. 20100279941. Examples of such peptides include peptides having the following sequences: (D/L)His-AzaPhe-Ala-Ala-DPhe-Lys; Ala-AzaPhe-Ala-Trp-DPhe-Lys; His-AzaTyr-Ala-Trp-DPhe-Ala; Ala-AzaTyr-Ala-Trp-DPhe-Lys; His-DTrp-AzaLeu-Trp-Ala-Lys; His-DTrp-AzaLeu-Ala-DPhe-Lys; Phe-DTrp-Ala-AzaTyr-DPhe-Lys; Ala-DTrp-Ala-AzaTyr-DPhe-Lys; Hydrocinnamyl-DTrp-Ala-AzaTyr-DPhe-Lys; Ala-DTrp-azaLeu-Trp-DPhe-Lys; Ala-DTrp-Ala-AzaPhe-DPhe-Lys; His-DTrp-AzaPro-Trp-DPhe-Lys; His-DTrp-AzaGly-Trp-DPhe-Ala; HAlC-2MeDTrp-DLys-Trp-DPhe-Lys; and ATAB-2MeDTrp-DLys-Trp-DPhe-Lys.

In other aspects, the present invention provides N-amino cyclic urea containing peptidomimetics of other IL-1R modulatory peptides (in which one or more amino acids are replaced with the N-amino cyclic urea residues defined above), such as those described in U.S. Patent Pub. No. 20060094663 and PCT publication No. WO2010/106441. Examples of such peptides are depicted in table 1 below (upper cases=L-amino acids; lower cases=D-amino acids)

TABLE 1

| Examples of peptidomimetics of IL-1R modulatory peptides | |
|---|---|
| API-101 | APRYTVELA |
| API-101.1 | AARYTVELA |
| API-101.2 | APAYTVELA |
| API-101.3 | APRATVELA |
| API-101.4 | APRYAVELA |
| API-101.5 | APRYTAELA |
| API-101.6 | APRYTVALA |
| API-101.7 | APRYTVEAA |
| API-101.9 | PRYTVELA |
| API-101.10 | RYTVELA |
| API-101.11 | YTVELA |
| API-101.12 | TVELA |
| API-101.101 | XYTVELA (X = Citrulline) |

TABLE 1-continued

Examples of peptidomimetics of IL-1R modulatory peptides

| | |
|---|---|
| API-101.102 | XYTVQLA (X = Citrulline) |
| API-101.103 | RYTVQLA |
| API-101.104 | RFTVELA |
| API-101.105 | RYSVELA |
| API-101.106 | RYVVELA |
| API-101.107 | RYTPELA |
| API-101.108 | RYTVEL |
| API-101.113 | RYTPEL |
| API-101.114 | KYTPELA |
| API-101.115 | XYTPELA (X = Ornithine) |
| API-101.116 | RWTPELA |
| API-101.117 | RYTPDLA |
| API-101.118 | RYTPQLA |
| API-101.119 | RYTPEFA |
| API-101.120 | RYTPEMA |
| API-101.121 | XRYTPELA (X = Acetyl) |
| API-101.122 | RYTPEPA |
| API-101.123 | RYTPALA |
| API-101.126 | XYTPEL (X = Ornithine) |
| API-101.127 | RFVPELA |
| API-101.128 | RWTPEL |
| API-101.129 | RYTPEV |
| API-101.132 | RFTPEL |
| API-101.133 | KYTPEL |
| API-101.134 | XYTPEL (X = Citrulline) |
| 101.135 | Rytpel |
| 101.145 | ryTpel |
| 101.146 | rytPel |
| 101.147 | rytpEl |
| 101.148 | rytpeL |
| 101.149 | rtppel |
| 101.150 | ryPpel |
| 101.151 | rypPel |
| 101.152 | ryPPel |
| 101.153 | ryxpel (x = D-pipecolate) |
| 101.154 | ryXpel (X = L-pipecolate) |
| 101.155 | rytxel (x = D-pipecolate) |
| 101.156 | rytXel (X = L-pipecolate) |
| 101.157 | rhtpel (d-amino acids |
| 101.158 | rztpel (z = D-Dopa) |
| 101.159 | r(cha)tpel (cha = D-cyclohexyalanine) |
| 101.160 | rytp(D-alpha-aminoadipic acid)l |
| 101.161 | rytpe(cha) (cha = D-cyclohexyalanine) |
| 101.162 | (HN═C(NH2)NH(CH2)4CO-)ytpel |
| 101.163 | Rytphl |

Peptides (including the peptide portions of peptidomimetics) of the present invention are obtained by any method of peptide synthesis known to those skilled in the art, including synthetic (e.g., exclusive solid phase synthesis, partial solid phase synthesis, fragment condensation, classical solution synthesis) and recombinant techniques. For example, the peptides or peptide derivatives can be obtained by solid-phase peptide synthesis, which in brief, consists of coupling the carboxyl group of the C-terminal amino acid to a resin (e.g., benzhydrylamine resin, chloromethylated resin, hydroxymethyl resin) and successively adding N-alpha protected amino acids. The protecting groups maybe any such groups known in the art. Before each new amino acid is added to the growing chain, the protecting group of the previous amino acid added to the chain is removed. Such solid phase synthesis has been described, for example, by Merrifield, 1964, J. Am. Chem. Soc. 85: 2149; Vale et al., 1981, Science, 213: 1394-1397, in U.S. Pat. Nos. 4,305,872 and 4,316,891, Bodonsky et ah, 1966, Chem. Ind. (London), 38: 1597; Pietta and Marshall, 1970, Chem. Comm. 650. The coupling of amino acids to appropriate resins is also well known in the art and has been described in U.S. Pat. No. 4,244,946. (Reviewed in Houben-Weyl, *Methods of Organic Chemistry*. Vol E22a. Synthesis of Peptides and peptidomimetics, Murray Goodman, Editor-in-Chief, Thieme. Stuttgart. New York 2002).

During any process of the preparation of a compound of the present invention, it may be desirable to protect sensitive reactive groups on any of the molecule concerned. This may be achieved by means of conventional protecting groups such as those described in Protective Groups In Organic Synthesis by T. W. Greene & P. G. M. Wuts, 1991, John Wiley and Sons, New-York; and Peptides: chemistry and Biology by Sewald and Jakubke, 2002, Wiley—VCH, Wheinheim p. 142. For example, alpha amino protecting groups include acyl type protecting groups (e.g., trifluoroacetyl, formyl, acetyl), aliphatic urethane protecting groups (e.g., t-butyloxycarbonyl (BOC), cyclohexyloxycarbonyl), aromatic urethane type protecting groups (e.g., fluorenyl-9-methoxy-carbonyl (Fmoc), benzyloxycarbonyl (Cbz), Cbz derivatives) and alkyl type protecting groups (e.g., triphenyl methyl, benzyl). The amino acids side chain protecting groups include benzyl (For Thr and Ser), Cbz (Tyr, Thr, Ser, Arg, Lys), methyl ethyl, cyclohexyl (Asp, His), Boc (Arg, His, Cys) etc. The protecting groups may be removed at a convenient subsequent stage using methods known in the art.

Purification of the synthesized peptide or peptide derivatives is carried out by standard methods, including chromatography (e.g., ion exchange, size exclusion, affinity), centrifugation, precipitation or any standard technique for the purification of peptides and peptide derivatives. In one embodiment, thin-layered chromatography is employed. In another embodiment, reverse phase HPLC is employed. Other purification techniques well known in the art and suitable for peptide isolation and purification may be used in the present invention.

Where the processes for the preparation of the compounds according to the present invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques such as the formation of diastereoisomeric pairs by salt formation with an optically active acid followed by fractional crystallization and regeneration of the free base. The compounds may also be resolved by formation of diastereomeric esters or amides, followed by removal of the chiral auxiliary. Alternatively, the compounds may be resolved using chiral HPLC column.

Various methods can be used to introduce aza and lactam residues into the peptides described herein. In some embodiments, systematic scans of a peptide described herein with lactam can be used. Various synthetic strategies for the synthesis of amino γ-lactam (Agl) peptide mimics are known in the art and can be used for the present invention. See, for example, Toniolo, C. Int. J. Pept. Protein Res. 1990, 55, 287, and references therein; Wolf, J.-P.; Rapoport, H. J. Org. Chem. 1989, 54, 3164. Schuster, M.; Blechert, S. Angew. Chem. Int. Ed. 1997, 36, 2036. Wolfe, M. S.; Dutta, D.; Aube, J. J. Org. Chem. 1997, 62, 654. (b) Nóth, J.; Frankowski, K. J.; Neuenwander, B.; Aube, J. J. Comb. Chem. 2008, 10, 456; Piscopio, A. P. D.; Miller J. F.; Koch K. Tetrahedron Letters. 1998, 39, 2667; Armstrong, S. K. J. Chem. Soc, Perkin Trans. 1 1998, 1, 371; Piscopio, A. D.; Miller, J. F.; Koch K. Tetrahedron 1999, 55, 8189; Galaud, F.; Lubell, W. D. Biopolymers (Peptide Science) 2005, 80, 665; Bhooma, R.; Rodney, J. J. Org. Chem. 2006, 71, 2151; St.-Cyr, D.; Jamieson, A. G.; Lubell, W. D. Org. Lett. 2010, 12 (8), 1652-1655; Boutard, N. Jamieson, A. G. Ong, H. Lubell, W. D., Chemical Biology and Drug Design 2010, 75 (1), 40-50; Jamieson, A. G. Boutard, N., Beauregard, K., Bodas, M. B, Ong, H., Quiniou, C., Chemtob, S., Lubell, W. D., J. Am. Chem. Soc. 2009, 131, 7917-7927; and PCT publications Nos. WO2010/106441 and WO2010/105367. Various synthetic strategies for the synthesis of azapeptides are known in the art and can be used for the present invention. See, for example, PCT publication No. WO 2008/154738; Sabatino et al. Org. Lett. 2009 Aug. 20; 11(16): 3650-3; Sabatino et al., J Am Chem. Soc. 2011 Aug. 17; 133(32):12493-506, Epub 2011 Jul. 21; Proulx, C.; Sabatino, D.; Hopewell, R.; Spiegel, J.; Garcia Ramos, Y.; Lubell, W. D. *Future Med. Chem.* 2011, 3, 1139-1164; Yesica Garcia-Ramos, Caroline Proulx, William D. Lubell, *Canadian Journal of Chemistry,* 2012, 90(11): 985-993). The N-amino cyclic urea comprising peptidomimetics described herein may be synthesized, for example, using the methods described below.

In another aspect, the present invention provides a pharmaceutical composition comprising the above-mentioned peptidomimetics and one or more pharmaceutically acceptable carriers, diluents and/or excipients. Such compositions may be prepared in a manner well known in pharmaceutical art. Supplementary active compounds can also be incorporated into the compositions. As used herein "pharmaceutically acceptable carrier", "diluent" or "excipient" includes any and all solvents, buffers, dispersion media, coatings, anti-bacterial and antifungal agents, isotonic and absorption delaying agents, and the like that are physiologically compatible. The carrier can be suitable, for example, for oral, intravenous, parenteral, topical, intradermal, subcutaneous, intramuscular, intracranial, intraorbital, subconjunctival, ophthalmic, intraventricular, intracapsular, intraspinal, intrathecal, epidural, intracisternal, intraperitoneal, intranasal, intrauterine, intramyometrial, sublingual, vaginal, rectal, epidural or pulmonary (e.g., aerosol) administration (see Remington: The Science and Practice of Pharmacy by Alfonso R. Gennaro, 2003, 21th edition, Mack Publishing Company).

Compositions within the scope of the present invention should contain the active agent (e.g. peptidomimetic of sequence A or B) in an amount effective to achieve the desired therapeutic effect while minimizing adverse side effects. Pharmaceutically acceptable preparations and salts of the active agent are within the scope of the present invention and are well known in the art. For the administration of peptidomimetics and the like, the amount administered should be chosen so as to minimize adverse side effects. The amount of the therapeutic or pharmaceutical composition which is effective in the treatment of a particular disease, disorder or condition will depend on the nature and severity of the disease, the target site of action, the patient's weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 100 mg/kg/day will be administered to the subject. Effective doses may be extrapolated from dose response curves derived from in vitro or animal model test systems. For example, in order to obtain an effective mg/kg dose for humans based on data generated from rat studies, the effective mg/kg dosage in rat is divided by six.

In embodiments, the peptidomimetics of sequence A have the ability to modulate (e.g., inhibit or activate) CD36 activity (CD36 modulators).

As used herein, the term "modulator" refers to a compound that alters or elicits an activity. For example, the presence of a modulator may result in an increase or decrease in the magnitude of a certain activity compared to the magnitude of the activity in the absence of the modulator. In certain embodiments, a modulator is an inhibitor or antagonist, which decreases the magnitude of one or more activities. In certain embodiments, an inhibitor completely prevents one or more biological activities. In certain embodiments, a modulator is an activator or agonist, which increases the magnitude of at least one activity. In certain embodiments the presence of a modulator results in an activity that does not occur in the absence of the modulator. As used herein, the terms "inhibiting," "reducing," "preventing," or "antagonizing," or any variations of these terms as used herein, refer to a measurable decrease of a biological activity. In some embodiments, the decrease is a 10%, 15%, 20%, 30%, 40%, 50%, 60%, 70%, 80%, 90%, or 95% reduction in the biological activity relative to a control. As used herein, the terms "stimulating," "increasing," or "agonizing," or any variations of these terms as used herein, refer to a measurable increase of a biological activity. In some embodiments, the increase is a 10%, 15%, 20%, 30%, 40%, 50%, 60%, 70%, 80%, 90%, or 95% increase in the biological activity relative to a control.

CD36, also known as FAT, SCARB3, GP88, glycoprotein IV (gpIV) and glycoprotein IIIb (gpIIIb), is an integral membrane protein found on the surface of many cell types in vertebrate animals. CD36 is a member of the class B scavenger receptor family of cell surface proteins. CD36 has been shown to bind many ligands including collagen, thrombospondin, erythrocytes parasitized with *Plasmodium falciparum*, oxidized low density lipoproteins, native lipoproteins, oxidized phospholipids, and long-chain fatty acids.

Accordingly, the present invention relates to a method for modulating (e.g., inhibiting or activating) CD36 activity through its interaction with the peptidomimetics of sequence A of the present invention. In view of the importance of CD36 in numerous pathways and conditions in animals, the peptidomimetics of sequence A of the present invention are useful in the treatment of CD36-related diseases, disorders or conditions. The present invention relates to a method for inhibiting or antagonizing CD36 activity through its interaction with the peptidomimetics of sequence A of the present invention.

Examples of diseases and conditions associated with CD36 activity include, but are not limited to atherosclerosis, inflammation (TLR2-related inflammation), abnormal angiogenesis, age-related macular degeneration (dry and/or wet forms), abnormal lipid metabolism, abnormal removal of apoptotic cells, ischemia such as cerebral ischemia and myocardial ischemia, ischemia-reperfusion injury, ureteral obstruction, fibrinogenesis in chronic kidney diseases, stroke, Alzheimer's Disease, diabetes, diabetic nephropathy and obesity.

In another aspect, the present invention provides a method for reducing or inhibiting TLR2-related inflammation in a biological system (cells, subject), said method comprising contacting said biological system with a peptidomimetic of sequence A as defined herein. In another aspect, the present invention provides a method for reducing or inhibiting the production of nitric oxide (NO) induced by TLR2 activation/stimulation in a cell, said method comprising contacting said cell with a peptidomimetic of sequence A as defined herein. The present invention also relates to the treatment of medical conditions involving the activation of TLR2, and especially immune-mediated and inflammatory diseases. TLR2 has also been implicated to have a role in a wide variety of allergic- and immune-mediated inflammatory diseases such as sepsis, ischemia/reperfusion injury to heart or kidneys, cardiovascular disease and atherosclerosis, allergies, asthma, atopy, atopic dermatitis, arthritis (rheumatoid arthritis), systemic lupus erymathosis (SLE), and diabetes. (O'Neill et al., 2009, *Pharmacol. Rev.*, vol. 61, p. 177).

In an embodiment, the CD36-related disease, disorder or condition is atherosclerosis, age-related macular degeneration, fibrinogenesis in chronic kidney diseases or myocardial ischemia/reperfusion injury.

In embodiments, the peptidomimetics of sequence B have the ability to modulate (e.g., inhibit or activate) IL-1 receptor activity (IL-1R modulator). The interleukin-1 (IL-1) family of polypeptide hormones represents an important class of cytokines which are expressed by a variety of cell types including monocytes (which are the predominant source of IL-1), fibroblasts, endothelial cells, smooth muscle cells, osteoclasts, astrocytes, epithelial cells, T-cells, B-cells and numerous cancer cells. This family of cytokines includes more than 7 distinct but structurally related molecules including IL-1α and IL-1β. Receptors for IL-1 recognize both α and β forms and both forms have similar biological properties. The biological properties of IL-1 are numerous and include mediating many immunological and inflammatory responses to infection and injury.

Two distinct receptor proteins of IL-1 have been cloned and characterized: IL-1RI, which generates the biological effects of IL-1; and IL-1RII. In addition, a receptor accessory protein (IL-IRAcP), which is the putative signal-transducing subunit of the receptor complex, has been identified. Generally, one of the first events in signal transduction, following IL-1 binding, is the formation of an IL-1R/IL-1RacP complex which leads to IRAK (IL-1 receptor associated kinase) recruitment to the complex and to a cascade of phosphorylation by kinases, causing the activation of transcriptional factors including NFKB and AP-I. The IL-1R/IL-1RacP complex can also recruit and activate kinases like PBK and Akt and can also lead to the activation of the PLC/PKC pathway of signalization.

Despite its normally beneficial effects on an organism response to infection and injury, actions of IL-1 can be harmful in some instances. For example, inappropriate production or response to IL-1 have been shown in many acute and chronic inflammatory diseases such as rheumatoid arthritis, inflammatory bowel disease (IBD, such as Crohn's disease or ulcerative colitis), osteoarthritis, psoriasis, septic shock, encephalitis and respiratory distress syndrome. IL-1 has also been shown to play a role in several other illnesses including Alzheimer's disease, periventricular leukomalacia, meningitis, stroke, and a number of autoimmune diseases.

Generally, Interleukin-1 (IL-1) plays a role in the regulation of inflammation by stimulating generation of inflammatory mediators like IL-6, prostaglandin $E_2$ ($PGE_2$; via the induction the COX-2 and PGE synthase (mPGES) expression) and itself, therefore enhancing the process of inflammation. Another biological activity of IL-1 is to induce proliferation and activation of numerous cell types like T-cells (Cullinan, et al. 1998; Dunne and O'Neill 2003). IL-1 may also increase the level of collagenase in an arthritic joint and has been implicated in the acute and chronic stages of immunopathology in rheumatoid arthritis. IL-1 may be responsible for altering endothelial cell function, directing the chemotaxis of lymphocytes and leucocytes into synovial tissue and inducing the secretion of latent collagenase by chondrocytes and fibroblasts. IL-1 is considered, along with TNF, as the prototype of inflammatory cytokines. However, the effects of IL-1 are not limited to inflammation and this cytokine also plays a role in bone formation and remodeling, insulin secretion and fever induction.

As a major pro-inflammatory cytokine, IL-1 is a potentially powerful target for therapeutic intervention in diseases like articular cartilage injury such as in arthritis. Osteoarthritis and rheumatoid arthritis are only second to heart disease for causing work disabilities in North America and their prevalence increase dramatically with age.

Current approaches for treating IL-1 related diseases include the development of soluble receptors, monoclonal antibodies, mimetics of cytokines, antisense techniques and kinase inhibitors. Short peptides known as Allosteramers™ that specifically target the IL-1 receptor activity have been developed. See, U.S. Pat. No. 7,432,341, and U.S. Pub. No. 20060094663 and PCT publication No. WO2010/106441.

Accordingly, the present invention relates to a method for modulating (e.g., inhibiting or activating) IL-1 receptor activity through its interaction with the peptidomimetics of sequence B of the present invention. In view of the importance of IL-1 and or IL-1R/IL-1RacP receptor function in numerous pathways and conditions in animals, the peptidomimetics of sequence B of the present invention are useful in the treatment of IL-1-related diseases, disorders or conditions.

Therefore, methods of the present invention comprise administering to a subject in need thereof or at risk of being in need thereof an effective amount of a peptidomimetic of sequence B, or a composition comprising such peptidomimetic, to a subject, to modulate (e.g., inhibit) IL-1R/RacP biological activity. In one embodiment, an effective amount of a therapeutic composition comprising a peptidomimetic of sequence B and a suitable pharmaceutical carrier is administered to a subject to inhibit IL-1R/IL-1RacP biological activity to prevent, ameliorate symptoms or treat a disorder, disease or condition related to abnormal signaling through IL-1R/IL-1RacP (e.g., overstimulation of the IL-1R/IL-1RacP receptor via an overproduction of IL-1/IL-1RacP ligand or via a constitutively active receptor or any other defect). In one embodiment, the subject is an animal. In another embodiment, the subject is a mammal, and preferably a human.

The peptidomimetics of sequence B of the present invention are used in the treatment, prophylaxis or amelioration of symptoms in any disease condition or disorder where the inhibition of IL-1R/IL-1RacP biological activity might be beneficial. Diseases, conditions or disorders to which the peptidomimetics of sequence B of the present invention may be beneficial include, but are not limited to the following examples: chronic and acute inflammation diseases like rheumatoid arthritis, inflammatory bowel disease, septic shock, osteoarthritis, psoriasis, encephalitis, glomerulonephritis, respiratory distress syndrome and Reiter's syndrome. Other conditions include, systemic lupus erythematosus, scleroderma, Crohn's disease, ulcerative colitis, inflammatory joint disease, cachexia in certain leukemias, Alzheimer's disease, numerous types of cancers, diabetes mellitus (type I), pulmonary hypertension, stroke, periventricular leucopenia and meningitis.

The present invention can also be used to treat other inflammatory diseases, disorders and conditions including, but not limited to, CNS demyelinating diseases, multiple sclerosis, acute disseminated encephalomyelitis (ADEM), idiopathic inflammatory demyelinating disease, transverse myelitis, Devic's disease, progressive multifocal leukoencephaly, Guillain-Barre syndrome, chronic inflammatory demyelinating polyneuropathy, anti-MAG neuropathy, inflammatory bowel disease, sepsis, septic shock, adult respiratory distress syndrome, pancreatitis, trauma-induced shock, asthma, bronchial asthma, allergic rhinitis, cystic fibrosis, stroke, acute bronchitis, chronic bronchitis, acute bronchiolitis, chronic bronchiolitis, gout, spondylarthropathris, ankylosing spondylitis, Reiter's syndrome, psoriatic arthropathy, enterapathric spondylitis, juvenile arthropathy or juvenile ankylosing spondylitis, reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes," polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein purpura, hypertrophic osteoarthropathy, multicentric reticulohistiocytosis, arthritis associated with certain diseases, surcoilosis, hemochromatosis, sickle cell disease and other hemoglobinopathies, hyperlipoproteineimia, hypogammaglobulinemia, hyperparathyroidism, acromegaly, familial Mediterranean fever, Behat's Disease, systemic lupus erythrematosis, and relapsing polychondritis, inflammatory conditions resulting from harmful stimuli, such as pathogens, damaged cells, or irritants, sarcoidosis, disseminated intravascular coagulation, atherosclerosis, Kawasaki's disease, macrophage activation syndrome (MAS), HIV, graft-versus-host disease, Sjogren's syndrome, vasculitis, autoimmune thyroiditis, dermatitis, atopic dermatitis, myasthenia gravis, inflammatory conditions of the skin, cardiovascular system, nervous system, liver, kidney and pancreas, cirrhosis, eosinophilic esophagitis, cardiovascular disorders, disorders associated with wound healing, respiratory disorders, chronic obstructive pulmonary disease, emphysema, acute inflammatory conditions, atopic inflammatory disorders, bacterial, viral, fungal or protozoan infections, pulmonary diseases, systemic inflammatory response syndrome (SIRS), hemophagocytic lymphohistiocytosis (HLH), juvenile rheumatoid arthritis, osteoarthritis, psoriatic arthritis, lupus nephritis, lupus-associated arthritis, ankylosing spondylitis, autoimmune diseases and related diseases or conditions.

The peptidomimetics (IL-1R/IL-1RacP antagonists or agonists) of sequence B of the present invention may be administered alone or in combination (concurrently or sequentially) with other active agents useful for the treatment, prophylaxis or amelioration of symptoms of an IL-1, IL-1R/IL-1RacP associated disease or condition. Thus, the compositions and methods of the present invention can be used in combination with other agents exhibiting the ability to modulate IL-1 activity (e.g., synthesis, release and/or binding to IL-1R/IL-1RacP) or to reduce the symptoms of an IL-1-associated disease (e.g., rheumatoid arthritis and inflammatory bowel disease). Example of such agents include but are not limited to antirheumatic drugs such as chloroquine, auranofm (Ridaura™), dexamethasone, sodium aurothiomalate, methotrexate, probucol, pentoxyfylline, disulfuram, antioxidants such as nordihydroguaiaretic acid, IL-1 Trap (see e.g., 2003, Curr. Opin. Inv. Drugs, 4(5): 593-597), Anakinra (Kineret™, PCT Application WO00236152), leflunomide, corticosteroids (Medrol™, Deltasone™, Orasone™) as well as other agents such as those described in Bender and Lee (1989) Annual Reports in Medicinal Chemistry, chapter 20: Pharmacological Modulation of IL-1: 185-193). Other drugs may also be used in combination with the compounds of the present invention like anti-inflammatory drugs such as Non-Steroidal Antiinflammatory Drugs (NSAIDS, e.g., Rofecoxib (VIOXX™), Celecoxib (Celebrex™), Valdecoxib (Bextra™), Aspirin™ Advil™), anti-TNF-α drugs (Infliximab, etanercept, adalimumab), collagenase inhibitors and others. Of course a combination of two or more peptidomimetics of sequence B and their combination with one or more drug can also be used, in all combinations.

DESCRIPTION OF ILLUSTRATIVE EMBODIMENTS

The present invention is illustrated in further details by the following non-limiting examples.

Example 1

Preparation of N-Amino-imidazolin-2-one Peptide Mimics

Experimental Procedures
General:
Unless specified, all non-aqueous reactions were run under an inert atmosphere (argon).

All glassware was stored in the oven or flame-dried and let cool under an inert atmosphere prior to use. Anhydrous solvents were obtained either by filtration through drying columns (THF, $Et_2O$, $CH_2Cl_2$, DMF, $CH_3CN$, toluene) on a GlassContour® system (Irvine, Calif.), by distillation over potassium hydroxide (diisopropylamine, N,N-diisopropylethyl amine), or by distillation over sodium/benzophenone (dioxane). Analytical thin-layer chromatography (TLC) was performed on glass-backed silica gel plates (Merck® 60 F254). Visualization of the developed chromatogram was performed by UV absorbance or staining with Ceric Ammonium Molybdate. Silica gel chromatography was performed using 230-400 mesh silica (Silicycle). Melting points were obtained on a Buchi melting point apparatus and are uncorrected. Infrared spectra were taken on a Perkin Elmer® Spectrum One FTIR instrument and are reported in reciprocal centimeters ($cm^{-1}$). Nuclear magnetic resonance spectra ($^1H$, $^{13}C$, COSY) were recorded either on a Bruker® AV 300, AMX 300, AV 400, AMX 400, or DMX 700 spectrometer. Optical rotations were determined with a Perkin-Elmer® 341 polarimeter at 589 or 546 nm. Data are reported as follows: $[\alpha]\lambda$temp, concentration (c in g/100 mL), and solvent. High resolution mass spectra were performed by the Centre régional de spectroscopie de masse de l'Université de Montréal. Analytical SFC were performed at the Laboratoire d'analyse et de séparation chirale par SFC de l'Université de Montréal and data are reported as follows: column type, eluent, flow rate, temperature, backpressure, wavelength and retention times (tr).

Reagents:
Propargyl bromide was purchased from Sigma-Aldrich® and filtered on a silica plug prior to use. All aryl iodides used in the Sonogashira reactions were commercially available from Sigma-Aldrich® and filtered on a silica plug prior to use, except 4-(OTBDMS)-iodobenzene, N-Boc-3-iodoindole (Wiltulski, B.; Buschmann, N.; Bergsträber, U. Tetrahedron 2000, 56, 8473), and Trt-4-iodoimidazole (Cliff, M. D.; Pyne, S. G. Synthesis 1994, 681), which were prepared according to literature procedures. Copper iodide was purchased from Sigma-Aldrich® and purified by dissolving in a boiling saturated solution of aqueous NaI, followed by dilution with water, filtering and washing (Armarego, W. L. F.; Perrin, D. D.; Purification of Laboratory Chemicals, Butterworth-Heinemann, 1996, p. 381). Benzophenone hydrazone, p-nitrophenylchloroformate, potassium tert-butoxide, sodium hydride, N-methylmorpholine, isobutyl chloroformate, hydroxylamine hydrochloride, pyridine, Pd(PPh$_3$)$_2$Cl$_2$, all were purchased from Sigma-Aldrich®, Alfa Aesar®, or Strem Chemicals® and used without further purification. The amino acids, Fmoc-His(Trt), Fmoc-D-Trp(Boc), Fmoc-Ala, Fmoc-D-Phe, Fmoc-Lys(Boc), and H-D-Phe-OtBu, and coupling reagents such as HBTU, all were purchased from GL Biochem® and used as received.

Fmoc-Based Solid-Phase Peptide Synthesis:

Polystyrene Rink Amide resin (0.64 mmol/g, 75-100 mesh) was purchased from Advanced Chemtech®. Loading of the resin was determined by elemental analysis and standard Fmoc loading test (Novabiochem catalog, 3: Peptide synthesis protocols, EMD Biosciences, 2006-2007, p. 3.4). Solid-phase chemistry was performed in filtration tubes equipped with caps and stopcocks purchased from SUPELCO®. Analytical LCMS and HPLC analyses were performed on a 5 µM, 150 or 50 mm×4.6 mm C18 Phenomenex Gemini® column with a flow rate of 0.5 mL/min using respectively a 0-80% or 0-40% gradient from pure water [0.1% formic acid (FA)] to mixtures with CH$_3$CN (0.1% FA) or MeOH (0.1% FA). Peptides were purified on a semi-preparative column (5 µM, 250 mm×21.2 mm, C18 Gemini® column) using respectively a 2-40% or 2-80% gradient from pure water (0.1% FA) to mixtures with MeOH (0.1% FA) at a flow rate of 10.6 mL/min.

Fmoc Deprotection and HBTU Couplings:

Peptide syntheses were performed under standard conditions (Lubell, W. D.; Blankenship, J. W.; Fridkin, G.; Kaul, R. *Peptides. Science of Synthesis* 21.11, *Chemistry of Amides*; Thieme: Stuttgart, Germany, 2005; pp 713-809) on an automated shaker using polystyrene Rink amide resin (0.64 mmol/g, 75-100 mesh). Couplings of amino acids (3 equiv) were performed in DMF using HBTU (3 equiv) as coupling reagent and DIEA (6 equiv). Fmoc deprotections were performed by treating the resin twice with 20% piperidine in DMF for 30 min. Resin was washed after each coupling and deprotection step sequentially with DMF (3×10 mL), MeOH (3×10 mL), and DCM (3×10 mL). The purity of peptide fragments was ascertained by LCMS analysis after cleavage and deprotection of a small aliquot of resin.

Representative Protocol for Deprotection of Semicarbazone on Solid Support:

(Sabatino, D.; Proulx, C.; Klocek, S.; Bourguet, C. B.; Boeglin, D.; Ong, H.; Lubell, W. D *Org. Lett.* 2009, 11, 3650). Resin-bound semicarbazone 29a (200 mg, 0.128 mmoles) was treated with a solution of 1.5 M NH$_2$OH.HCl in pyridine (5 mL) and heated with sonication at 60° C. for 12 h. The resin was filtered and washed using aspirator suction with 10% DIEA in DMF (3×10 mL), DMF (3×10 mL), MeOH (3×10 mL), THF (3×10 mL), and DCM (3×10 mL). The extent of reaction conversion was monitored on an aliquot (3 mg) of resin, which was subjected to 1 mL of TFA/TES/H$_2$O (95:2.5:2.5, v/v/v) for resin cleavage, filtered, evaporated to a residue and analyzed by LCMS. The procedure was repeated, when LCMS analysis revealed incomplete deprotection.

CD Spectroscopy:

All CD spectra were recorded on a Chirascan® CD Spectrometer (Applied Photophysics, Leatherhead, United Kingdom) using a 1.0 cm path-length quartz cell containing 20 µM of peptide dissolved in Milli-Q® water. The experimental settings were: 1 nm, bandwidth; 0.5 nm, step size; 3 sec, sampling time.

SPR Spectroscopy:

The affinity of the small peptide ligand binding to a recombinant soluble His-tagged CD36 functionalized surface was screened by SPR sensing as previously described (Bolduc, O. R.; Lambert-Lanteigne, P.; Colin, D. Y.; Zhao, S. S.; Proulx, C.; Boeglin, D.; Lubell, W. D.; Pelletier, J. N.; Féthière, J.; Ong, H.; Masson, J.-F. *Analyst.* 2011, 136, 3142-3148). Briefly, the SPR sensors were prepared by immobilizing the His-tagged CD36 to 3-mercaptopropionyl-leucinyl-histidinyl-aspartyl-leucinyl-histidinyl-aspartic acid (3-Mpa-LHDLHD) with Nα,Nα-bis(carboxymethyl)-L-lysine at the C-terminus, a modified peptide monolayer competent to bind His-tagged biomolecules. A calibration curve of the SPR response for ligand concentrations ranging from 100 nM to 30 µM was fitted to the Langmuir isotherm (Equation 1) to determine K (K=1/K$_d$) for the CD36-ligand system.

$$\Delta\lambda_{SPR}=(K[ligand])\Delta\lambda_{SPRmax}(1+K[ligand])^{-1} \quad (1)$$

JNK Assay:

RAW264.7 murine macrophage cells (American Type Culture Collection, Manassas, Va.) pre-treated with N-aminoimidazolin-2-one peptide for 2 h at concentration varying from 10$^{-9}$ to 10$^{-6}$ M were stimulated with 10 µg/mL POVPC (Cayman chemical, Ann Arbor, Mich.) for 30 min at 37° C. Cells were lysed on ice and centrifuged at 12,000×g. Aliquots of the resulting supernatant (30 µg of protein) were analyzed on SDS-PAGE and electrotransferred on nitrocellulose membrane. The revelation was performed by incubating the membrane with primary antibody against phospho-JNK or total-JNK (Cell signalling, Pickering, Canada) (1:500) overnight and with secondary HRP-conjugated goat anti-rabbit IgG antibody (Jackson Immunoresearch Laboratories Inc., West Grove, Pa.) (1:10,000) for 1 h. Membrane was visualized by chemiluminescence and intensity of bands was measured with Image Quant software (Molecular Dynamics, Sunnyvale, Calif.). The ratio of phospho-JNK/total-JNK was used to determine the phosphorylation state of JNK modulated by the tested peptide.

Synthetic Experimental Procedures and Characterization Data

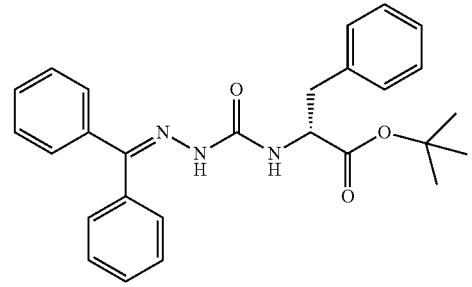 [SMILES: CC(C)(C)OC(=O)[C@@H](Cc1ccccc1)NC(=O)NN=C(c1ccccc1)c1ccccc1]

Benzhydrylidene aza-glycinyl-D-phenylalanine tert-butyl ester (D-7). A solution of p-nitrophenylchloroformate (4 g, 22.4 mmol) in 150 mL of dry dichloromethane at 0° C. was treated dropwise with a cooled 0° C. solution of benzophenone hydrazone (4 g, 20.4 mmol) in 150 mL of dry dichloromethane. The ice bath was removed. The mixture was allowed to warm to room temperature. After one hour, the solution was cooled to 0° C., treated with a solution of D-phenylalanine tert-butyl ester hydrochloride (5.8 g, 22.4 mmol) and DIEA (7.1 mL, 40.8 mmol) in dry dichloromethane (50 mL), stirred overnight, and concentrated under vacuum to a residue, which was purified by chromatography using 30% Et$_2$O in petroleum ether as eluent. Evaporation of the collected fractions gave a yellow oil (5.86 g, 65%): R$_f$ 0.31 (8:2 Et$_2$O: petroleum ether); [α]$_D^{20}$ −17.1 (c 1.04, CHCl$_3$); $^1$H NMR (400 MHz, CDCl$_3$) δ 1.48 (9H, s), 3.17-3.30 (2H, m), 4.77-4.82 (1H, m), 6.80-6.91 (1H, m), 7.24-7.67 (15H, m), 8.08 (1H, d, J=9.2 Hz). $^{13}$C NMR (100 MHz, CDCl$_3$) δ 170.5, 162.9, 154.7, 148.4, 136.4, 135.8, 131.2, 129.5, 129.4, 129.2, 128.2, 128.0, 127.0, 126.9, 126.7, 125.7, 115.2, 81.9, 53.6, 38.3, 27.6. HRMS m/z 444.2292, (M+H)+ calcd for [C27H30N3O3]+: 444.2282. IR (neat) 1675, 1590, 1513, 1445, 1367, 1335, 1288, 1151, 1110, 847, 752, 694.

Benzhydrylidene Aza-glycinyl-L-phenylalanine tert-Butyl Ester (L-7)

In a flame dried round-bottom flask, a solution of N,N'-disuccinimidyl carbonate (DSC, 7.18 g, 28.03 mmol, 1.1 eq) in dry CH2Cl2 (80 mL) and DMF (15 mL) was cooled to 0° C., and treated drop-wise by cannula with a 0° C. solution of benzophenone hydrazone (5 g, 25.5 mmol, 1 eq) in dry CH2Cl2 (112 mL). The ice-bath was removed. The reaction mixture was allowed to warm to room temperature, with stirring for 1 h, cooled to 0° C., and treated drop-wise by cannula with a premixed 0° C. solution of L-Phe-Ot-Bu*HCl (6.57 g, 25.48 mmol, 1 eq) and DIEA (8.4 mL, 50.96 mmol, 2 eq) in CH2Cl2 (32 mL). The ice-bath was removed. The reaction mixture was allowed to warm to room temperature and stirred for 16 h. The volatiles were evaporated and the residue was purified on a column of silica gel using flash chromatography with 10-50% EtOAc in hexane as solvent system. Ester L-7 was obtained as oil (8.60 g, 76% yield): $[\alpha]_D^{20}$ 14.2 (c 1.02, CHCl3); spectroscopic properties of L-7 were identical to those reported above for D-7.

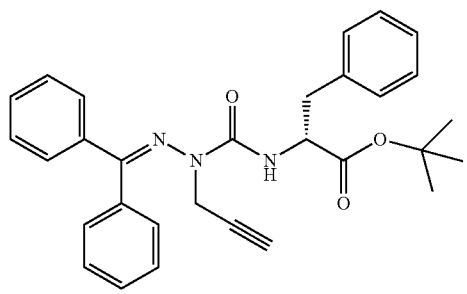 [SMILES: C#CCN(N=C(c1ccccc1)c1ccccc1)C(=O)N[C@H](Cc1ccccc1)C(=O)OC(C)(C)C]

Benzhydrylidene Aza-propargylglycinyl-D-phenylalanine tert-butyl ester (D-1)

Benzhydrylidene aza-Gly-Phe-OtBu (7, 4.05 g, 9.14 mmol) was dissolved in 40 ml of anhydrous THF, cooled to 0° C., treated with 0.95 eq. of tBuOK (99.2% pure, 974 mg, 8.68 mmol), stirred for 1 h, and treated dropwise with 1.2 eq. of propargyl bromide (1.2 mL, 10.97 mmol). The ice bath was removed. The reaction was allowed to warm to room temperature and stirred overnight. After evaporation of the volatiles under reduced pressure, the residue was purified by chromatography on silica gel using 15% EtOAc in hexanes as eluent. Evaporation of the collected fractions gave the propargyl semicarbazone D-1 as a yellow oil (3.35 g, 76%): $R_f$ 0.62 (1:1 EtOAc:hexanes); $[\alpha]_D^{20}$ 2.1 (c 0.93, CHCl3); 1H NMR (400 MHz, CDCl3) δ 1.44 (9H, s), 2.08-2.10 (1H, m), 3.20 (2H, d, J=5.9 Hz), 3.92 (1H, dd, J=2.2, 17.8 Hz), 4.21 (1H, dd, J=2.2, 18.0 Hz), 4.75-4.80 (1H, m), 7.10 (1H, d, J=8.1 Hz), 7.26-7.48 (15H, m). 13C NMR (100 MHz, CDCl3) δ170.4, 157.6, 157.4, 138.1, 136.1, 135.1, 129.7, 129.3, 128.8, 128.3, 128.2, 128.0, 127.7, 126.4, 81.5, 78.3, 71.5, 54.6, 38.1, 34.7, 27.6. HRMS m/z 482.2449, (M+H)+ calcd for [C30H32N3O3]+: 482.2438. IR (neat) 1733, 1671, 1501, 1444, 1361, 1150, 1095, 928, 843, 767, 738, 693. The degree of racemization (enantiomeric excess, 67%) was determined by SFC analysis on a chiral stationary phase [Chiralcel AD-H 25 cm, 15% i-PrOH, 3 mL/min, 35° C., 150 bar, $t_r$ (minor) 3.27 min, $t_r$ (major) 5.12 min].

Benzhydrylidene Aza-propargylglycinyl-L-phenylalanine tert-Butyl Ester (L-1)

A solution of benzhydrylidene aza-glycinyl-L-phenylalanine t-butyl ester (1, 8.60 g, 19.4 mmol, 1 eq) in THF (110 mL) at 0° C. was treated with 40% tetraethylammonium hydroxide in H2O (14.3 mL, 38.8 mmol, 2 eq), stirred 30 min, treated with 80% propargyl bromide in toluene (5.8 mL, 38.8 mmol, 2 eq), heated to 60° C. using microwave irradiation in a 300 MW Biotage apparatus on the high absorption level with automated temperature monitoring for 3 h, cooled to room temperature. The reaction volume was reduced by evaporation on a rotary evaporator, treated with CH2Cl2 (100 mL), washed three times with H2O, dried and evaporated to a residue, which was purified by flash chromatography eluting with 1:9 EtOAc/hexane. Evaporation of the collected fractions gave ester L-1 as oil (9.3 g, 99% yield): $[\alpha]_D^{20}$ −1.8 (c 1.24, CHCl3); the spectroscopic properties of L-1 were identical to those reported above for D-1. The degree of racemization (enantiomeric excess, 98.9%) was determined by SFC analysis on a chiral stationary phase [Chiralcel AD-H 25 cm, 15% i-PrOH, 3 mL/min, 35° C., 150 bar, $t_r$ (major) 3.33 min, $t_r$ (minor) 5.29 min].

Representative Procedure for the NaH-Promoted Cyclization:

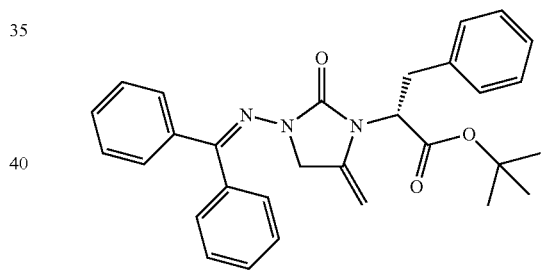

(2'R)-1-((Diphenylmethylene)amino)-3-(tert-butyl-3'-phenyl-2'-propanoate)-4-methylene-imidazolidin-2-one (D-2)

A solution of benzhydrylidene aza-propargylglycinyl-D-phenylalanine tert-butyl ester (1, 50 mg, 0.104 mmol) in 1 mL of anhydrous acetonitrile was treated with a suspension of NaH (60% in oil, 10.4 mg, 0.260 mmol). After 2 h, a small volume of water was added to the mixture, which was stirred for 15 min. The volume was concentrated, and partitioned between EtOAc and brine. The aqueous layer was separated and extracted three times with EtOAc. The combined organic layers were dried over Na2SO4, filtered, and evaporated to a residue, which was purified by silica gel chromatography using 30% Et2O in petroleum ether to give 2 as a bright yellow oil (42.2 mg, 84%): $R_f$ 0.47 (6:4 petroleum ether:Et2O); $[\alpha]_D^{20}$ 4.3 (c 0.83, CHCl3); 1H NMR (400 MHz, CDCl3) δ 1.47 (9H, s), 3.28-3.42 (2H, m), 3.46-3.56 (2H, m), 3.89-3.91 (1H, m), 4.04-4.06 (1H, m), 4.96 (1H, q, J=5.7, 10.3 Hz), 7.21-7.56 (15H, m). 13C NMR (100 MHz, CDCl3) δ 168.8, 158.9, 157.4, 138.5, 138.4, 137.7, 136.2, 130.3, 129.8, 129.5, 129.0, 128.4, 127.0, 82.8, 82.7, 77.7, 56.6, 51.4, 33.6, 28.3. Conversion into 3 occurred by double bond migration inside the ring on letting D-2 stand overnight.

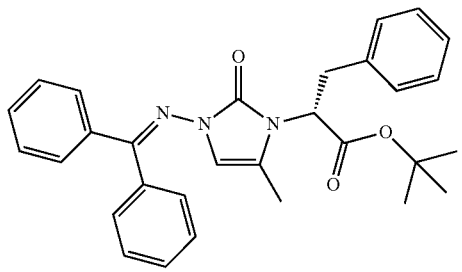 [SMILES: Cc1cn(N=C(c2ccccc2)c2ccccc2)c(=O)n1[C@H](Cc1ccccc1)C(=O)OC(C)(C)C]

(2'R)-1-((Diphenylmethylene)amino)-3-(tert-butyl-3'-phenylpropanoate)-4-methyl-imidazolin-2-one (3)

Yellow oil (42.2 mg, 84%): $R_f$ 0.35 (6:4 petroleum ether:Et$_2$O); $[\alpha]_D^{20}$ 0 (c 0.85, CHCl$_3$); $^1$H NMR (400 MHz, CDCl$_3$) δ 1.48 (9H, s), 1.55 (3H, s), 3.36-3.42 (2H, m), 4.67-4.70 (1H, q, J=5.1, 10.4 Hz), 5.43 (1H, s), 7.09 (2H, d, J=7.3 Hz), 7.21-7.46 (11H, m), 7.64 (2H, d, J=7.8 Hz). $^{13}$C NMR (100 MHz, CDCl$_3$) δ 169.1, 163.7, 150.8, 138.2, 135.7, 130.9, 129.9, 129.6, 129.5, 129.3, 129.0, 128.8, 128.4, 127.0, 119.0, 106.2, 82.7, 77.7, 57.6, 35.9, 28.4, 11.1. HRMS m/z 482.2440, (M+H)$^+$ calcd for [C$_{30}$H$_{32}$N$_3$O$_3$]$^+$: 482.2438. IR (neat) 1694, 1445, 1392, 1276, 1152, 747, 693.

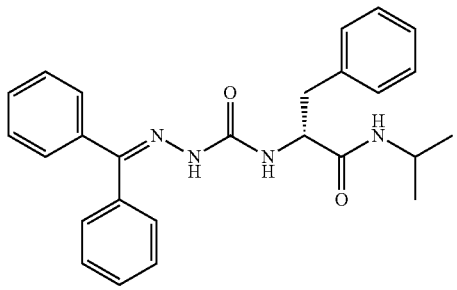 [SMILES: CC(C)NC(=O)[C@@H](Cc1ccccc1)NC(=O)NN=C(c1ccccc1)c1ccccc1]

Benzhydrylidene Aza-glycinyl-D-phenylalanine isopropyl amide (9)

tert-Butyl ester 7 (2.80 g, 6.32 mmol) was dissolved in 12 mL of a 1:1 DCM:TFA mixture, stirred for 2 h, and evaporated under reduced pressure. The resulting salt was dissolved in 70 mL of THF, cooled to −15° C., treated sequentially with isobutyl chloroformate (0.96 mL, 7.35 mmol) and N-methyl morpholine (0.81 mL, 7.35 mmol), stirred for 15 min, treated with isopropylamine (0.73 mL, 8.48 mmol), stirred at −15° C. for 1.5 h, and rotary evaporated under reduced pressure to a residue, which was dissolved in EtOAc and washed with 5% NaHCO$_3$ (3×100 mL) and 5% citric acid (3×100 mL). The organic phase was dried over MgSO$_4$, filtered, and evaporated under reduced pressure. The residue was purified by silica gel chromatography on silica gel using a 30-60% gradient of ethyl acetate in hexanes. Evaporation of the collected fractions afforded 1.6 g (66% yield) of amide 9 as a white solid: $R_f$ 0.21 (1:1 EtOAc:hexanes); $[\alpha]_D^{20}$ −22.5 (c 0.49, CHCl$_3$); $^1$H NMR (400 MHz, CDCl$_3$) δ 1.00 (3H, d, J=6.6 Hz), 1.08 (3H, d, J=6.6 Hz), 3.09 (1H, q, J=7.8, 13.5 Hz), 3.36 (1H, q, J=5.7, 13.6 Hz), 3.99-4.07 (1H, m), 4.56-4.61 (1H, m), 5.81 (1H, d, J=7.6 Hz), 6.92 (1H, d, J=8.0 Hz), 7.24-7.57 (15H, m), 7.76 (1H, s). $^{13}$C NMR (100 MHz, CDCl$_3$) δ 169.7, 154.8, 148.6, 136.5, 136.3, 131.3, 129.5, 129.4, 129.2, 128.3, 128.2, 128.0, 127.9, 126.9, 126.6, 54.7, 41.1, 38.4, 22.2, 22.0. HRMS m/z 429.2295, (M+H)$^+$ calcd for [C$_{26}$H$_{29}$N$_4$O$_2$]: 429.2285. IR (neat) 1649, 1509, 1444, 1115, 771, 746, 694.

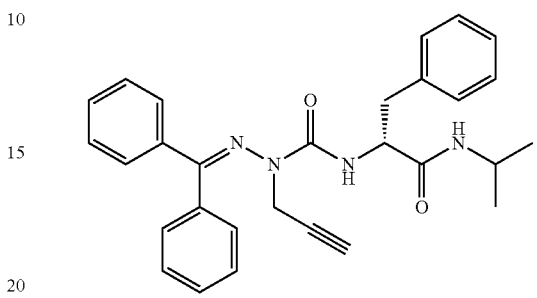

Benzhydrylidene Aza-propargylglycinyl-D-phenylalanine isopropyl amide (10)

Benzhydrylidene aza-Gly-Phe-NHiPr (9, 1.25 g, 2.92 mmol) was dissolved in 15 mL of anhydrous THF, cooled to 0° C., treated with 1.1 eq. of tBuOK (360 mg, 3.21 mmol), stirred for 1 h, and treated dropwise with 1.3 eq. of propargyl bromide (0.42 mL, 3.79 mmol). The cooling bath was removed. The reaction was allowed to warm to room temperature and stirred overnight. The volatiles were evaporated under reduced pressure. The residue was purified by chromatography on silica gel using 15% EtOAc in hexanes as solvent system. Evaporation of the collected fractions gave propargyl semicarbazone 10 as a yellow oil (970 mg, 71%): $R_f$ 0.31 (1:1 EtOAc:hexanes); $[\alpha]_D^{20}$ −8.8 (c 0.86, CHCl$_3$); $^1$H NMR (400 MHz, CDCl$_3$) δ 1.04 (3H, d, J=6.5 Hz), 1.10 (3H, d, J=6.6 Hz), 2.07-2.08 (1H, m), 3.13 (1H, dd, J=7.4, 13.6 Hz), 3.24 (1H, dd, J=6.5, 13.7 Hz), 3.97-4.09 (3H, m), 4.56 (1H, q, J=7.5, 14.4 Hz), 5.80 (1H, d, J=7.5 Hz), 7.07 (1H, d, J=7.6 Hz), 7.22-7.51 (15H, m). $^{13}$C NMR (100 MHz, CDCl$_3$) δ 169.8, 159.0, 157.9, 137.9, 136.7, 134.9, 129.9, 129.4, 129.1, 128.7, 128.3, 128.2, 127.8, 126.8, 78.0, 71.6, 55.8, 41.0, 38.1, 35.0, 22.2, 22.1. HRMS m/z 467.2447, (M+H)$^+$ calcd for [C$_{29}$H$_{31}$N$_4$O$_2$]$^+$: 467.2441. IR (neat) 1667, 1649, 1554, 1508, 1492, 768, 694, 663. The enantiomeric ratio (>99:1) was determined by SFC analysis on chiral stationary phase [Chiralcel AD-H 25 cm, 15% i-PrOH, 3 mL/min, 35° C., 150 bar, $t_r$ (minor) 5.5 min, $t_r$ (major) 12.9 min].

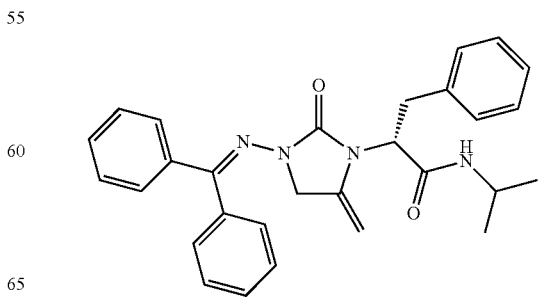

(2'R)-1-((Diphenylmethylene)amino)-3-(3'-phenyl-N'-isopropyl-2'-propionamide)-4-methylene-imidazolidin-2-one (11)

A solution of benzhydrylidene aza-propargylglycinyl-D-phenylalanine isopropyl amide (10, 758 mg, 1.63 mmol) in 8 mL of anhydrous acetonitrile was treated with a suspension of NaH (60% in oil, 195 mg, 4.88 mmol), stirred for 2 h, treated with a small volume of water, stirred for 15 min, and evaporated to a residue, which was dissolved in EtOAc and washed with brine. The aqueous layer was extracted with EtOAc (3×15 mL). The combined organic layers were dried over $Na_2SO_4$, filtered and concentrated under reduced pressure to a residue, which was purified by silica gel chromatography using 30% $Et_2O$ in petroleum ether to give amide 11 as a pale yellow oil (430 mg, 57%): $R_f$ 0.80 (EtOAc); $[\alpha]_D^{20}$ 19.8 (c 0.88, $CHCl_3$); $^1H$ NMR (400 MHz, $CDCl_3$) δ 1.05 (3H, d, J=6.6 Hz), 1.09 (3H, d, J=6.6 Hz), 3.23-3.45 (4H, m), 3.90-3.95 (1H, m), 3.97-4.10 (1H, m), 4.25-4.30 (1H, m), 4.90 (1H, q, J=5.9, 10.3 Hz), 6.38 (1H, t, J=7.7 Hz), 7.09-7.48 (15H, m). $^{13}C$ NMR (100 MHz, $CDCl_3$) δ 167.7, 158.8, 158.7, 157.4, 137.6, 137.1, 136.8, 135.2, 130.0, 129.5, 129.1, 128.7, 128.5, 128.3, 128.2, 127.9, 126.5, 84.7, 77.3, 57.3, 50.1, 41.7, 32.1, 22.4, 22.3 HRMS m/z 467.2454, (M+H)$^+$ calcd for $[C_{29}H_{31}N_4O_2]$: 467.2441 IR (neat) 1736, 1666, 1542, 1390, 1361, 1226, 1171, 925, 750, 696, 662.

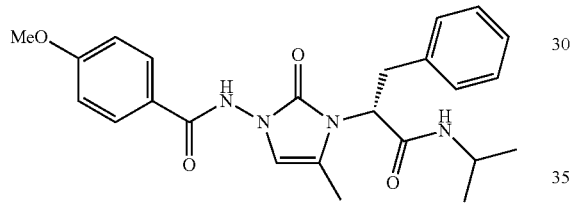

(2'R)-1-p-Methoxybenzamido-4-methyl-3-(3'-phenyl-N'-isopropyl-2'propionamide)-imidazolin-2-one (14)

Benzhydrylidene 11 (260 mg, 0.56 mmol) was dissolved in 20 mL of pyridine, treated with hydroxylamine hydrochloride (154 mg, 2.23 mmol), heated to 60° C., and stirred for 12 h. The volatiles were evaporated under reduced pressure. The residue was dissolved in DCM and evaporated to remove residual pyridine. The residue was digested with EtOAc (2×20 mL) to remove insoluble hydroxylamine hydrochloride. Evaporation of the volatiles under reduced pressure afforded 280 mg of semicarbazide contaminated with oxime by-product. The crude semicarbazide (167 mg, 0.31 mmol) was dissolved in 3 mL of DCM, treated with 4-methoxybenzoyl chloride (106 mg, 0.62 mmol) and DIEA (0.16 mL, 0.93 mmol), stirred for 12 h, and washed with 5% citric acid (3×10 mL). The organic phase was dried over $Na_2SO_4$, filtered and evaporated under reduced pressure. The residue was purified by flash chromatography on silica gel using a gradient from 25% to 70% ethyl acetate in hexanes. Evaporation of the collected fractions afforded benzamide 14 as a light yellow foam (76 mg, 56% yield), which crystallized from EtOAc after slow diffusion of vapors from a hexanes:$CHCl_3$ mixture: mp 73-76° C.; $R_f$ 0.38 (EtOAc); $[\alpha]_D^{20}$ 11.0 (c 0.88, $CHCl_3$). The variation in the amide proton chemical shift as a function of concentration (1 to 20 mM) in $CDCl_3$ was examined to assess for aggregation (see FIG. 2A). Temperature coefficients were measured for the isopropyl and benzamide NHs, after dilution to a 20 mM stock solution, by studying variations in the amide proton signal chemical shift as a function of temperature between 283K-323K (see FIG. 2B). $^1H$ NMR (400 MHz, $CDCl_3$) δ 1.14-1.16 (3H, m), 1.22 (3H, d, J=6.4 Hz), 1.76 (3H, s), 3.52 (1H, dd, J=4.0, 13.9 Hz), 3.72 (1H, t, J=12.6 Hz), 3.81 (3H, s), 4.05-4.18 (1H, m), 4.54 (1H, dd, J=3.9, 11.2 Hz), 6.04 (1H, s), 6.70 (2H, d, J=8.7 Hz), 7.06-7.26 (5H, m), 7.80 (2H, d, J=8.8 Hz), 11.09 (1H, d, J=4.8 Hz). $^{13}C$ NMR (100 MHz, $CDCl_3$) δ 168.7, 166.4, 163.1, 154.6, 138.0, 130.1, 129.3, 129.0, 127.3, 123.2, 119.6, 113.9, 111.2, 61.6, 55.7, 42.3, 35.3, 22.9, 22.7, 10.7. HRMS m/z 437.2187, (M+H)$^+$ calcd for $[C_{24}H_{29}N_4O_4]^+$: 437.2183. IR (neat) 1661, 1599, 1533, 1502, 1253, 1174, 750, 666.

Representative Procedure for the Sonogashira Coupling:

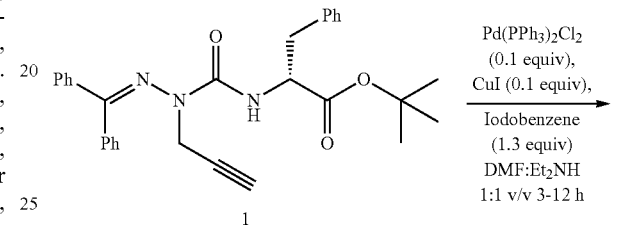

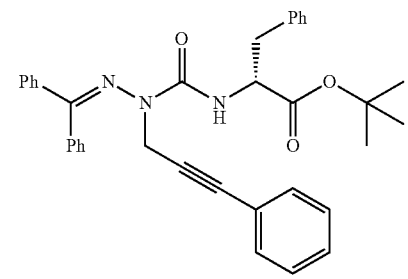

Benzhydrylidene Aza-phenylpropargylglycinyl-D-phenylalanine tert-butyl ester (18a)

A solution of benzhydrylidene aza-propargylglycinyl-D-phenylalaninyl tert-butyl ester (1, 500 mg, 1.04 mmol) in 10 mL of a 1:1 (v/v) DMF:$Et_2NH$ mixture was treated with $Pd(PPh_3)_2Cl_2$ (73 mg, 0.104 mmol), CuI (40 mg, 0.208 mmol), and iodobenzene (0.15 mL, 1.35 mmol) under inert atmosphere. The solution was stirred for 12 h, diluted with 40 mL of EtOAc, and washed with saturated $NaHCO_3$ (3×50 mL). After drying over $Na_2SO_4$, the solution was filtered, and concentrated under reduced pressure to a residue, which was purified by silica gel chromatography using 30% $Et_2O$ in petroleum ether to give aza-dipeptide 18a as orange foam (504 mg, 87%): $R_f$ 0.41 (6:4 petroleum ether:$Et_2O$); $[\alpha]_D^{20}$ −24.1 (c 1.06, $CHCl_3$); $^1H$ NMR (400 MHz, $CDCl_3$) δ 1.47 (9H, s), 3.30-3.21 (2H, m), 4.20 (1H, d, J=18.0 Hz), 4.54 (1H, d, J=17.9), 4.88-4.82 (1H, m), 7.59-7.20 (20H, m). $^{13}C$ NMR (100 MHz, $CDCl_3$) δ 171.3, 158.2, 157.7, 139.3, 137.0, 136.2, 132.0, 130.4, 130.2, 130.1, 129.8, 129.1, 129.0, 128.8, 128.7, 128.6, 127.3, 123.4, 84.8, 84.5, 82.3, 55.5, 38.9, 36.4, 28.5. HRMS m/z 558.2769, (M+H)$^+$ calcd for $[C_{36}H_{36}N_3O_3]^+$: 558.2751. IR (neat) 1731, 1679, 1488, 1366, 1150, 756, 691.

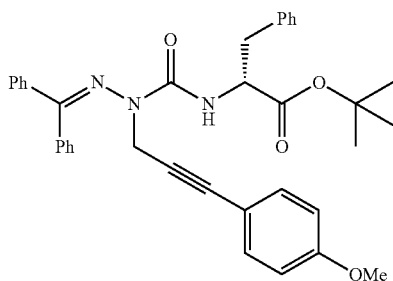 [SMILES: COc1ccc(C#CCN(N=C(c2ccccc2)c2ccccc2)C(=O)N[C@H](Cc2ccccc2)C(=O)OC(C)(C)C)cc1]

Benzhydrylidene Aza-p-methoxyphenylpropargylg-lycinyl-D-phenylalanine tert-butyl ester (18b)

Using the representative procedure, ester 1 (500 mg, 1.04 mmol) was reacted with 4-iodoanisole (316 mg, 1.35 mmol), and the product was purified with silica gel chromatography using 30% $Et_2O$ in petroleum ether to give aza-dipeptide 18b as orange foam (522 mg, 85%): $R_f$ 0.30 (6:4 petroleum ether:$Et_2O$); $[\alpha]_D^{20}$ −32.0 (c 1.02, $CHCl_3$); $^1H$ NMR (400 MHz, $CDCl_3$) δ 1.48 (9H, s), 3.32-3.23 (2H, m), 3.77 (3H, s), 4.21 (1H, d, J=17.93 Hz), 4.54 (1H, d, J=17.89 Hz), 4.89-4.84 (1H, m), 6.82-6.80 (2H, m), 7.51-7.22 (19H, m). $^{13}C$ NMR (100 MHz, $CDCl_3$) δ 170.5, 159.2, 157.5, 156.8, 138.5, 136.2, 135.4, 132.7, 129.9, 129.6, 129.4, 129.3, 129.0, 128.3, 128.2, 128.0, 127.1, 126.5, 114.7, 113.5, 83.6, 82.5, 81.5, 77.1, 54.9, 54.8, 38.1, 35.7, 27.7. HRMS m/z 588.2861, (M+H)$^+$ calcd for $[C_{37}H_{38}N_3O_4]^+$: 588.2857. IR (neat) 1678, 1487, 1443, 1366, 1246, 1149, 831, 695.

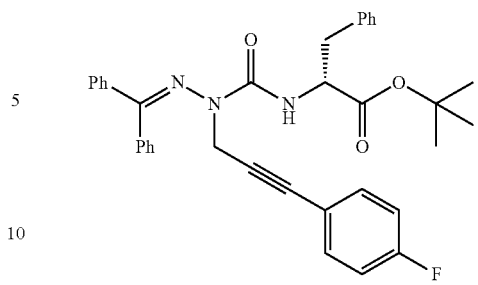

Benzhydrylidene Aza-p-fluorophenylpropargylglyci-nyl-D-phenylalanine tert-butyl ester (18d)

Using the representative procedure, ester 1 (500 mg, 1.04 mmol) was reacted with 4-fluoroiodobenzene (0.16 mL, 1.35 mmol), and the product was purified by silica gel chromatography using 20% $Et_2O$ in petroleum ether to give aza-dipeptide 18d as a light orange foam (536 mg, 90%): $R_f$ 0.46 (6:4 petroleum ether:$Et_2O$); $[\alpha]_D^{20}$ −24.6 (c 0.85, $CHCl_3$); $^1H$ NMR (400 MHz, $CDCl_3$) δ 1.47 (9H, s), 3.31-3.22 (2H, m), 4.21 (1H, d, J=17.93 Hz), 4.52 (1H, d, J=17.97 Hz), 4.89-4.83 (1H, m), 6.98-6.94 (2H, m), 7.51-7.21 (17H, m). $^{13}C$ NMR (100 MHz, $CDCl_3$) δ 171.3, 164.1, 161.6, 158.3, 157.8, 139.2, 137.0, 136.1, 134.0, 133.9, 130.5, 130.2, 129.7, 129.0, 128.8, 128.6, 127.3, 119.4, 116.0, 115.9, 84.6, 83.4, 82.2, 77.9, 55.5, 38.9, 36.4, 28.5 HRMS m/z 576.2662, (M+H)$^+$ calcd for $[C_{36}H_{35}FN_3O_3]^+$: 576.2657. IR (neat) 1678, 1490, 1365, 1219, 1150, 835, 694.

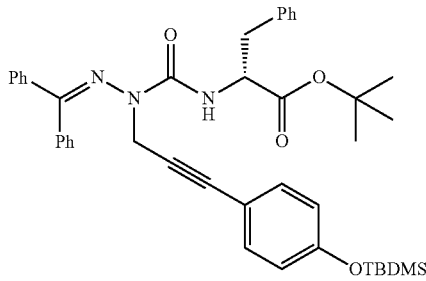 [SMILES: CC(C)(C)OC(=O)[C@@H](Cc1ccccc1)NC(=O)N(CC#Cc1ccc(O[Si](C)(C)C(C)(C)C)cc1)N=C(c1ccccc1)c1ccccc1]

Benzhydrylidene Aza-p-dimethyl-tert-butylsilylox-yphenylpropargylglycinyl-D-phenylalanine tert-butyl ester (18c)

Using the representative procedure, ester 1 (500 mg, 1.04 mmol) was reacted with 4-(OTBDMS)-iodobenzene (425 mg, 1.35 mmol) and the product was purified by silica gel chromatography using a gradient from 20-100% $Et_2O$ in petroleum ether to give aza-dipeptide 18c as a brown oil (427 mg, 60%): $R_f$ 0.52 (6:4 petroleum ether:$Et_2O$); $[\alpha]_D^{20}$ −37.5 (c 0.88, $CHCl_3$); $^1H$ NMR (400 MHz, $CDCl_3$) δ 0.20 (6H, s), 0.98 (9H, s), 1.43 (9H, s), 3.25-3.16 (2H, m), 4.11 (1H, d, J=17.93 Hz), 4.46 (1H, d, J=17.93 Hz), 4.81-4.76 (1H, m), 6.74-6.71 (2H, m), 7.49-7.39 (8H, m), 7.35-7.31 (2H, m), 7.26-7.23 (5H, m), 7.19-7.13 (3H, m). $^{13}C$ NMR (100 MHz, $CDCl_3$) δ 170.5, 157.5, 156.8, 155.4, 138.5, 136.2, 135.4, 132.6, 129.5, 129.4, 129.2, 128.9, 128.3, 128.1, 128.0, 127.8, 126.4, 119.7, 115.4, 83.5, 82.6, 81.5, 76.9, 54.7, 38.1, 35.7, 27.6, 25.3, 17.8, −4.8. HRMS m/z 688.3566, (M+H)$^+$ calcd for $[C_{42}H_{50}N_3O_4Si]^+$: 688.3565. IR (neat) 1682, 1491, 1252, 1151, 907, 838, 695.

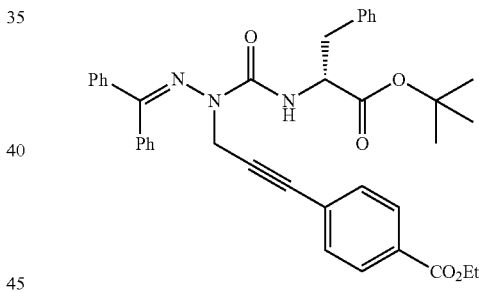

Benzhydrylidene Aza-p-ethoxycarbonylphenylprop-argylglycinyl-D-phenylalanine tert-butyl ester (18e)

Using the representative procedure, ester 1 (100 mg, 0.208 mmol) was reacted with ethyl 4-iodobenzoate (45 μL, 0.27 mmol), and the product was purified by silica gel chromatography using a gradient from 30% $Et_2O$ in petroleum ether to 100% $Et_2O$ to give aza-dipeptide 18e as a dark brown oil (122 mg, 93%): $R_f$ 0.27 (6:4 petroleum ether:$Et_2O$); $[\alpha]_D^{20}$ −29.2 (c 0.90, $CHCl_3$); $^1H$ NMR (400 MHz, $CDCl_3$) δ 1.40 (3H, t, J=7.1 Hz), 1.44 (9H, s), 3.17-3.27 (2H, m), 4.19 (1H, d, J=18.0 Hz), 4.38 (2H, q, J=7.0, 14.3 Hz), 4.50 (1H, d, J=18.0 Hz), 4.78-4.83 (1H, m), 7.15 (1H, d, J=8.2 Hz), 7.23-7.28 (5H, m), 7.33-7.49 (12H, m), 7.96 (2H, d, J=8.2 Hz). $^{13}C$ NMR (100 MHz, $CDCl_3$) δ 171.2, 166.4, 158.2, 158.0, 139.1, 136.9, 136.0, 131.8, 130.5, 130.2, 130.2, 130.1, 129.8, 129.7, 129.0, 128.8, 128.6, 127.9, 127.2, 87.9, 83.7, 82.3, 77.7, 61.5, 55.4, 38.9, 36.4, 28.4, 14.7. HRMS m/z 630.2972, (M+H)$^+$ calcd for $[C_{39}H_{40}N_3O_5]^+$: 630.2962. IR (neat) 2919, 2774, 2361, 1718, 1684, 1494, 1392, 1273, 1154, 1105, 768, 698.

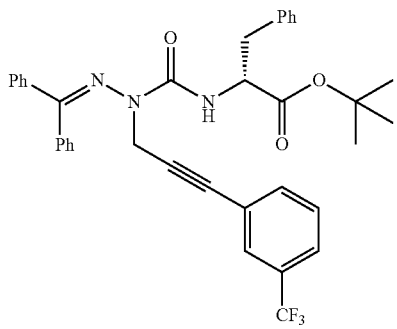 [SMILES: CC(C)(C)OC(=O)[C@@H](Cc1ccccc1)NC(=O)N(CC#Cc1cccc(C(F)(F)F)c1)N=C(c1ccccc1)c1ccccc1]

Benzhydrylidene Aza-m-trifluoromethylphenylpropargylglycinyl-D-phenylalanine tert-butyl ester (18f)

Using the representative procedure, ester 1 (500 mg, 1.04 mmol) was reacted with 1-iodo-3-trifluoromethylbenzene (0.19 mL, 1.35 mmol), and the product was purified by silica gel chromatography using 30% $Et_2O$ in petroleum ether to give aza-dipeptide 18f as a brown oil (520 mg, 80%): $R_f$ 0.61 (6:4 petroleum ether:$Et_2O$); $[\alpha]_D^{20}$ −20.4 (c 0.81, $CHCl_3$); $^1H$ NMR (400 MHz, $CDCl_3$) δ 1.46 (9H, s), 3.29-3.19 (2H, m), 4.20 (1H, d, J=18.05), 4.49 (1H, d, J=18.05), 4.85-4.80 (1H, m), 7.58-7.15 (20H, m). $^{13}C$ NMR (100 MHz, $CDCl_3$) δ 170.5, 157.5, 157.4, 138.2, 136.1, 135.2, 134.4, 134.2, 130.6, 130.3, 129.8, 129.7, 129.4, 129.3, 128.9, 128.4, 128.3, 128.1, 128.0, 127.8, 127.6, 127.5, 126.5, 124.7, 124.4, 124.3, 123.5, 122.0, 85.8, 82.1, 81.5, 76.9, 54.7, 38.1, 35.7, 27.6. HRMS m/z 626.2630, (M+H)$^+$ calcd for $[C_{37}H_{35}F3N_3O_3]^+$: 626.2625. IR (neat) 1680, 1486, 1330, 1152, 1125, 1093, 1072, 693.

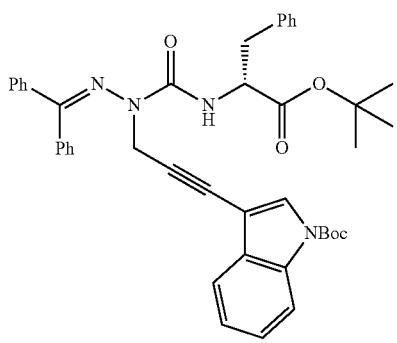 [SMILES: CC(C)(C)OC(=O)[C@@H](Cc1ccccc1)NC(=O)N(CC#Cc1cn(C(=O)OC(C)(C)C)c2ccccc12)N=C(c1ccccc1)c1ccccc1]

Benzhydrylidene Aza-N-Boc-3-indolylpropargylglycinyl-D-phenylalanine tert-butyl ester (18g)

Using the representative procedure, ester 1 (500 mg, 1.04 mmol) was reacted with N-Boc-3-iodoindole (464 mg, 1.35 mmol), and the product was purified by silica gel chromatography using 25% $Et_2O$ in petroleum ether to give aza-dipeptide 18g as an orange foam (473 mg, 65%): $R_f$ 0.43 (6:4 petroleum ether:$Et_2O$); $[\alpha]_D^{20}$ −19.9 (c 0.89, $CHCl_3$); $^1H$ NMR (400 MHz, $CDCl_3$) δ 1.47 (9H, s), 1.69 (9H, s), 3.32-3.24 (2H, m), 4.26 (1H, d, J=17.93 Hz), 4.61 (1H, d, J=17.77 Hz), 4.91-4.83 (1H, m), 7.68-7.20 (20H, m), 8.21-8.13 (1H, m). $^{13}C$ NMR (100 MHz, $CDCl_3$) δ 171.2, 158.3, 157.8, 149.5, 139.0, 136.9, 136.1, 134.9, 131.0, 130.4, 130.1, 129.8, 129.1, 129.0, 128.8, 128.6, 127.3, 125.5, 123.5, 120.5, 115.6, 103.5, 88.2, 84.7, 82.2, 77.8, 76.4, 55.5, 38.9, 36.6, 28.6, 28.4. HRMS m/z 697.3387, (M+H)$^+$ calcd for $[C_{43}H_{45}N_4O_5]^+$: 697.3384. IR (neat) 1733, 1681, 1491, 1451, 1366, 1231, 1150, 1098, 745, 695.

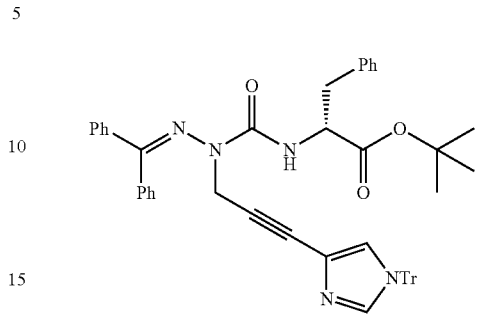

Benzhydrylidene Aza-N-trityl-4-imidazolylpropargylglycinyl-D-phenylalanine tert-butyl ester (18h)

Using the representative procedure, ester 1 (500 mg, 1.04 mmol) was reacted with N-trityl-4-iodoimidazole (588 mg, 1.35 mmol), and the product was purified by silica gel chromatography using a gradient of 50-70% $Et_2O$ in petroleum ether to give aza-dipeptide 18h as orange foam (378 mg, 46%): $R_f$ 0.33 (3:7 petroleum ether:$Et_2O$); $[\alpha]_D^{20}$ −22.0 (c 0.98, $CHCl_3$); $^1H$ NMR (400 MHz, $CDCl_3$) δ 1.41 (9H, s), 3.18 (2H, d, J=5.88 Hz), 4.10 (1H, d, J=17.97 Hz), 4.40 (1H, d, J=17.97 Hz), 4.78-4.73 (1H, m), 6.90 (1H, d, J=1.16 Hz), 7.45-7.05 (32H, m). $^{13}C$ NMR (100 MHz, $CDCl_3$) δ 171.7, 158.6, 158.5, 142.8, 139.6, 139.5, 137.4, 136.4, 130.6, 130.5, 130.4, 130.1, 129.5, 129.4, 129.1, 129.0, 128.9, 128.8, 127.6, 126.6, 123.9, 85.2, 82.6, 78.6, 78.1, 76.5, 55.8, 39.3, 36.9, 28.8. HRMS m/z 790.3723, (M+H)$^+$ calcd for $[C_{52}H_{48}N_5O_3]^+$: 790.3752. IR (neat) 1682, 1489, 1444, 1151, 744, 695.

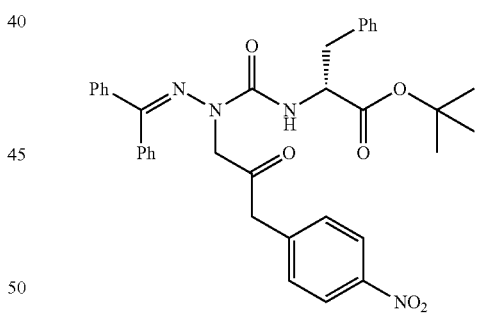

Benzhydrylidene Aza-3-p-nitrophenyl-2-oxopropylglycinyl-D-phenylalanine tert-butyl ester (20)

Using the representative procedure, ester 1 (500 mg, 1.04 mmol) was reacted with 1-iodo-4-nitrobenzene (337 mg, 1.35 mmol), and the product was purified by silica gel chromatography using a gradient from 30% $Et_2O$ in petroleum ether to 100% $Et_2O$ to give ketone 20 as orange foam (400 mg, 64%): $R_f$ 0.09 (6:4 petroleum ether:$Et_2O$); $[\alpha]_D^{20}$ 6.4 (c 0.83, $CHCl_3$); $^1H$ NMR (400 MHz, $CDCl_3$) δ 1.45 (9H, s), 3.19 (2H, d, J=5.9 Hz), 3.44 (2H, q, J=16.9, 30.6 Hz), 4.12 (1H, d, J=18.1 Hz), 4.36 (1H, d, J=18.1 Hz), 4.74-4.79 (1H, m), 7.15 (1H, d, J=8.2 Hz), 7.20-7.54 (17H, m), 8.14 (2H, d, J=8.7 Hz). $^{13}C$ NMR (100 MHz, $CDCl_3$) δ 200.7, 171.2, 158.0, 154.7, 147.4, 141.3, 138.8, 136.8, 135.9, 131.0, 130.4, 130.0, 129.6, 128.9, 128.7, 127.4, 124.0, 82.4, 77.7, 56.4, 55.4, 45.7, 38.9, 28.4. HRMS m/z 621.2709, (M+H)+ calcd for [C₃₆H₃₇N₄O₆]+: 621.2708. IR (neat) 1730, 1677, 1490, 1344, 1149, 696.

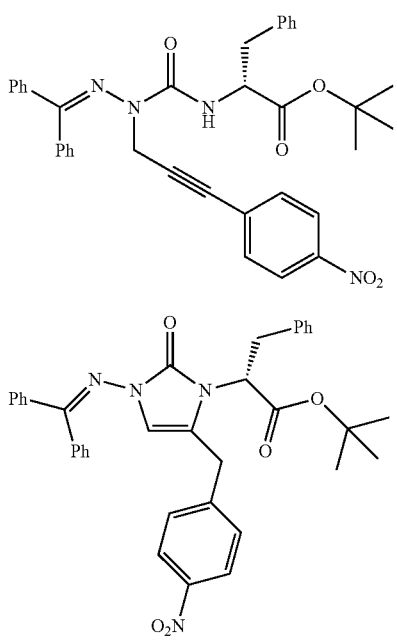

22 (Major)

23 (Minor)

Benzhydrylidene Aza-p-nitrophenylpropargylglycinyl-D-phenylalanine tert-butyl ester (22) and (2'R)-1-((Diphenylmethylene)amino)-3-(tert-butyl-3'-phenyl-2'-propanoate)-4-p-nitrobenzylimidazolin-2-one (23)

Ester 1 (500 mg, 1.13 mmol) was dissolved in 6 mL of anhydrous THF, cooled to 0° C., treated with 1.1 eq. of t-BuOK (139 mg, 1.24 mmol), stirred for 1 h, and treated dropwise with 1.3 eq. of 1-(3-bromoprop-1-yn-1-yl)-4-nitrobenzene (350 mg, 1.47 mmol). The ice bath was removed and the reaction was allowed to warm to room temperature with stirring overnight. The volatiles were removed by evaporation under reduced pressure. The residue was purified by chromatography on silica gel using 30% Et₂O in petroleum ether as solvent system to give propargylglycine 22 (major) and imidazolin-2-one 23 (minor) as an inseparable 3:1 mixture:yellow oil (226 mg, 33%); R_f 0.51 (6:4 petroleum ether:Et₂O); ¹H NMR (400 MHz, CDCl₃) distinct signal for 22 δ 1.44 (9H, s), 3.22-3.19 (2H, m), 4.22 (1H, d, J=18.17 Hz), 4.47 (1H, d, J=18.21), 4.81-4.76 (1H, m), 7.63-7.09 (17H, m), 8.15-8.13 (2H, m); distinct signals for 23 δ 1.48 (9H, s), 3.39-3.32 (1H, m), 3.53-3.48 (1H, m), 3.82-3.92 (2H, m), 5.11-5.07 (1H, m), 5.51 (1H, brs), 6.75 (2H, d, J=8.80 Hz), 7.63-7.09 (15H, m), 8.07-8.04 (2H, m). ¹³C NMR (100 MHz, CDCl₃) signals for 22 and 23 δ 171.2, 158.4, 158.1, 147.4, 138.8, 136.9, 135.9, 132.7, 130.6, 130.3, 130.2, 130.1, 129.9, 129.6, 129.5, 129.1, 129.0, 128.8, 128.7, 128.6, 127.2, 127.1, 124.3, 123.9, 99.2, 90.6, 82.5, 82.3, 57.1, 55.4, 51.9, 38.9, 36.5, 34.2, 28.4, 28.3. HRMS m/z 603.2603, (M+H)+ calcd for [C₃₆H₃₅N₄O₅]+: 603.2602. IR (neat) 1732, 1681, 1515, 1490, 1367, 1338, 1151, 1107, 853, 749, 696.

NaH-Promoted Cyclization:

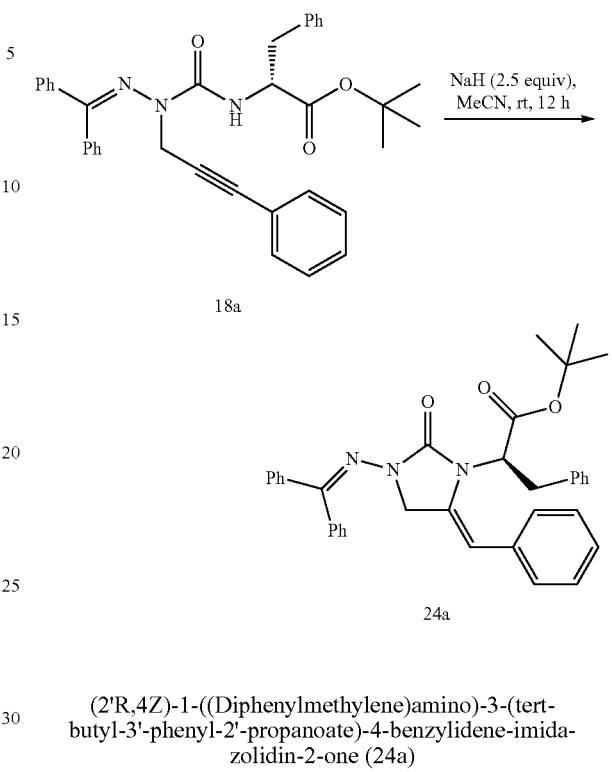

18a

24a (2'R,4Z)-1-((Diphenylmethylene)amino)-3-(tert-butyl-3'-phenyl-2'-propanoate)-4-benzylidene-imidazolidin-2-one (24a)

Using the representative procedure for the synthesis of imidazolidin-2-one 2, aza-propargylglycine 18a (50 mg, 0.09 mmol) was reacted with NaH (9 mg, 0.224 mmol), and the product was purified with silica gel chromatography using 30% Et₂O in petroleum ether to give a yellow oil (34.3 mg, 69%): R_f 0.53 (6:4 petroleum ether:Et₂O); [α]_D²⁰ 90.7 (c 1.53, CHCl₃); ¹H NMR (400 MHz, CDCl₃) δ 1.53 (9H, s), 3.13 (1H, dd, J=4.7, 14.0 Hz), 3.40-3.48 (2H, m), 3.60 (1H, dd, J=1.6, 13.5 Hz), 4.33 (1H, q, J=4.8, 11.0 Hz), 4.99 (1H, s), 6.88-6.94 (2H, m), 6.98 (2H, d, J=6.8 Hz), 7.19-7.51 (14H, m), 7.64-7.68 (2H, m). ¹³C NMR (100 MHz, CDCl₃) δ 167.8, 158.9, 157.2, 137.9, 137.4, 135.7, 134.6, 132.3, 129.6, 129.1, 128.9, 128.8, 128.7, 128.2, 128.1, 127.7, 127.6, 126.3, 126.1, 98.5, 81.5, 57.8, 52.9, 34.1, 27.7. HRMS m/z 558.2763, (M+H)+ calcd for [C₃₆H₃₆N₃O₃]+: 558.2751. IR (neat) 1734, 1701, 1674, 1408, 1368, 1278, 1154, 751, 696. The cis double bond geometry was ascertained by 2D NMR spectroscopy (COSY). The enantiomeric ratio (73:27) was determined by SFC analysis on chiral stationary phase (Chiralcel OJ-H 25 cm, 5% i-PrOH, 3 mL/min, 35° C., 150 bar, t_r (minor) 9.2 min, t_r (major) 11.2 min.

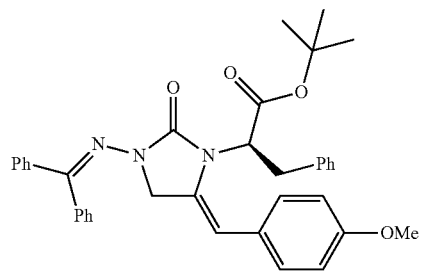 [SMILES: COc1ccc(/C=C2/CN(N=C(c3ccccc3)c3ccccc3)C(=O)N2[C@H](Cc2ccccc2)C(=O)OC(C)(C)C)cc1]

(2'R,4Z)-1-((Diphenylmethylene)amino)-3-(tert butyl-3'-phenyl-2'-propanoate)-4-(p-methoxybenzylidene)imidazolidin-2-one (24b)

Using the representative procedure for the synthesis of imidazolidin-2-one 2, aza-propargylglycine 18b (192 mg, 0.327 mmol) was reacted with NaH (39 mg, 0.98 mmol) in 2 mL of anhydrous acetonitrile for 12 h, and the product was purified with silica gel chromatography using 30% $Et_2O$ in petroleum ether to give a yellow oil (19 mg, 10%): $R_f$ 0.50 (6:4 petroleum ether:$Et_2O$); $[\alpha]_D^{20}$ 127.2 (c 1.03, $CHCl_3$); $^1H$ NMR (400 MHz, $CDCl_3$) δ 1.51 (9H, s), 3.12 (1H, dd, J=4.8, 13.9 Hz), 3.37-3.43 (2H, m), 3.57 (1H, dd, J=1.6, 13.4 Hz), 3.83 (3H, s), 4.34 (1H, dd, J=4.9, 11.0 Hz), 4.92 (1H, s), 6.78 (2H, d, J=8.5 Hz), 6.88 (2H, d, J=8.5 Hz), 6.90-6.93 (2H, m), 7.22-7.23 (3H, m), 7.33-7.41 (5H, m), 7.47-7.48 (3H, m), 7.62-7.64 (2H, m). $^{13}C$ NMR (100 MHz, $CDCl_3$) δ 168.6, 159.4, 158.7, 158.0, 138.7, 138.2, 136.5, 132.4, 130.6, 130.3, 129.9, 129.6, 129.0, 128.8, 128.5, 128.4, 127.5, 126.8, 113.9, 98.9, 82.2, 77.6, 58.3, 55.7, 53.6, 34.9, 28.4. HRMS m/z 588.2866, $(M+H)^+$ calcd for $[C_{37}H_{38}N_3O_4]$: 588.2857. IR (neat) 1732, 1676, 1509, 1368, 1285, 1244, 1152, 750, 693.

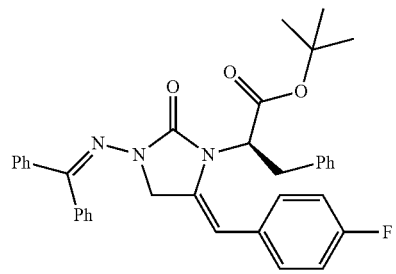 [SMILES: CC(C)(C)OC(=O)[C@@H](Cc1ccccc1)N1C(=O)N(N=C(c2ccccc2)c2ccccc2)C/C1=C/c1ccc(F)cc1]

(2'R,4Z)-1-((Diphenylmethylene)amino)-3-(tert-butyl-3'-phenyl-2'-propanoate)-4-(p-fluorobenzylidene)imidazolidin-2-one (24d)

Using the representative procedure for the synthesis of imidazolidin-2-one 2, aza-propargylglycine 18d (200 mg, 0.35 mmol) was reacted with NaH (34 mg, 0.87 mmol) in 3 mL of anhydrous acetonitrile for 12 h, and the product was purified with silica gel chromatography using 30% $Et_2O$ in petroleum ether to give a yellow oil (128 mg, 64%): $R_f$ 0.52 (6:4 petroleum ether:$Et_2O$); $[\alpha]_D^{20}$ 108.3 (c 1.08, $CHCl_3$); $^1H$ NMR (400 MHz, $CDCl_3$) δ 1.51 (9H, s), 3.12 (1H, dd, J=4.6, 13.9 Hz), 3.39-3.47 (2H, m), 3.59 (1H, dd, J=1.49, 13.5 Hz), 4.23 (1H, dd, J=4.7, 11.0 Hz), 4.91 (1H, s), 6.88-6.96 (6H, m), 7.23-7.24 (3H, m), 7.34-7.42 (5H, m), 7.47-7.49 (3H, m), 7.63-7.65 (2H, m). $^{13}C$ NMR (100 MHz, $CDCl_3$) δ 168.4, 163.1, 160.7, 160.1, 157.9, 138.6, 138.2, 136.4, 133.4, 131.3, 131.1, 130.4, 129.8, 129.7, 129.6, 129.0, 128.9, 128.5, 126.9, 115.5, 115.4, 98.0, 82.5, 77.7, 58.7, 53.6, 34.9, 28.4. HRMS m/z 576.2665, $(M+H)^+$ calcd for $[C_{36}H_{35}FN_3O_3]^+$: 576.2657. IR (neat) 1731, 1675, 1367, 1226, 1151, 750, 692.

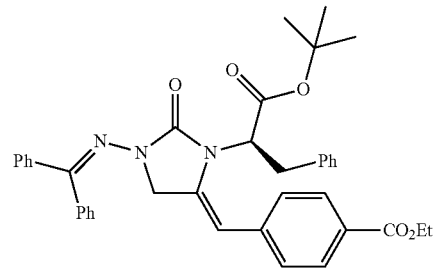 [SMILES: CCOC(=O)c1ccc(/C=C2/CN(N=C(c3ccccc3)c3ccccc3)C(=O)N2[C@H](Cc2ccccc2)C(=O)OC(C)(C)C)cc1]

(2'R,4Z)-1-((Diphenylmethylene)amino)-3-(tert-butyl-3'-phenyl-2'-propanoate)-4-(p-ethoxycarbonylbenzylidene)imidazolidin-2-one (24e)

Using the representative procedure for the synthesis of imidazolidin-2-one 2, aza-propargylglycine 18e (55.6 mg, 0.0884 mmol) was reacted with NaH (9 mg, 0.221 mmol) in 1 mL of anhydrous acetonitrile for 5 h, and the product was purified with silica gel chromatography using a gradient from 40-60% $Et_2O$ in petroleum ether to give a yellow oil (23.5 mg, 42%): $R_f$ 0.17 (6:4 petroleum ether:$Et_2O$); $[\alpha]_D^{20}$ 97.5 (c 1.23, $CHCl_3$); $^1H$ NMR (400 MHz, $CDCl_3$) δ 1.43 (3H, t, J=7.1 Hz), 1.46 (9H, s), 2.97 (2H, q, J=16.6, 42 Hz), 3.34-3.46 (2H, m), 4.29 (1H, dd, J=4.8, 10.3 Hz), 4.41 (2H, q, J=7.3, 14.1 Hz), 5.10 (1H, s), 6.86 (2H, d, J=8.0 Hz), 7.02-7.04 (2H, m), 7.11-7.16 (1H, m), 7.22-7.28 (4H, m), 7.33-7.44 (6H, m), 7.65-7.67 (2H, m), 7.85 (2H, d, J=8.3 Hz). $^{13}C$ NMR (100 MHz, $CDCl_3$) δ 168.0, 166.3, 164.3, 150.0, 141.1, 138.1, 137.4, 135.0, 130.6, 129.6, 129.5, 129.1, 128.8, 128.6, 128.3, 128.1, 126.6, 121.0, 107.3, 82.3, 77.2, 60.9, 58.2, 35.1, 30.8, 27.9, 14.4. HRMS m/z 630.2958, $(M+H)^+$ calcd for $[C_{39}H_{40}N_3O_5]^+$: 630.2963. IR (neat) 1705, 1445, 1405, 1273, 1153, 1102, 694.

(2'R,4Z)-1-((Diphenylmethylene)amino)-3-(tert-butyl-3'-phenyl-2'-propanoate)-4-(m-trifluoromethylbenzylidene)-imidazolidin-2-one (24f) and (2'R)-1-(diphenylmethylene)amino)-3-(tert-butyl-3'-phenyl-2'-propanoate)-4-(m-trifluoromethylbenzyl)imidazolin-2-one (25f)

Using the representative procedure for the synthesis of imidazolidin-2-one 2, aza-propargylglycine 18f (431 mg, 0.689 mmol) was reacted with NaH (69 mg, 1.72 mmol) in 6 mL of anhydrous acetonitrile for 12 h, and the product was purified with silica gel chromatography using a gradient from 10-40% $Et_2O$ in petroleum ether to give 24f and 25f as yellow oils. First to elute was 24f (74.7 mg, 17%): $R_f$ 0.85 (6:4 petroleum ether:$Et_2O$); $[\alpha]_D^{20}$ 158.6 (c 0.86, $CHCl_3$); $^1H$ NMR (400 MHz, $CDCl_3$) δ 1.51 (9H, s), 3.10 (1H, dd, J=4.5, 13.9 Hz), 3.33-3.39 (1H, m), 3.47-3.65 (2H, m), 4.16 (1H, dd, J=4.5, 11.0 Hz), 4.89 (1H, s), 6.78-6.89 (2H, m), 7.11 (1H, d, J=7.2 Hz), 7.18-7.23 (4H, m), 7.33-7.50 (10H, m), 7.65 (2H, d, J=7.2 Hz). $^{13}C$ NMR (100 MHz, $CDCl_3$) δ 168.1, 160.9, 157.6, 138.4, 138.1, 136.4, 136.3, 134.4, 132.9, 131.1, 130.8, 130.5, 129.7, 129.6, 129.1, 128.9, 128.8, 128.6, 128.5, 127.0, 126.2, 125.8, 123.7, 123.0, 97.2, 82.7, 77.7, 58.8, 53.6, 53.6, 35.0, 30.1, 28.3, 24.3. HRMS m/z 626.2627, $(M+H)^+$ calcd for $[C_{37}H_{35}F3N_3O_3]^+$: 626.2625. IR (neat) 1739, 1672, 1368, 1329, 1154, 1122, 1072, 749, 696. Next to elute was 25f (71.3 mg, 17%): $R_f$ 0.31 (6:4 petroleum ether:$Et_2O$); $[\alpha]_D^{20}$ 1.7 (c 0.78, $CHCl_3$); $^1H$ NMR (400 MHz, $CDCl_3$) δ 1.47 (9H, s), 2.95 (2H, s), 3.36-3.48 (2H, m), 4.32-4.35 (1H, m), 4.99 (1H, s), 6.97-7.08 (4H, m), 7.20-7.47 (13H, m), 7.65-7.67 (2H, m). $^{13}$C NMR (100 MHz, CDCl$_3$) δ 168.4, 164.4, 150.5, 138.5, 137.8, 137.1, 135.2, 132.5, 131.1, 129.9, 129.7, 129.5, 129.2, 129.1, 129.0, 128.9, 128.5, 127.1, 125.8, 124.1, 121.7, 107.6, 82.9, 77.7, 58.6, 35.6, 31.0, 30.1, 28.3. HRMS m/z 626.2638, (M+H)$^+$ calcd for [C$_{37}$H$_{35}$F$_3$N$_3$O$_3$]$^+$: 626.2625. IR (neat) 1696, 1408, 1328, 1153, 1120, 1074, 750, 694.

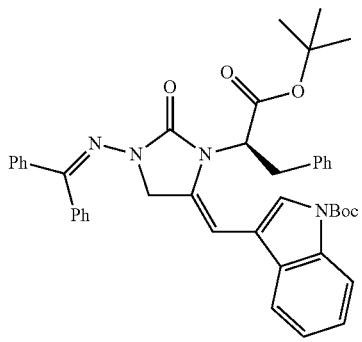 [SMILES: CC(C)(C)OC(=O)[C@@H](Cc1ccccc1)N1C(=O)N(N=C(c2ccccc2)c2ccccc2)C/C1=C/c1cn(C(=O)OC(C)(C)C)c2ccccc12]

(2'R,4Z)-1-((Diphenylmethylene)amino)-3-(tert-butyl-3'-phenylpropanoate)-4-(N'-Boc-3'-indoylmethylene)imidazolidin-2-one (24g)

Using the representative procedure for the synthesis of imidazolidin-2-one 2, aza-propargylglycine 18g (250 mg, 0.359 mmol) was reacted with NaH (36 mg, 0.89 mmol) in 3 mL of anhydrous acetonitrile for 12 h, and the product was purified with silica gel chromatography using 30% Et$_2$O in petroleum ether to give a yellow oil (101 mg, 40%): R$_f$ 0.45 (6:4 petroleum ether:Et$_2$O); [α]$_D^{20}$ 52.78 (c 1.07, CHCl$_3$); $^1$H NMR (400 MHz, CDCl$_3$) δ 1.5 (9H, s), 1.71 (9H, s), 3.11 (1H, dd, J=5.0, 13.9 Hz), 3.35-3.41 (1H, m), 3.54 (1H, dd, J=2.0, 13.6 Hz), 3.69 (1H, dd, J=1.3, 13.6 Hz), 4.61 (1H, dd, J=5.0, 10.7 Hz), 4.78 (1H, s), 6.81 (2H, d, J=7.0 Hz), 7.14-7.28 (6H, m), 7.35-7.44 (6H, m), 7.50-7.51 (3H, m), 7.66 (2H, d, J=7.3 Hz), 8.14 (1H, d, J=7.5 Hz). $^{13}$C NMR (100 MHz, CDCl$_3$) δ 168.6, 159.6, 157.9, 149.9, 138.7, 138.1, 136.5, 135.6, 135.3, 130.8, 130.4, 129.8, 129.7, 129.0, 128.9, 128.6, 128.5, 126.7, 125.2, 124.6, 123.11, 120.6, 115.5, 114.7, 88.3, 84.3, 82.5, 77.7, 57.8, 53.6, 34.9, 28.6, 28.3. HRMS m/z 697.3386, (M+H)$^+$ calcd for [C$_{43}$H$_{45}$N$_4$O$_5$]$^+$: 697.3385. IR (neat) 1726, 1685, 1450, 1367, 1150, 744, 694.

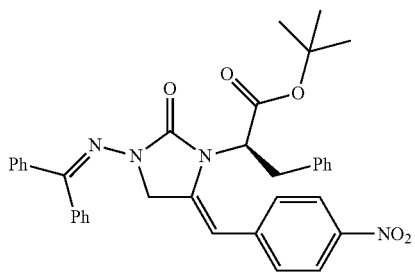 [SMILES: CC(C)(C)OC(=O)[C@@H](Cc1ccccc1)N1C(=O)N(N=C(c2ccccc2)c2ccccc2)C/C1=C/c1ccc([N+](=O)[O-])cc1]

(2'R,4Z)-1-((Diphenylmethylene)amino)-3-(tert-butyl-3'-phenyl-2'-propanoate)-4-(p-nitrobenzylidene)imidazolidin-2-one ester (24h)

Using the representative procedure for the synthesis of imidazolidin-2-one 2, aza-propargylglycine 22 (210 mg, 0.35 mmol) was reacted with NaH (21 mg, 0.52 mmol) in 3 mL of anhydrous THF for 40 min, and the product was purified with silica gel chromatography using a gradient of 30-50% Et$_2$O in petroleum ether to give an orange foam (87 mg, 41%): R$_f$ 0.20 (1:1 petroleum ether:Et$_2$O); [α]$_D^{20}$ 15.2 (c 0.86, CHCl$_3$); $^1$H NMR (400 MHz, CDCl$_3$) δ 1.47 (9H, s), 2.98-3.08 (2H, m), 3.36 (1H, dd, J=4.2, 14.1 Hz), 3.46 (1H, dd, J=11.0, 14.1 Hz), 4.27 (1H, dd, J=3.6, 11.0 Hz), 5.08 (1H, s), 6.92 (2H, d, J=8.6 Hz), 7.01-7.04 (2H, m), 7.21-7.46 (11H, m), 7.65 (2H, d, J=7.3 Hz), 8.02 (2H, d, J=8.7 Hz). $^{13}$C NMR (100 MHz, CDCl$_3$) δ 168.3, 165.1, 150.4, 147.2, 144.0, 138.4, 137.6, 135.4, 131.2, 129.9, 129.8, 129.6, 129.3, 129.0, 128.6, 127.1, 123.9, 120.8, 108.0, 83.0, 77.7, 58.7, 35.5, 31.0, 28.4. HRMS m/z 603.2605, (M+H)$^+$ calcd for [C$_{36}$H$_{35}$N$_4$O$_5$]$^+$: 603.2602. IR (neat) 1697, 1518, 1407, 1344, 1277, 1152, 693.

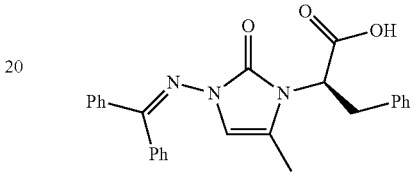

(2'R)-1-((Diphenylmethylene)amino)-3-(3'-phenyl-2'-propanoate)-4-methylimidazolin-2-one (4)

tert-Butyl ester 3 (111 mg, 0.23 mmol) was dissolved in 4 ml of a 1:1 DCM:TFA and stirred for 5 h. The volatiles were removed by evaporation under reduced pressure and the residue was dissolved in DCM and concentrated to remove residual TFA to give a brown oil (91 mg, 93%): R$_f$ 0.24 (1:9 MeOH:DCM); [α]$_D^{20}$ 0 (c 0.77, CHCl$_3$); $^1$H NMR (400 MHz, CDCl$_3$) δ 1.50 (3H, s), 3.47 (2H, d, J=7.6 Hz), 4.51 (1H, t, J=7.6 Hz), 6.07 (1H, s), 7.13 (2H, d, J=7.1 Hz), 7.19-7.32 (3H, m), 7.46-7.53 (4H, m), 7.61-7.68 (2H, m), 7.82-7.84 (4H, m), 10.72 (1H, brs). $^{13}$C NMR (100 MHz, CDCl$_3$) δ 197.8, 172.4, 151.8, 137.9, 137.1, 133.0, 130.6, 129.6, 129.3, 129.1, 128.7, 127.6, 120.7, 108.7, 77.7, 58.7, 35.2, 9.9 HRMS m/z 426.1819, (M+H)$^+$ calcd for [C$_{26}$H$_{24}$N$_3$O$_3$]$^+$: 426.1812. IR (neat) 2928, 1655, 1446, 1277, 1162, 919, 697.

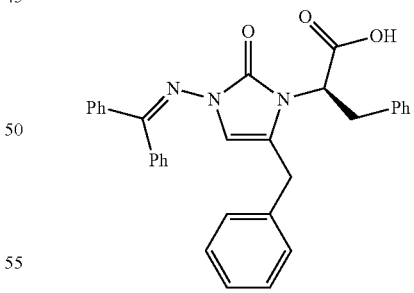

(2'R)-1-((Diphenylmethylene)amino)-3-(tert-butyl-3'-phenyl-2'-propanoate)-4-benzylimidazolin-2-one (26a)

tert-Butyl ester 24a (174 mg, 0.31 mmol) was treated under the same conditions to prepare acid 4 to provide acid 26a as a yellow oil (164 mg, >99%): R$_f$ 0.64 (8:2 EtOAc:hexanes); [α]$_D^{20}$ 36.8 (c 0.87, CHCl$_3$); $^1$H NMR (400 MHz, CDCl$_3$) δ 2.98 (2H, dd, J=16.1, 57.6 Hz), 3.38-3.56 (2H, m), 4.40-4.56

(1H, m), 5.77 (1H, d, 25.5 Hz), 6.70-7.85 (20H, m), 10.53 (1H, brs). $^{13}$C NMR (100 MHz, CDCl$_3$) δ 197.9, 172.3, 172.0, 157.4, 157.0, 151.9, 137.9, 137.3, 134.8, 133.1, 130.6, 129.9, 129.4, 129.3, 129.2, 129.0, 128.8, 127.7, 124.3, 117.2, 114.4, 109.9, 58.9, 35.4, 35.3, 30.8. HRMS m/z 502.2124, (M+H)$^+$ calcd for [C$_{32}$H$_{28}$N$_3$O$_3$]: 502.2125. IR (neat) 3028, 1655, 1447, 1277, 1162, 919, 696.

[N-Amino-4-methylimidazolin-2-one$^4$]GHRP-6
(His-D-Trp-Ala-(N-amino-4-methyl-imidazolin-2-
one)-D-Phe-Lys-NH$_2$, 31a)

LCMS (5-80% MeOH, 20 min) R.T.=7.09 min; (5-80% MeCN, 20 min) R.T.=7.11 min; HRMS Calcd m/z for C$_{39}$H$_{52}$N$_{12}$O$_6$ [M+2H]$^{+2}$ 392.2061. Found 392.2075.

[N-Amino-4-benzylimidazolin-2-one$^4$]GHRP-6
(His-D-Trp-Ala-(N-amino-4-benzyl-imidazolin-2-
one)-D-Phe-Lys-NH$_2$, 31b)

LCMS (5-80% MeOH, 20 min) R.T.=8.80 min; (5-80% MeCN, 20 min) R.T.=8.19 min; HRMS Calcd m/z for C$_{45}$H$_{55}$N$_{12}$O$_6$ [M+H]$^+$ 859.4362. Found 859.4364.

N-Amino imidazolin-2-one peptide mimic 31a was shown to be an inseparable mixture of diasterioisomers, coming from racemization at the Phe position during the synthesis of dipeptide building block 3. Subsequently, enantiomerically pure R- and S-3 were prepared from the mixture using supercritical fluid chromatography (SFC) preparative Chiralpak™ AD-H, 21 mm×250 mm, column as chiral stationary phase. After ester removal, employment of enantiomerically pure acids R- and S-4 in the peptide synthesis protocol provided respectively [4-Me-imidazolin-2-one$^4$]GHRP-6 and its L-Phe counterpart R- and S-31a in 6% and 4% overall yields and >99% purity after isolation by reverse-phase HPLC.

(2'S)-1-((Diphenylmethylene)amino)-3-(tert-butyl-3'-
phenylpropanoate)-4-methyl-imidazolin-2-one (S-3)
and (2'R)-1-((Diphenylmethylene)amino)-3-(tert-
butyl-3'-phenylpropanoate)-4-methyl-imidazolin-2-
one (R-3)

A solution of benzhydrylidene aza-propargylglycinyl-D-phenylalanine tert-butyl ester 2 (1.75 g, 3.6 mmol) in 20 mL of anhydrous acetonitrile in an ice bath was treated with a suspension of NaH (60% in oil, 291 mg, 7.27 mmol) for 2 hours. After 2 h, a small volume of water was added to the mixture, which was stirred for 15 min. The volume was concentrated, and partitioned between EtOAc and brine. The aqueous layer was separated and extracted three times with EtOAc. The combined organic layers were dried over Na$_2$SO$_4$, filtered, and evaporated to a residue, which was purified by silica gel chromatography using 30% Et$_2$O in petroleum ether to give 3 as a yellow oil (941.8. mg, 54%) as a diasteriomeric mixture (e.r: 73:27). The enantiomeric ratio was determined by SFC analysis on chiral stationary phase [Chiralpak™ AD-H, 4.6 mm×250 mm, isocratic gradient 10% i-PrOH, 3 mL/min, 25° C., 150 bar, t$_r$ (minor) 13.2 min, t$_r$ (major) 17.5 min]. Separation of the enantiomers was achieved on a preparative SFC [Chiralpak™ AD-H, 21 mm×250 mm, isocratic gradient 15% i-PrOH, 60 g/min, 25° C., 150 bar, t$_r$ (minor) 13.2 min, t$_r$ (major) 17.5 min] to afford 211 mg (12% yield) of imidazolin-2-one 3a: [α]$_D^{20}$ −22.7 (c 0.9, CHCl$_3$) and 614 mg (35% yield) of imidazolin-2-one 3b: [α]$_D^{20}$ 25.3 (c 1.06, CHCl$_3$). R$_f$ 0.35 (6:4 petroleum ether: Et$_2$O); $^1$H NMR (400 MHz, CDCl$_3$) δ 1.48 (9H, s), 1.55 (3H, s), 3.36-3.42 (2H, m), 4.67-4.70 (1H, q, J=5.1, 10.4 Hz), 5.43 (1H, s), 7.09 (2H, d, J=7.3 Hz), 7.21-7.46 (11H, m), 7.64 (2H, d, J=7.8 Hz). $^{13}$C NMR (100 MHz, CDCl$_3$) δ 169.1, 163.7, 150.8, 138.2, 135.7, 130.9, 129.9, 129.6, 129.5, 129.3, 129.0, 128.8, 128.4, 127.0, 119.0, 106.2, 82.7, 77.7, 57.6, 35.9, 28.4, 11.1. HRMS m/z 482.2440, (M+H)$^+$ calcd for [C$_{30}$H$_{32}$N$_3$O$_3$]$^+$: 482.2438. IR (neat) 1694, 1445, 1392, 1276, 1152, 747, 693.

(2'S)-1-(Diphenylmethylene)amino)-3-(3-phenyl-2-
propanoate)-4-methylimidazolin-2-one (S-4) and
(2'R)-1-((Diphenylmethylene)amino)-3-(3(phenyl-2'-
propanoate)-4-methylimidazoin-2-one (R-4)

tert-Butyl ester S-3 (211 mg, 0.44 mmol) was dissolved in 8 ml of a 1:1 DCM:TFA and stirred for 5 h. The volatiles were removed by evaporation under reduced pressure and the residue was dissolved in DCM and concentrated to remove residual TFA to give acid S-4 as brown oil (187 mg, >99%): [α]$_D^{20}$ −10.4 (c 1.04, CHCl$_3$); R$_f$ 0.24 (1:9 MeOH:DCM); $^1$H NMR (400 MHz, CDCl$_3$) δ 1.50 (3H, s), 3.47 (2H, d, J=7.6 Hz), 4.51 (1H, t, J=7.6 Hz), 6.07 (1H, s), 7.13 (2H, d, J=7.1 Hz), 7.19-7.32 (3H, m), 7.46-7.53 (4H, m), 7.61-7.68 (2H, m), 7.82-7.84 (4H, m), 10.72 (1H, brs). $^{13}$C NMR (100 MHz, CDCl$_3$) δ 197.8, 172.4, 151.8, 137.9, 137.1, 133.0, 130.6, 129.6, 129.3, 129.1, 128.7, 127.6, 120.7, 108.7, 77.7, 58.7, 35.2, 9.9 HRMS m/z 426.1819, (M+H)$^+$ calcd for [C$_{26}$H$_{24}$N$_3$O$_3$]$^+$: 426.1812. IR (neat) 2928, 1655, 1446, 1277, 1162, 919, 697. Acid R-4 was obtained using the same protocol on tert-butyl ester R-3 and isolated in the same yield: [α]$_D^{20}$ 10.0 (c 1.15, CHCl$_3$).

Peptides S- and R-31a were prepared using enantiomerically pure acids S- and R-4 and the same protocols used to make 31a.

[N-Amino-4-methylimidazolin-2-one$^4$]GHRP-6
(His-D-Trp-Ala-(N-amino-4-methyl-imidazolin-2-
one)-L-Phe-Lys-NH$_2$, (S-31a)

Yield: 4%. LCMS (5-90% MeOH, 12 min) R.T.=8.1 min; (5-90% MeCN, 12 min) R.T.=8.1 min; $^1$H NMR (700 MHz, DMSO-d$_6$) δ 1.22 (1H, d, J=7.14 Hz) 1.25-1.38 (3H, m), 1.46-1.63 (5H, m), 1.65-1.67 (1H, m), 1.74-1.81 (2H, m), 2.12 (1H, s), 2.43-2.45 (1H, m), 2.62-2.65 (1H, m), 2.77 (1H, d, J=0.61 Hz), 2.77-2.86 (3H, m), 2.93 (1H, brs), 3.01-3.08 (2H, m), 3.12-3.17 (m, 2H), 4.17-4.27 (2H, m), 4.38-4.47 (2H, m), 4.60-4.67 (2H, m), 4.69-4.80 (2H, m), 6.10 (1H, brs), 6.78 (1H, brs), 6.99-7.02 (1H, m), 7.07-7.10 (2H, m), 7.12-7.18 (2H, m), 7.18-7.23 (2H, m), 7.24-7.28 (1H, m), 7.34-7.37 (1H, m), 7.43 (1H, brs), 7.58-7.64 (2H, m), 7.87 (1H, d, J=8.43 Hz), 7.99 (1H, s), 8.32 (2H, s), 8.71 (1H, d, J=7.55 Hz), 10.90 (1H, brs). HRMS Calcd m/z for C$_{39}$H$_{52}$N$_{12}$O$_6$ [M+2H]$^{+2}$ 392.2061. Found 392.2080; Calcd m/z for C$_{39}$H$_{50}$N$_{12}$NaO$_6$ [M+Na]$^+$ 805.3868. Found 805.3882.

[N-Amino-4-methylimidazolin-2-one[4]]GHRP-6 (His-D-Trp-Ala-(N-amino-4-methyl-imidazolin-2-one)-D-Phe-Lys-NH$_2$ (R-31a)

Yield: 6%. LCMS (5-90% MeOH, 12 min) R.T.=8.1 min; (5-90% MeCN, 12 min) R.T.=8.1 min; $^1$H NMR (700 MHz, DMSO-d) δ 1H NMR (700 MHz, DMSO-d) δ 1.23 (1H, d, J=7.10 Hz) 1.25-1.39 (3H, m), 1.46-1.63 (4H, m), 1.65-1.67 (1H, m), 1.75-1.83 (2H, m), 2.12 (1H, s), 2.43-2.45 (1H, m), 2.62-2.65 (1H, m), 2.77 (1H, d, J=0.56 Hz), 2.77-2.81 (1H, m), 2.82-2.86 (1H, m), 2.93 (1H, brs), 3.01-3.07 (2H, m), 3.11-3.17 (m, 2H), 4.17-4.22 (2H, m), 4.38-4.44 (2H, m), 4.63-4.68 (2H, m), 4.68-4.73 (2H, m), 6.11 (1H, brs), 6.78 (1H, brs), 6.99-7.02 (2H, m), 7.07-7.12 (2H, m), 7.16 (1H, brs), 7.19-7.27 (3H, m), 7.35 (1H, d, J=8.31 Hz), 7.43 (1H, brs), 7.59-7.63 (2H, m), 7.99 (1H, s), 8.10 (1H, d, J=8.11 Hz), 8.28 (1H, brs), 8.33-8.39 (2H, m), 8.66 (1H, d, J=7.72 Hz), 10.89 (1H, brs). HRMS Calcd m/z for $C_{39}H_{52}N_{12}O_6$ $[M+2H]^{+2}$ 392.2061. Found 392.2077; Calcd m/z for $C_{39}H_{50}N_{12}NaO_6$ $[M+Na]^+$ 805.3868. Found 805.3877.

Production of [N-amino-4-methyl-5-arylimidazol-2-one[4]]GHRP-6 analogs

In the interest of expanding the diversity of the side-chain substituent on the N-amino imidazol-2-one structure, the arylation of the 5-position of 1-amino-4-methyl-imidazolidin-2-one-containing peptides was examined in solution and on solid phase. The direct C—H functionalization of imidazolinone was previously achieved with Pd(OAc)$_2$/NaOAc in DMSO (see: Jianming Lu, Xianghui Tan, and Chuo Chen, Palladium-Catalyzed Direct Functionalization of Imidazolinone: Synthesis of Dibromophakellstatin. J. Am. Chem. Soc. 2007, 129, 7768-7769). Although this precedent was encouraging, the influence of substituents on the imidazolinone remained to be investigated. Initially, (2'RS)-1-((diphenylmethylene)amino)-3-(tert-butyl-3'-phenyl-2'-propanoate)-4-methyl-imidazol-2-one was employed to evaluate the potential for palladium catalyzed arylation under similar conditions in solution. Arylation at the C5 position of the ring of the 4-methyl-imidazolidin-2-one dipeptide with p-iodotoluene (3 equiv.) was best achieved using sodium acetate (3 equiv.) as base and Pd(OAc)$_2$ as catalyst in DMSO at 80° C. for 16 h, which provided (2'RS)-1-((diphenylmethylene) amino)-3-(tert-butyl-3'-phenyl-2'-propanoate)-4-methyl-5-(p-toluoyl)imidazol-2-one (DND-B2-131) in 78% yield after purification by chromatography. Similarly, (2'S)-1-((diphenylmethylene)amino)-3-(3'-phenyl-N'-isopropyl-2'-propionamide)-4-methyl-5-(p-nitrophenyl)imidazol-2-one (DND-B1-133) was synthesized in 79% yield by employing the optimized palladium catalyzed conditions using (2'S)-1-((diphenylmethylene)amino)-3-(3'-phenyl-N'-isopropyl-2'-propionamide)-4-methyl-imidazol-2-one and p-nitrophenyl iodide. With methodology established in solution, attention was turned directly towards the C5-arylation of imidazolidin-2-one-containing peptides bound to a solid support. Towards this goal, N-((diphenylmethylene)amino-4-methyl-imidazol-2-one)-DL-Phe-Lys-amide linked to Rink resin was treated with a series of aryl iodides (3 equiv.) in presence of sodium acetate (3 equiv.) and palladium acetate (0.1 equiv.) to examine the percent conversion to arylated tripeptide analogs (Table 2). After removal of the hydrazone moiety using hydroxylamine in pyridine, peptide elongation using Fmoc-Ala, Fmoc-D-Trp(Boc) and Boc-His(Boc), resin cleavage and purification by HPLC, a series of [N-amino-4-methyl-5-arylimidazol-2-one[4]]GHRP-6 analogs was produced: DND-B2-109, DND-B3-1, DND-B3-3, DND-B3-5, DND-B3-7.

An alternative approach for synthesizing N-amino cyclic urea peptide mimics was developed based on alkylation of a suitably protected aza-glycinyl dipeptide ester with a dihaloalkane in solution, ester cleavage and application of the resulting building block in solid-phase peptide synthesis. For example, N-amino imidazolidin-2-one and tetrahydropyrimidin-2-one dipeptides DND-B2-149 and DND-B2-147 were respectively prepared from alkylation of benzhydrylidene azaglycinyl-D-phenylalanine tert-butyl ester using 1,2-dibromoethane and 1-bromo-3-chloropropane with tetrabutylammonium hydroxide as base. In the former case, alkylation provided N-amino cyclic urea dipeptide ester DND-B2-149, which on treatment with trifluoroacetic acid provide the corresponding dipeptide acid, which was introduced into [N-amino-imidazolidin-2-one[4]]GHRP-6 (His-D-Trp-Ala-(N-amino-imidazolidin-2-one)-D-Phe-Lys-NH$_2$, DND-B2-185). In the latter case, benzhydrylidene aza-(3-chloropropyl)glycinyl-D-phenylalanine tert-butyl ester (DND-B2-139) was isolated from the alkylation reaction and then treated with silver trifluoromethansulfonate to cause cyclization and simultaneous ester cleavage to afford tetrahydropyrimidin-2-one dipeptide acid DND-B2-147, which may similarly be introduced into peptide structures. Notably, the application of 1-bromo-3-chloropropane and related dihaloalkanes in the alkylation of related glycine Schiff base substrates has required heating (85° C.) using relatively stronger base (BTPP) for the synthesis of -substituted lactams (see: William L. Scott, Jordi Alsina, Joseph H. Kennedy, and Martin J. O'Donnell "Solid-Phase Synthesis of Constrained Terminal and Internal Lactam Peptidomimetics" Org. Lett., 2004, 6 (10), pp 1629-1632).

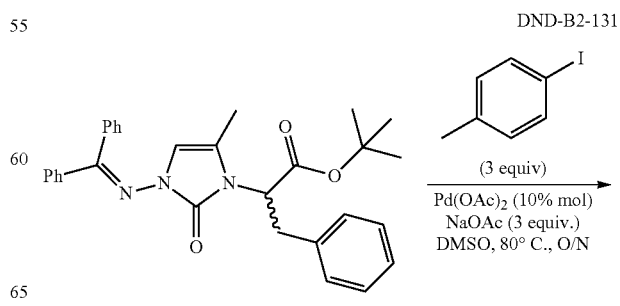

DND-B2-131

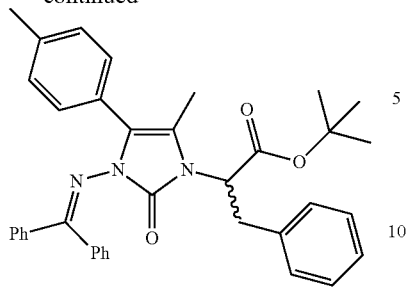

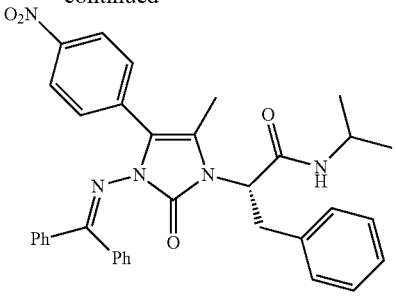

(2'RS)-1-((Diphenylmethylene)amino)-3-(tert-butyl-3'-phenyl-2'-propanoate)-4-methyl-5-(p-toluoyl)imidazol-2-one (DND-B2-131)

(2'RS)-1-((Diphenylmethylene)amino)-3-(tert-butyl-3'-phenyl-2'-propanoate)-4-methyl-imidazolidin-2-one (100 mg, 0.21 mmol) and sodium acetate (51.1 mg, 0.64 mmol) were added to a 3 mL vial containing 1 mL of degassed DMSO, and treated with p-iodotoluene (83 μL, 0.64 mmol). The vial was purged with argon for 2 min, heated to 80° C. and the contents were stirred for 16 h. The reaction mixture was partitioned between EtOAc and brine. The organic layer was washed with brine, dried over MgSO$_4$ and concentrated under reduced-pressure to a residue, which was purified by silica chromatography using 15% EtOAc in hexanes. Evaporation of the collected fractions gave DND-B2-131 as yellow foam (92.1 mg, 78%): Rf=0.49 (30% EtOAc in hexanes). $^1$H NMR (400 MHz, CDCl$_3$) δ 1.48 (9H, s), 1.63 (3H, s), 2.32 (3H, s), 3.36-3.43 (2H, m), 4.60-4.46 (1H, q, J=4.94, 5.77 Hz), 6.99-7.03 (4H, m), 7.05-7.11 (4H, m), 7.21-7.38 (8H, m) 7.43-7.47 (1H, m), 7.60-7.63 (2H, d, J=7.21 Hz). $^{13}$C NMR (100 MHz, CDCl$_3$) δ 174.4, 168.6, 147.82, 138.0, 137.3, 136.8, 135.4, 135.0, 129.7, 129.3, 129.0, 128.9, 128.8, 128.7, 128.4, 128.3, 127.9, 127.7, 119.2, 115.2, 82.2, 57.6, 35.5, 28.0, 21.1, 9.5. HRMS m/z 571.2837, [MH]$^+$ calcd for [C$_{37}$H$_{38}$N$_3$O$_3$]: m/z: 571.2835.

(2'S)-1-((Diphenylmethylene)amino)-3-(3'-phenyl-N'-isopropyl-2'-propionamide)-4-methyl-5-(p-nitrophenyl)imidazol-2-one (DND-B1-133) was prepared according to the representative procedure described above for the synthesis of DND-B2-131 using (2'S)-1-((diphenylmethylene)amino)-3-(tert-butyl-3'-phenyl-2'-propionamide)-4-methyl-imidazolid-2-one (100 mg, 0.21 mmol) and p-nitrophenyl iodide (160 mg, 0.64 mmol). Purification on silica gel by column chromatography was performed using 20% EtOAc in hexanes. Evaporation of the collected fractions gave DND-B1-133 as yellow foam (96 mg, 79%): Rf=0.53 (50% EtOAc in hexanes). $^1$H NMR (400 MHz, CDCl$_3$) δ 1.13-1.15 (3H, d, J=6.54 Hz), 1.18-1.20 (3H, d, J=6.64 Hz), 1.77 (3H, s), 3.30-3.34 (1H, q, J=4.56, 9.35 Hz), 3.55-3.61 (1H, m), 4.00-4.05 (1H, m), 4.50-4.54 (1H, q, J=4.38, 6.89 Hz), 7.05-7.07 (4H, m), 7.24-7.34 (7H, m), 7.38-7.44 (3H, m), 7.50-7.54 (1H, m), 7.61-7.63 (2H, m), 7.74-7.77 (1H, m), 8.13-8.16 (2H, m). $^{13}$C NMR (100 MHz, CDCl$_3$) δ 175.5, 168.9, 148.4, 146.4, 137.3, 136.5, 135.2, 134.9, 129.8, 129.1, 129.0, 128.6, 128.5, 128.3, 127.0, 123.6, 119.0, 118.4, 77.2, 41.8, 35.5, 22.5, 22.4, 9.8. MS: 588.3, [MH]$^+$ calcd for [C$_{35}$H$_{34}$N$_5$O$_4$]: m/z: 588.3.

Arylation of N-((diphenylmethylene)amino-4-methyl-imidazol-2-one)-DL-Phe-Lys-amide linked to Rink resin N-((Diphenylmethylene)amino-4-methyl-imidazol-2-one)-DL-Phe-Lys-amide linked to Rink resin (100 mg, 0.42 mmol/g) in a 3 mL vial containing a suspension of sodium acetate (10.3 mg, 0.126 mmol) in degassed DMSO (1 mL), was treated respectively with iodobenzene (14 μL, 0.126 mmol), 3-iodobenzotrifluoride (18.5 μL, 0.126 mmol), iodotoluene (27.5 mg, 0.126 mmol), ethyl 4-iodobenzoate (21 μL, 0.126 mmol), 1-iodo-4-nitrobenzene (31.3 mg, 0.126 mmol), 4-iodoanisole (29.5 mg, 0.126 mmol), 1-fluoro-4-iodobenzene (14.5 μL, 0.126 mmol), 1-iodonaphthalene (18.4 μL, 0.126 mmol), 4-iodo-1-trityl-imidazole (54.9 mg, 0.126 mmol), or 1-Boc-3-iodo-indole (42.4 mg, 0.126 mmol). The vial was purged with argon for 2 min, and the suspension was gently stirred at 80° C. for 16 h. The resin was filtered, washed twice with a mixture of DMF:AcOH:H$_2$O (v/v/v 7:2:1), followed by DCM (3×3 mL), MeOH (3×3 mL), and DCM (3×10 mL). An aliquot of resin (10 mg) was cleaved with TFA:TES (v/v: 98:2) and the residue was examined by LCMS. Conversion was ascertained by comparison of the peak area corresponding to mass of the desired product versus the peak area corresponding to mass of the starting peptide.

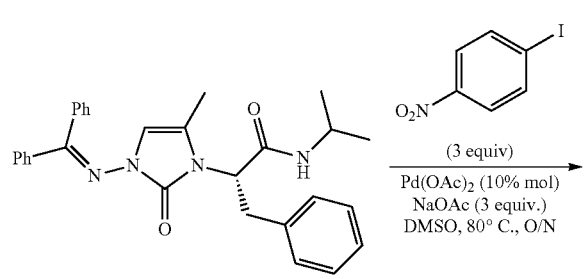

DND-B1-133

TABLE 2

Arylation of N-amino-imidazolin-2-one peptide on Rink amide resin

| No | Ar—I | Conversion (%)* |
|---|---|---|
| 1 | iodobenzene | 66 |
| 2 | 1-iodo-3-(trifluoromethyl)benzene | 45 |
| 3 | 4-iodotoluene | 75 |
| 4 | ethyl 4-iodobenzoate | 46 |
| 5 | 1-iodo-4-nitrobenzene | 57 |
| 6 | 4-iodoanisole | 69 |
| 7 | 1-fluoro-4-iodobenzene | 42 |
| 8 | 1-iodonaphthalene | 62 |
| 9 | 2-iodo-N-trityl-imidazole | No Reaction |
| 10 | N-Boc-3-iodoindole | No Reaction |

*reaction conversion was ascertained by LC-MS analysis of cleaved material.

Solid-phase synthesis of [N-amino-4-methyl-5-arylimidazolin-2-one⁴]GHRP-6 analogs The hydrazone was removed from the N-(((diphenylmethylene)amino-4-methyl-5-arylimidazol-2-one)-DL-Phe-Lys-amide linked to Rink resin using 1.5 M NH₂OH.HCl in pyridine. The resin was filtered and washed twice with 5% triethylamine in DMF and then DCM (3×), MeOH (3×) and DCM (3×). The resulting semicarbazides were acylated with Fmoc-Ala (6 equiv.) using DIC (3 equiv.). Elongation of the peptide by Fmoc deprotections, resin washings and coupling of Fmoc-D-Trp(Boc) and Boc-His(Boc) gave the final resin bound peptides, which were cleaved with TFA:TES:H₂O (v/v/v: 95:2.5:2.5) and precipitated in diethyl ether. The precipitated material was purified by preparative RP-HPLC using a SunFire® C18-5 μm column (0-50% ACN, 60 min).

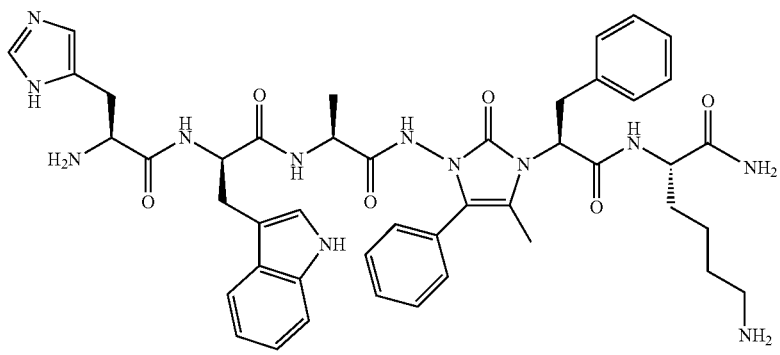

[N-Amino-4-methyl-5-phenylimidazol-2-one[4], L-Phe[5]]GHRP-6 (His-D-Trp-Ala-(N-amino-4-methyl-5-phenyl-imidazol-2-one)-L-Phe-Lys-NH$_2$, DND-B2-109)

LCMS (5-80% ACN, 20 min) R.T.=10.3 min; (5-80% MeOH, 20 min) R.T.=12.8 min; HRMS m/z calcd. for $C_{45}H_{55}N_{12}O_6$ [MH]$^+$ 859.4362. Found 859.4376.

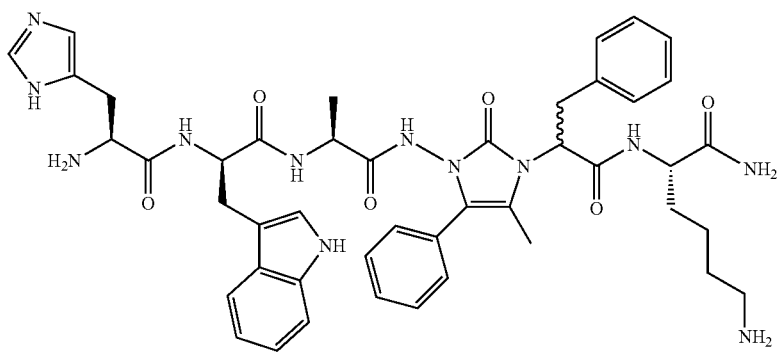

[N-Amino-4-methyl-5-phenylimidazol-2-one4, DL-Phe5]GHRP-6 (His-D-Trp-Ala-(N-amino-4-methyl-5-phenyl-imidazolin-2-one)-DL-Phe-Lys-NH2, DND-B3-01)

LCMS (5-80% ACN, 20 min) R.T.=10.3 min; (5-80% MeCN, 20 min) R.T.=12.8 min; MS m/z Calcd for C45H55N12O6 [MH]$^+$ 859.4. Found 859.4.

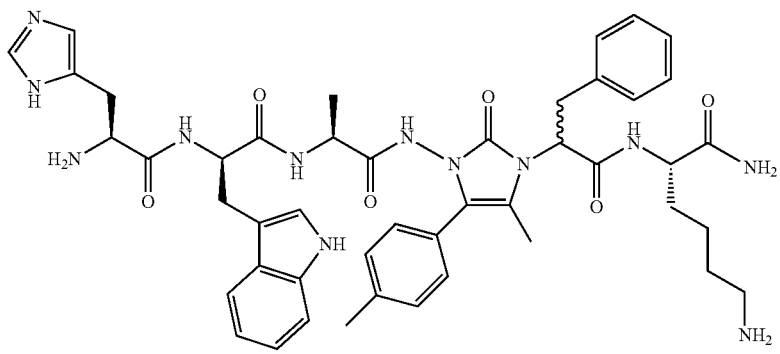

[N-Amino-4-methyl-5-p-toluoyl-imidazol-2-one⁴, DL-Phe⁵]GHRP-6 (His-D-Trp-Ala-(N-amino-4-methyl-5-p-toluoyl-imidazol-2-one)-DL-Phe-Lys-NH₂, DND-B3-03)

LCMS (5-80% ACN, 20 min) R.T.=10.4 min; (5-80% MeOH, 20 min) R.T.=12.8 min; MS Calcd for $C_{46}H_{56}N_{12}O_6$ [MH]⁺ 873.4. Found 873.4.

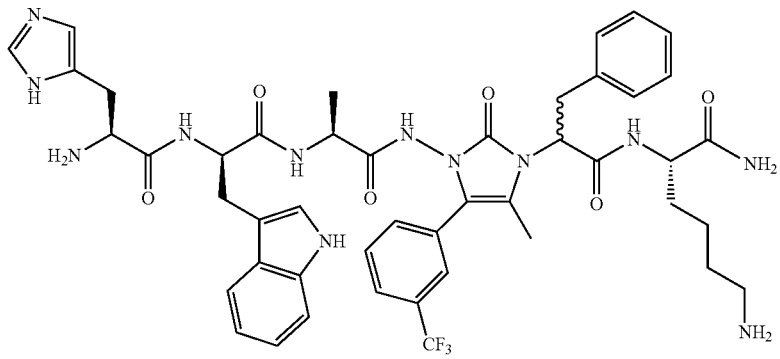

DND-B3-05

[N-Amino-4-methyl-5-m-trifluoromethylphenyl-imidazol-2-one⁴, DL-Phe⁵]GHRP-6 (His-D-Trp-Ala-(N-amino-4-methyl-5-m-trifluoromethylphenyl-imidazol-2-one)-DL-Phe-Lys-NH₂, DND-B3-05)

LCMS (5-80% MeOH, 20 min) R.T.=12.3 min; (5-80% ACN, 20 min) R.T.=10.6 min; MS Calcd for $C_{46}H_{53}F_3N_{12}O_6$ [MH]⁺ 927.4. Found 927.4.

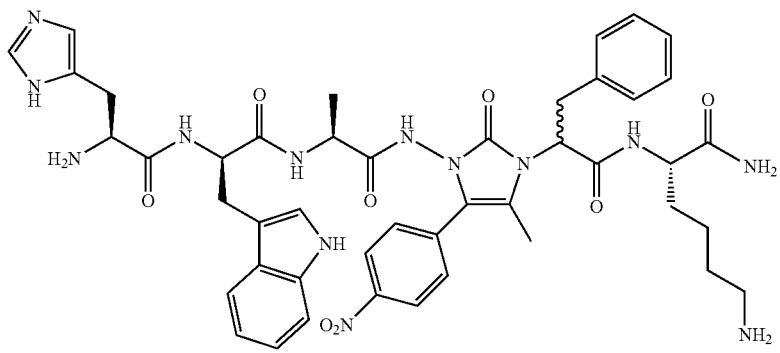

DND-B3-07

[N-Amino-4-methyl-5-p-nitrophenyl-imidazol-2-one[4], DL-Phe[5]]GHRP-6 (His-D-Trp-Ala-(N-amino-4-methyl-5-p-nitrophenyl-imidazol-2-one)-DL-Phe-Lys-NH$_2$, DND-B3-07)

LCMS (5-80% MeOH, 20 min) R.T.=12.2 min; (5-80% ACN, 20 min) R.T.=10.5 min; Calcd for C$_{45}$H$_{53}$N$_{13}$O$_8$ [MH]$^+$ 904.4. Found 904.3.

J=5.37, 4.89 Hz), 2.95-3.01 (2H, m), 3.20-3.22 (1H, m), 3.30-3.35 (1H, q, J=4.25, 8.67 Hz), 4.92-4.96 (1H, q, J=4.90, 8.17 Hz), 6.93-6.95 (1H, d, J=9.47 Hz), 7.24-7.35 (9H, m), 7.43-7.46 (3H, m), 7.51-7.53 (1H, d, J=9.54), 7.97-7.99 (1H, d, J=9.32). HRMS m/z 470.2455, [MH]$^+$ calcd for C$_{29}$H$_{31}$N$_3$O$_3$: m/z: 470.2438.

DND-B2-185

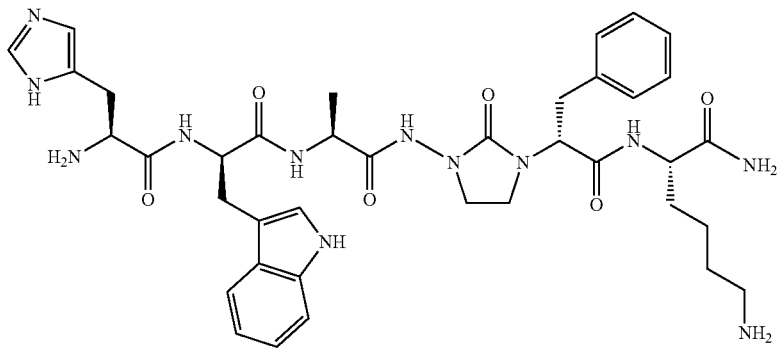

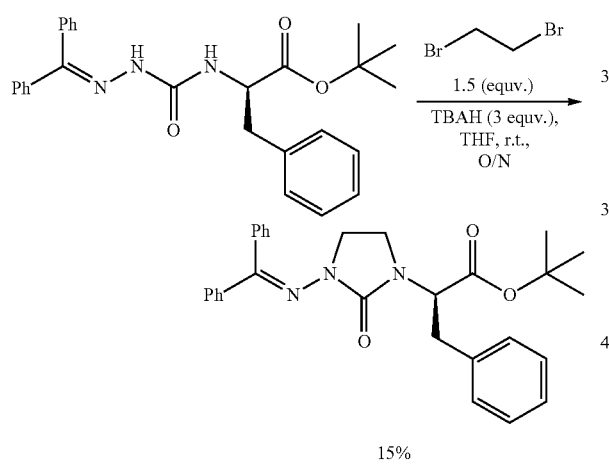

(2'R)-1-((Diphenylmethylene)amino)-3-(tert-butyl-3'-phenylpropanoate)-imidazolidin-2-one (DND-B2-149)

A solution of benzhydrylidene azaglycinyl-D-phenylalanine tert-butyl ester (1 g, 2.26 mmol) in THF (10 mL) was treated with tetrabutylammonium hydroxide (4.4 mL, 6.78 mmol), agitated for 30 min at room temperature, treated with 1,2-dibromoethane (294 µL, 3.39 mmol, pre-filtered through a pad of silica gel), agitated for 16 h, and concentrated under reduced pressure. The residue was partitioned between EtOAc and 5% aqueous citric acid. The organic phase was washed with brine, dried over MgSO$_4$, filtered and concentrated under reduced pressure to a residue, which was purified by silica chromatography using 15% EtOAc in hexanes to give imidazolidin-2-one DND-B2-149 (159 mg, 0.338 mmol; 15%) as pale yellow oil: Rf=0.4 (30% EtOAc in hexanes); $^1$H NMR (400 MHz, CDCl$_3$) δ 1.45 (9H, s), 2.88-2.91 (1H, q,

[N-Amino-imidazolidin-2-one[4]]GHRP-6 (His-D-Trp-Ala-(N-amino-imidazolidin-2-one)-D-Phe-Lys-NH$_2$, DND-B2-185)

Ester DND-B2-149 (100 mg, 0.213 mmol) was dissolved in 2 mL of a 1:1 DCM:TFA solution and stirred for 3 h. The volatiles were removed by evaporation under reduced pressure to give a brown oil (84 mg, 0.2 mmol; 95%), which was coupled to E-(Boc)lysine linked to Rink amide resin using standard conditions (HBTU, DIEA). The hydrazone was removed using NH$_2$OH.HCl in pyridine, and the resulting semicarbazide was acylated with Fmoc-Ala (6 equiv.) using DIC (3 equiv.) to give the corresponding tetrapeptide resin. After Fmoc deprotections, resin washings and couplings of Fmoc-D-Trp and Boc-His(Boc), the resulting resin was cleaved with TFA:TES:H$_2$O (v/v/v: 95:2.5:2.5) and precipitated in diethyl ether. The precipitate was purified by preparative RP-HPLC using a SunFire® C18-5 µm column (0-50% ACN, 60 min). [N-Amino-imidazolidin-2-one[4]]GHRP-6 (His-D-Trp-Ala-(N-amino-imidazolidin-2-one)-D-Phe-Lys-NH$_2$, DND-B2-185). LCMS (5-80% MeOH, 20 min) R.T.=11.7 min; (5-80% ACN, 20 min) R.T.=9.0 min; MS Calcd for C$_{38}$H$_{50}$N$_{12}$O$_6$ [M]$^+$ 771.4. Found [MH]$^+$ 771.3.

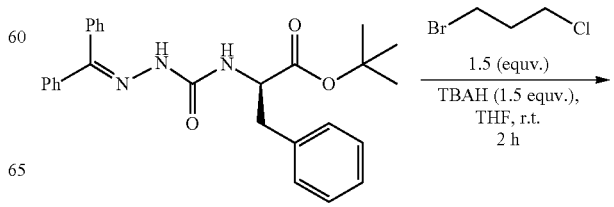

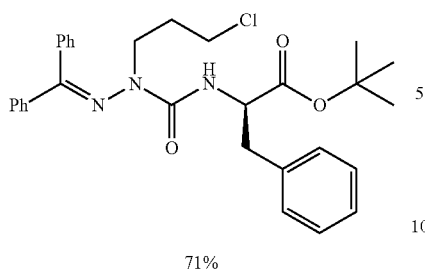

71%

Benzhydrylidene aza-(3-chloropropyl)glycinyl-D-phenylalanine tert-butyl ester (DND-B2-139)

A solution of benzhydrylidene azaglycinyl-D-phenylalanine tert-butyl ester (200 mg, 0.45 mmol) in THF (2 mL) was treated with tetrabutylammonium hydroxide (876 mg, 1.35 mmol), agitated for 30 min at room temperature, treated with 1-bromo-3-chloropropane (67 μL, 0.68 mmol, pre-filtered through a pad of silica gel), agitated for 2 h, and partitioned between EtOAc and 5% aqueous citric acid. The organic phase was washed with brine, dried over MgSO$_4$, filtered and concentrated under reduced-pressure to a residue, which was purified by chromatography on silica gel using 15% EtOAc in hexanes to give ester DND-B2-139 as pale yellow oil (166 mg, 0.32 mmol; 71%): Rf=0.58 (30% EtOAc in hexanes). $^1$H NMR (400 MHz, CDCl$_3$) δ 1.46 (9H, s), 1.72-1.75 (2H, m), 3.11-3.23 (2H, m), 3.28-3.32 (2H, m), 3.34-3.36 (1H, m), 3.40-3.45 (1H, m), 4.74-4.77 (1H, m), 6.83-6.85 (1H, d, J=8.46 Hz), 6.90-6.92 (1H, m), 7.22-7.32 (7H, m), 7.37-7.40 (2H, m), 7.45-7.51 (5H, m), 8.12-8.15 (1H, m). $^{13}$C NMR (100 MHz, CDCl$_3$) δ 171.4, 163.1, 158.4, 138.0, 136.3, 136.1, 130.5, 130.1, 129.5, 128.9, 128.7, 128.5, 127.0, 126.1, 115.6, 82.3, 54.9, 44.2, 42.3, 38.5, 29.9, 28.0. HRMS m/z calcd for $C_{30}H_{35}ClN_3O_3$ 520.2362. Found 520.2372.

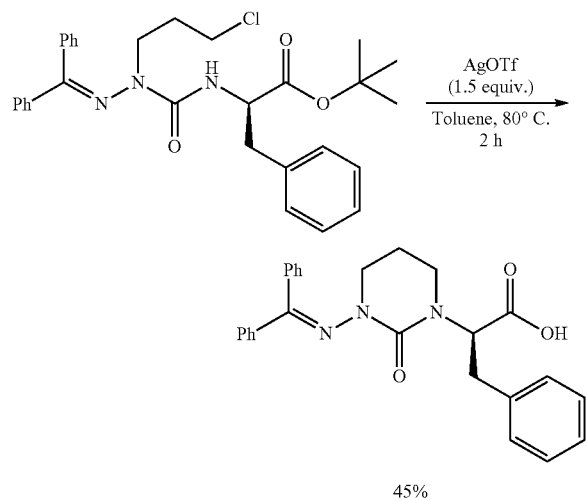

45%

(2'R)-1-((Diphenylmethylene)amino)-3-(3'-phenyl-2'-propanoate)-tetrahydropyrimidin-2-one (DND-B2-147)

A solution of ester DND-B2-139 (100 mg, 0.192 mmol) in toluene (5 mL) was treated with AgOTf (74.1 mg, 0.29 mmol), agitated for 3 h at 80° C., cooled to room temperature, and filtered. The filtrate was evaporated under reduced pressure to give a colorless oil, which was purified by preparative HPLC using a Phenomenex® C18 Gemini column (30-80% ACN, 60 min). Evaporation of the collected fractions gave DND-B2-147 (54.8 mg, 0.13 mmol; 45%). $^1$H NMR (400 MHz, CDCl$_3$) δ 1.78-1.79 (1H, m), 1.93-1.94 (1H, m), 2.98-3.05 (2H, m), 3.07-3.11 (1H, m), 3.40-3.45 (1H, q, J=4.34, 8.25 Hz), 3.95-3.99 (1H, m), 4.22-4.26 (1H, m), 4.63-4.67 (1H, m), 6.94-6.95 (2H, d, J=7.64 Hz), 7.18-7.29 (7H, m), 7.37-7.42 (1H, m), 7.50-7.60 (4H, m), 8.02-8.03 (2H, d, J=7.84 Hz). $^{13}$C NMR (100 MHz, CDCl$_3$) δ 173.8, 164.0, 156.0, 140.2, 136.5, 135.0, 133.0, 131.6, 129.8, 129.5, 128.7, 128.2, 127.3, 126.0, 115.9, 69.0, 57.2, 47.6, 38.5, 21.0. HRMS m/z calcd for $C_{26}H_{25}N_3O_3$ [M]$^+$ 428.1968. Found 428.1969.

Synthesis of 5-alkyl-N-amino-imidazolin-2-one and imidazolidin-one analogs

To prepare both 5-alkyl-N-amino-imidazolin-2-one and imidazolidin-one analogs, the 5-exo-dig cyclization of the hydrazone nitrogen onto the acetylene group of aza-glycinyl-N'-propargyl dipeptide 41 was examined (Scheme 1). N-Propargylation of L-phenylalanine tert-butyl ester with propargyl bromide was achieved in 83% yield using LiOH as base in DMF (see: Cho, J. H. and B. M. Kim, "LiOH-mediated N-monoalkylation of a-amino acid esters and a dipeptide ester using activated alkyl bromides" Tetrahedron Lett. 2002, 43 1273-1276). Benzhydrylidene azaglycinyl-N-propargyl-L-phenylalanine tert-butyl ester (42) was subsequently prepared in 95% yield by activation of benzophenone hydrazone using N,N'-disuccinimidyl carbonate, followed by acylation of amino ester 41. Under mild homogeneous gold catalysis conditions (see: Chiu, S. K.; et al., "Attempted Synthesis of a Keto Diazene: Reactions of Propargylic Amines, Sulfamides, and Ureas" J. Org. Chem., 1978, 43, 61-65), the electron-deficient semicarbazone nitrogen reacted onto the acetylene in the 5-exo-dig cyclization to afford methylidene-imidazolidin-2-one 43. Employing palladium-on-carbon as catalyst, both hydrogenation of the exocyclic double bond as well as olefin migration was observed to respectively prepare (5SR, 2'S)-1-((diphenylmethylidene)amino)-3-(tert-butyl-3'-phenyl-2'-propanoate)-5-methyl-imidazolidin-2-one (44) and (2'S)-1-((diphenylmethylene)-amino)-3-(tert-butyl-3'-phenyl-2'-propanoate)-4-methyl-imidazolin-2-one (45). From the same reaction mixture, the former 44 was isolated as a 3:2 diastereomeric mixture in 54% yield, and the latter 45 was obtained in 26% yield. As previously described for the 4-methyl-N-amino-imidazolin-2-one and N-amino-imidazolidin-2-one dipeptides 3 and DND-B2-149, the tert-butyl ester may be cleaved from 44 and 45 to provide constrained dipeptide building blocks for the synthesis of 5-alkyl-N-amino-imidazolin-2-one and imidazolidin-one peptides.

Scheme 1: Synthesis of 5-alkyl-N-amino-imidazolin-2-one and 5-alkyl-N-amino-imidazolidin-one dipeptides 44 and 45.

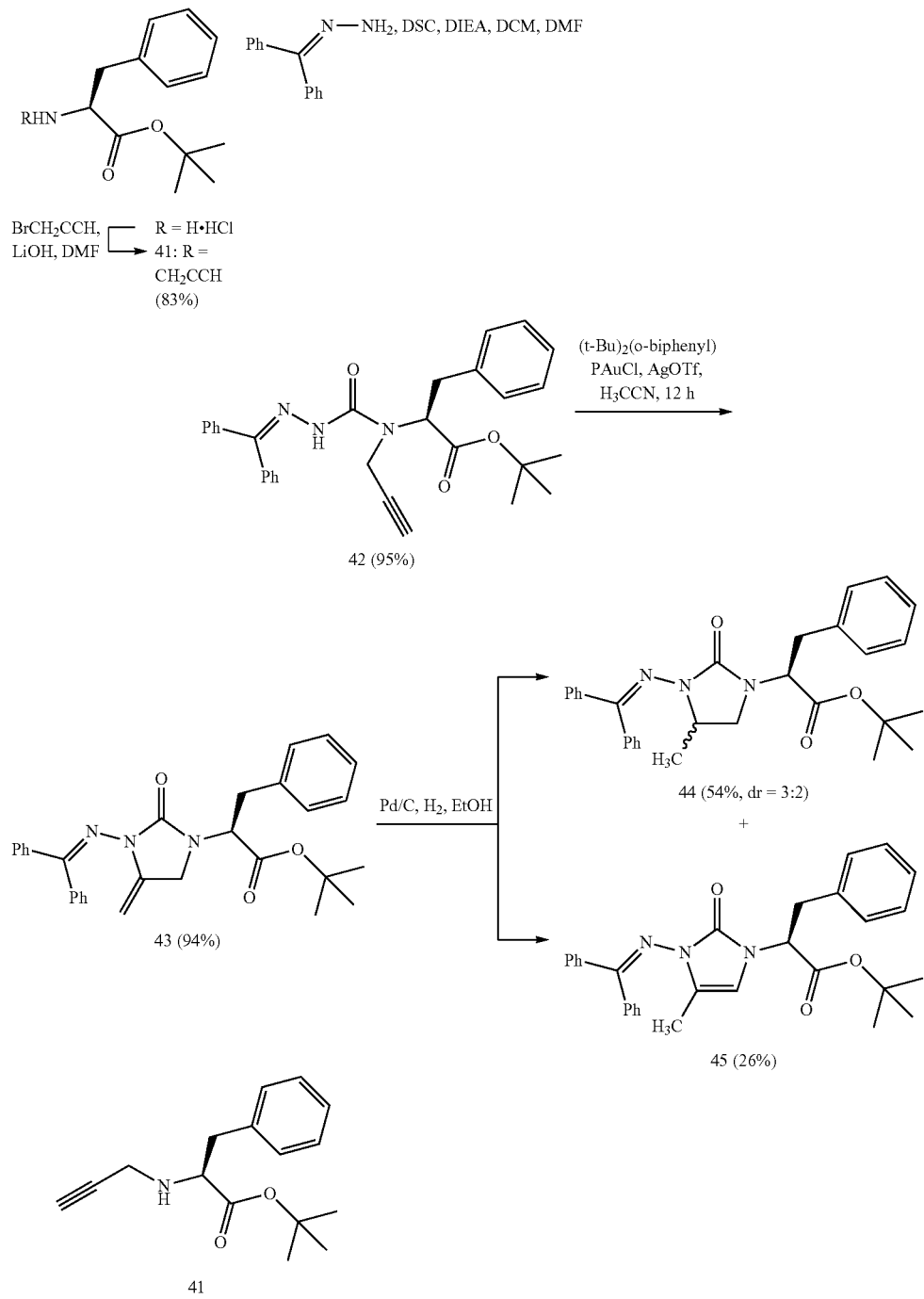

N-Propargylphenylalanine tert-butyl ester (41)

A solution of LiOH (400 mg, 16.7 mmol, 2.15 eq) in dry DMF (44 mL) containing activated 4 Å molecular sieves was stirred vigorously for 20 min, treated with Phe-Ot-Bu*HCl (2 g, 7.76 mmol, 1 eq), stirred for 45 min, treated with a solution 80% propargyl bromide (1.4 mL, 9.4 mmol, 1.21 eq) in toluene, stirred for 16 h and filtered through a pad of Celite™, which was washed with EtOAc (Cho, J. H. and B. M. Kim, Tetrahedron Lett. 2002, 43 1273-1276). The filtrate was washed three times with water, dried over MgSO$_4$ and the volatiles were evaporated to provide an oil, which was purified by chromatography on silica gel using 30% EtOAc in hexane as eluent. Evaporation of the collected fractions gave ester 41 as yellow oil (1.66 g, 83%): R$_f$=0.53 (8:2 hexane/EtOAc); $^1$H NMR (400 MHz, CDCl$_3$) δ 7.32-7.28 (m, 2H), 7.24 (m, 3H), 3.62 (t, J=6.9 Hz, 1H), 3.47-3.36 (m, 2H), 2.96 (m, 2H), 2.20 (m, 1H), 1.77 (s, 1H), 1.39 (s, 9H); $^{13}$C NMR (300 MHz, CDCl$_3$) δ 172.9, 137, 129.2, 128.1, 126.4, 81.3, 81.0, 71.6, 61.5, 39.4, 36.5, 27.8. IR (thin film) v 3297, 2981, 2942, 1723, 1370, 1152, 700 cm$^{-1}$; HRMS (LC-ESI) m/z calcd for C$_{16}$H$_{22}$NO$_2$ [MH]$^+$ 260.1645. Found 260.1634.

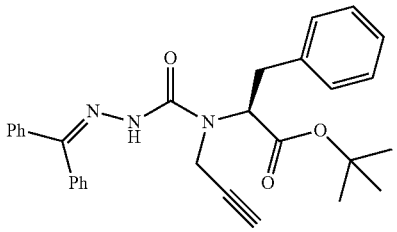

42

Benzhydrylidene Azaglycinyl-N-propargyl-L-phenylalanine tert-Butyl Ester (42)

In a flame dried round-bottom flask, a 0° C. solution of N,N'-disuccinimidyl carbonate (DSC, 1.8 g, 7.04 mmol, 1.1 eq) in dry CH$_2$Cl$_2$ (20 mL) and DMF (4 mL) was treated drop-wise by cannula with a 0° C. solution of benzophenone hydrazone (1.26 g, 6.40 mmol, 1 eq) in dry CH$_2$Cl$_2$ (28 mL). The ice-bath was removed and the reaction mixture was allowed to warm to room temperature. After stirring for 1 h, the mixture was cooled to 0° C., treated drop-wise by cannula with a premixed 0° C. solution of N-propargyl-L-Phe-Ot-Bu (41, 1.66 g, 6.40 mmol, 1 eq) and DIEA (1.1 mL, 6.40 mmol, 1 eq) in CH$_2$Cl$_2$ (8 mL), and the ice-bath was removed. The reaction mixture was allowed to warm to room temperature and stirred for 16 h. The volatiles were evaporated to a residue, which was purified on silica gel using flash chromatography with a gradient of 10-50% EtOAc in hexane as solvent system. Ester 42 was obtained as a white solid (2.93 g, 95% yield): mp 58-60° C.; R$_f$=0.44 (7:3 hexane/EtOAc); $^1$H NMR (400 MHz, CDCl$_3$) δ 8.45 (s, 1H), 7.65-7.62 (m, 2H), 7.58-7.51 (m, 3H), 7.35-7.22 (m, 10H), 4.97 (t, J=7.9 Hz, 1H), 3.95 (dd, J=2.4, 18.5 Hz, 1H), 3.87 (dd, J=2.4, 18.7 Hz, 1H), 3.23 (dd, J=7.3, 14.0 Hz, 1H), 3.06 (dd J=8.5, 14.2 Hz, 1H), 188 (t, J=2.3 Hz, 1H), 1.38 (s, 9H); $^{13}$C NMR (300 MHz, CDCl$_3$) δ 170.0, 154.3, 151.0, 136.8, 136.7, 132.4, 129.5, 129.2, 128.9, 128.8, 128.1, 128.0, 127.7, 127.2, 126.3, 81.6, 78.0, 73.2, 60.4, 35.7, 35.1, 27.5. IR (thin film) 3295, 2980, 1731, 1687, 1493, 1230, 1152, 1059, 1035, 694 cm$^{-1}$; HRMS (LC-ESI) m/z calcd for C$_{30}$H$_{32}$N$_3$O$_3$ [MH]$^+$ 482.2438. Found 482.2429.

43

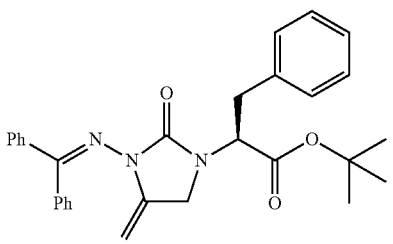

(2'S)-1-((Diphenylmethylene)amino)-3-(tert-butyl-3'-phenyl-2'-propanoate)-5-methylidene-imidazolidin-2-one (43)

Aza-dipeptide 42 (200 mg, 0.41 mmol, 1 eq) in dry acetonitrile (4 mL), was treated with (t-Bu)$_2$(O-biphenyl)PAuCl and AgOTf (10.7 mg, 0.04 mmol, 0.1 eq), and stirred for 16 h. The volatiles were evaporated. The residue was purified by flash chromatography using 10-30% EtOAc in hexane as eluent. Evaporation of the collected fraction gave imidazolidin-2-one 43 as clear oil (189 mg, 94%): R$_f$=0.29 (9:1 hexane/EtOAc); $^1$H NMR (400 MHz, CDCl$_3$) δ 7.70 (m, 2H), 7.47-7.25 (m, 11H), 7.11 (m, 2H), 4.90 (m, 1H), 4.60 (dd, J=6.4, 9.7 Hz, 1H), 4.36 (d, J=13.6 Hz, 1H), 4.31 (m, 1H), 4.14 (d, J=13.3 Hz, 1H), 3.18 (dd, J=6.3, 14.7 Hz, 1H), 2.98 (dd, J=9.7, 14.3 Hz, 1H), 1.41 (s, 9H); $^{13}$C NMR (300 MHz, CDCl$_3$) δ 169.2, 160.6, 155.7, 151.7, 138.9, 136.3, 136.2, 129.6, 128.5, 128.3, 128.1, 128.1, 127.6, 127.5, 127.21, 126.4, 85.9, 81.7, 57.0, 46.1, 34.6, 27.5. IR (thin film) 2983, 1734, 1628, 1282, 1234, 1151, 1120, 1016, 696 cm$^{-1}$; HRMS (LC-ESI) m/z calcd for C$_{30}$H$_{32}$N$_3$O$_3$ [MH]$^+$ 482.2438. Found 482.2427.

44

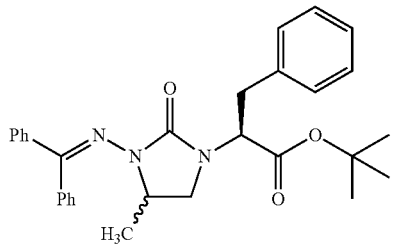

45

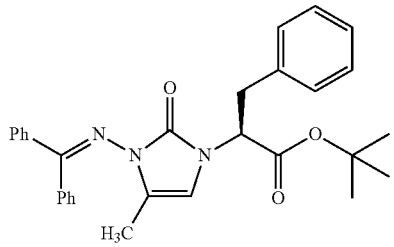

(5SR,2'S)-1-((Diphenylmethylidene)amino)-3-(tert-butyl-3'-phenyl-2'-propanoate)-5-methyl-imidazolidin-2-one (44) and (2'S)-1-((Diphenylmethylene)amino)-3-(tert-butyl-3'-phenyl-2'-propanoate)-4-methyl-imidazolin-2-one (45)

In a hydrogenation vessel, 5-methylidene-imidazolidin-2-one 43 (600 g, 1.25 mmol, 1 eq) was dissolved in EtOH (40 mL), and treated with palladium-on-carbon (10 wt %, 168 mg, 0.12 mmol, 0.1 eq). The vessel was evacuated and filled with hydrogen atmosphere three times and the filled to 50 psi of H$_2$, under which atmosphere the solution was stirred for 45 min. The catalyst was removed by filtration on a pad of Celite™, which was washed with EtOAc[2] The filtrate and washings were combined and the volatiles were evaporated to a residue, which was purified by flash chromatography using 20% EtOAc in hexane as eluent. First to elute was a 3:2 diastereomeric mixture of 5-methyl-imidazolidin 2-ones 54 (324 mg, 54%): R$_f$=0.54 (4:1 hexane/EtOAc). The proton NMR signals for the mixture follow with those distinct signals for the minor isomer in brackets. $^1$H NMR (400 MHz, CDCl$_3$) δ 7.62-7.05 (m, 15H), [4.78 (m, 1H)], 4.66 (m, 1H), 4.58 (m, 1H), [4.53 m, 1H], [3.78 (m, 1H)], 3.56 (m, 1H), 3.34 (m, 1H), 3.17-3.11 (m, 1H), 2.98-2.91 (m, 1H), [1.48 (d, 3H)], 1.41-1.36 (overlapping s and d, 12H). The carbon NMR signals for the mixture follow with those distinct signals for the minor isomer in parentheses. $^{13}$C NMR (300 MHz, CDCl$_3$) δ 170.2, 159.7, 158.4, 139.9, 137.2, (137.0), 130.2, (130.1), 129.1, (129.0), 128.8, 128.6, (128.6), 128.5, (128.4), 128.0, 127.8, (127.6), 127.5, 126.8, (126.7), 81.9, (81.8), 75.0, (74.9), 57.7, 57.2, 50.6, 50.3, 35.3, (35.1), 28.1, (28.0), 20.0, (19.9). IR (thin film) 2979, 1733, 1625, 1055, 1035, 1014, 695 cm$^{-1}$; HRMS (LC-ESI) m/z calcd for C$_{30}$H$_{34}$N$_3$O$_3$ [MH]$^+$ 484.2595. Found 484.2589. Second to elute was 5-methyl-N-amino-imidazolin-2-one 45, from double bond migration to the endo isomer: 156 mg, 26% as yellow oil; R$_f$=0.5 (4:1 hexane/EtOAc); $^1$H NMR (400 MHz, CDCl$_3$) δ 7.65 (m, 2H), 7.42-7.25 (m, 11H), 7.07 (m, 2H), 6.35 (s, 1H), 4.74 (t, J=8.0 Hz, 1H), 3.09 (m, 2H), 2.18 (s, 3H), 1.35 (s, 9H); $^{13}$C NMR (300 MHz, CDCl$_3$) δ 169.0, 158.2, 156.9, 139.9, 139.0, 136.8, 136.2, 132.5, 130.3, 129.3, 128.5, 128.3, 128.0, 127.7, 127.5, 127.0, 109.7, 82.6, 57.7, 37.2, 27.9, 11.6. IR (thin film) 2981, 1736, 1689, 1618, 1582, 1542, 1371, 1148, 1050, 1035, 1026, 696 cm$^{-1}$; HRMS (LC-ESI) m/z calcd for C$_{30}$H$_{32}$N$_3$O$_3$ [MH]$^+$ 482.2438. Found 482.2432.

Although simple imidazolin-2-one and imidazolidin-2-one heterocycles have respectively been prepared by base-promoted 5-exo-dig cyclizations of propargylic and allylic ureas,[xiv] annulation typically necessitates activation of the π-system using transition metal salts (i.e. silver,[xv] palladium,[xvi] and gold complexes)[xvii] as well as toluenesulfonyl protection of the nucleophilic urea-nitrogen. For example, cyclic amino acids, such as dehydroprolines had been prepared respectively by palladium- and silver-catalyzed 5-endo dig cyclization of NTs- and Boc-protected propargylglycine analogs.[xviii,xix] Although these precedents were encouraging, the influences of the hydrazine and chiral alkyl substituted residues on the cyclization of the urea nitrogen of aza-propargylglycine analogs proved to be challenges in the construction of N-aminoimidazolin-2-one peptide mimics (Table 4).

As a model for exploring cyclization conditions, azapropargylglycine dipeptide 1 was prepared by a route featuring chemoselective alkylation of benzhydrylidene aza-glycinyl-D-phenylalanine tert-butyl ester 7 with propargyl bromide.[xx] In the alkylation, the number of equivalents of potassium tert-butoxide was limited to circumvent racemization. Specifically, when using high quality potassium tert-butoxide (99.2% purity), it was found that a 1.1 excess led to 32% racemisation, whereas the use of 0.95 equivalent of base led to significantly less racemization (12%). Initial attempts to effect the 5-exo-dig cyclization of azadipeptide 1 using homogeoneous gold catalysis [(t-Bu)2(obiphenyl) PAuCl (5 mol %) and AgOTf (5 mol %)] failed, likely because the urea nitrogen was insufficiently nucleophilic. N-Amino-imidazolin-2-one 2 was however obtained in 81% yield, by adding 2.5 equivalents of NaH to the mixture containing 1 and the cationic gold complex formed in situ in acetonitrile for 2 h (Table 4, entry 3). The impact of gold catalysis was however deemed negligible, because 2 was produced in 73% yield on reaction of 1 with 2.5 equivalents of NaH in acetonitrile without catalyst (Table 4, entry 1). In the 5-exo-dig cyclization, an exocyclic double bond is first produced and migration of the double bond inside the ring furnished the thermodynamically more stable N-amino-imidazolin-2-one 3. Acetonitrile proved essential as solvent, and excess base led to higher reaction yields.

TABLE 4

Synthesis of N-amino imidazolin-2-one building block 4.

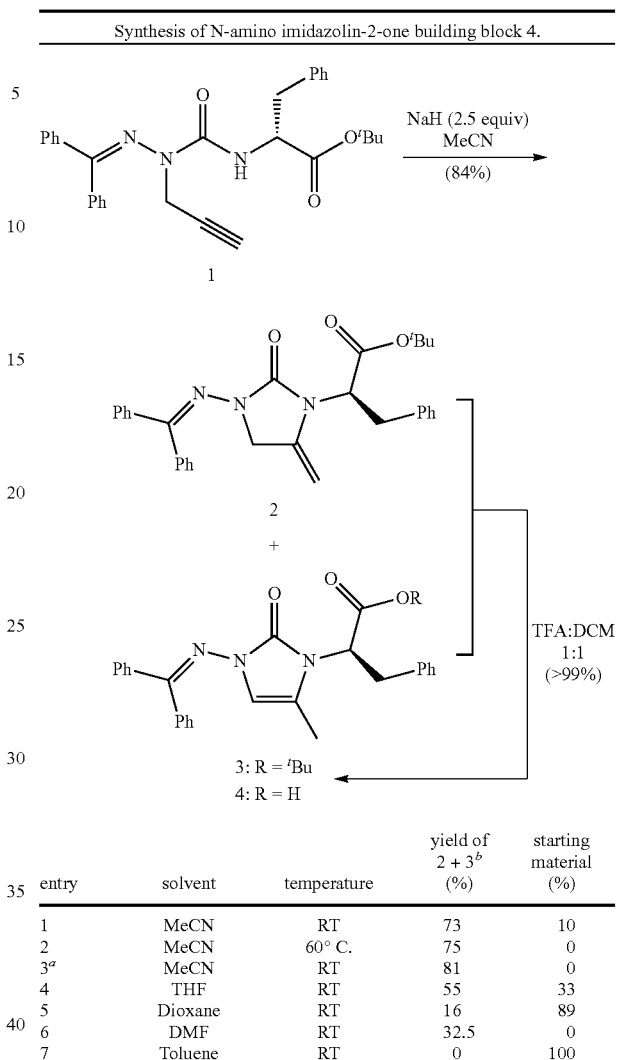

| entry | solvent | temperature | yield of 2 + 3$^b$ (%) | starting material (%) |
|---|---|---|---|---|
| 1 | MeCN | RT | 73 | 10 |
| 2 | MeCN | 60° C. | 75 | 0 |
| 3$^a$ | MeCN | RT | 81 | 0 |
| 4 | THF | RT | 55 | 33 |
| 5 | Dioxane | RT | 16 | 89 |
| 6 | DMF | RT | 32.5 | 0 |
| 7 | Toluene | RT | 0 | 100 |

$^a$Reaction performed with (t-Bu)$_2$(o-biphenyl)PAuCl (5 mol %) and AgOTf (5 mol %).
$^b$NMR Yield using 1,3,4 trimethoxybenzene as internal standard.

With these cyclization conditions in hand, N-acyl amino imidazolin-2-one amide 14 was synthesized to study the conformation of this model system in the solid state and in solution, using X-ray crystallography and NMR spectroscopy, respectively (Scheme 2). Benzhydrylidene aza-glycinyl-D-phenylalanine isopropyl amide 9 was prepared from benzhydrylidene aza-glycinyl-D-phenylalanine tert-butyl ester 7 by tertbutyl ester cleavage in a 1:1 v/v mixture of TFA: DCM, followed by coupling to iso-propylamine using a mixed anhydride approach.[xx] Employment of amide 9 in the alkylation and cyclization steps minimized racemization, likely due to preferential amide nitrogen deprotonation inhibiting removal of the α-hydrogen. Indeed, in comparison to the alkylation of aza-glycinyl-D-phenylalanine tert-butyl ester 7, the chemoselective alkylation of semicarbazone 9 gave aza-propargyl glycinamide 10 in 71% yield with no detectable racemization (see above). Subsequent NaH-promoted 5-exo-dig cyclization gave imidazolin-2-one 11, possessing an exocyclic double bond, in a 57% yield. However, olefin migration occurred upon hydrazone removal, using hydroxylamine hydrochloride in pyridine 11 to afford N-amino imidazalone 12, which without further purification was treated with 4-methoxybenzoyl chloride to provide N-acyl dipeptide amide 14 in 56% yield.

Scheme 2. Synthesis of N-acyl amino imidazolin-2-one isopropyl amide 14.

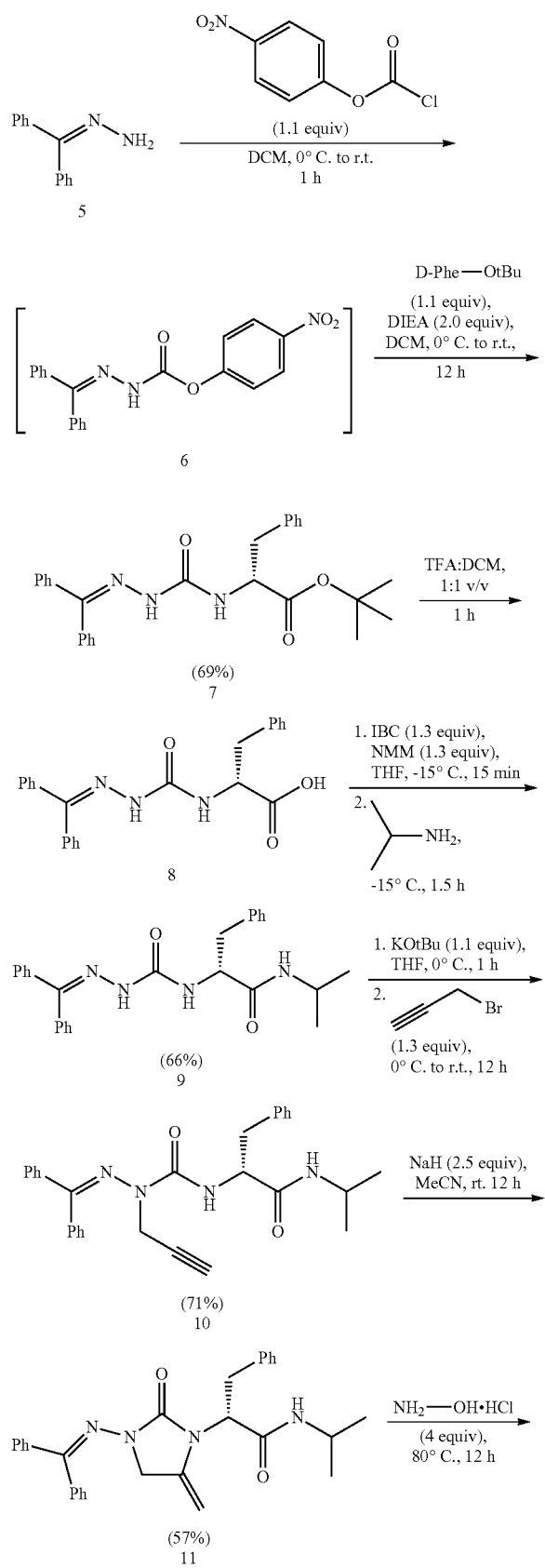

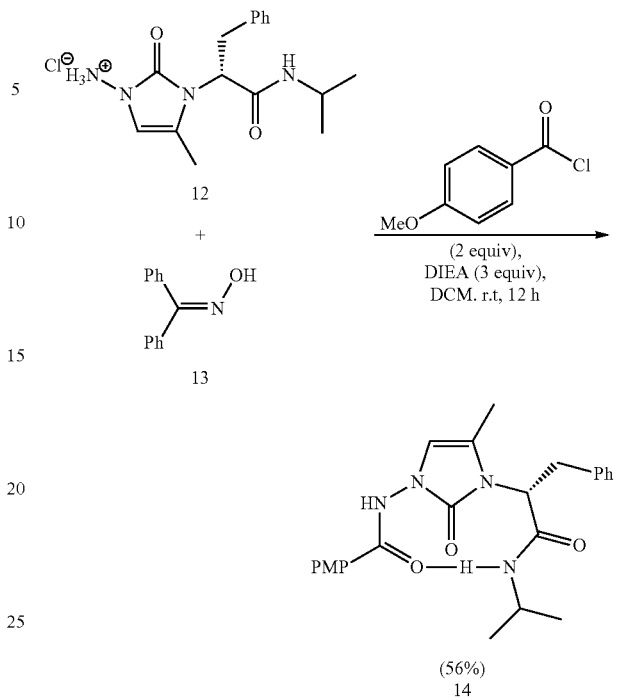

Crystals of 14 were grown by slow diffusion of hexanes into an ethyl acetate/chloroform mixture. X-ray diffraction revealed two preferred turn conformations in the solid state (FIG. 1). One structure, 14a exhibited φ and ψ dihedral angles characteristic of a type II' β-turn (Table 5), with an intramolecular ten-member hydrogen bond between residues i and i+3 and a distance of 3.01 Å. The second structure, 14b deviated from that of 14a primarily by rotation of the ψ2 dihedral angle, which positioned the isopropylamide in an orientation to favor dihedral angle geometry and a seven-membered hydrogen bond characteristic of an inverse γ turn (Table 5). The x-ray data for 14 has been compared with ideal turn geometry as well as crystal structures of azapeptide and α-amino-γ-lactams, which also adopt turn conformations (Table 5).[xxi,xxii,xxiii]

TABLE 5

Ideal φ and ψ dihedral angles (in degrees) for β-I, β-II', and γ-turns compared with those from crystal structures of 14-17.

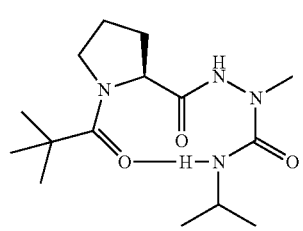

TABLE 5-continued

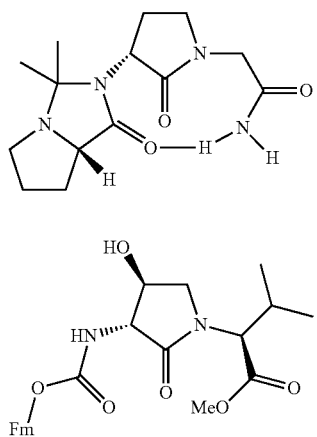

| Type of turn | $\phi_{i+1}$ | $\psi_{i+1}$ | $\phi_{i+2}$ | $\psi_{i+2}$ |
|---|---|---|---|---|
| β-II | −60 | 120 | 80 | 0 |
| β-II' | 60 | −120 | −80 | 0 |
| γ | n/a | n/a | 70 | −60 |
| Inverse γ | n/a | n/a | −70 | 60 |
| 14a | 58.9 | −153.3 | −69.1 | −4.6 |
| 14b | 62.1 | −166.1 | −71.7 | 65.7 |
| 15 | −55.4 | 120.9 | 89.3 | 17.8 |
| 16 | −42 | 133 | 89 | −6.9 |
| 17 | −40 | 116 | 96 | −97 |

Figure 2A:
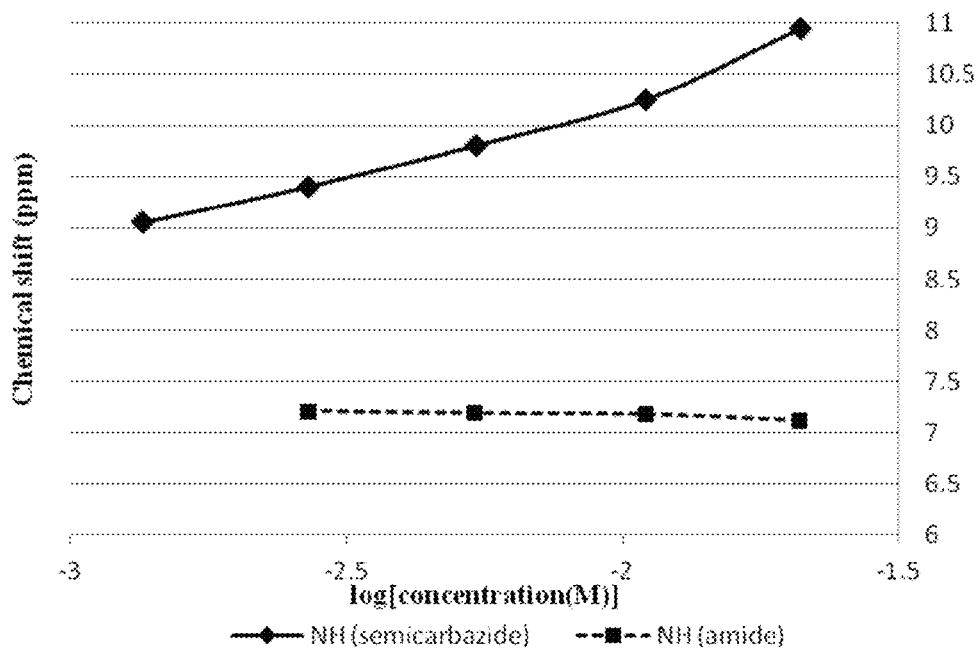
FIG. 2A shows NMR chemical shift of the amide and semicarbazide protons of compound 14 in CDCl3 at room temperature, as a function of the logarithm of concentration.
Figure 2B:
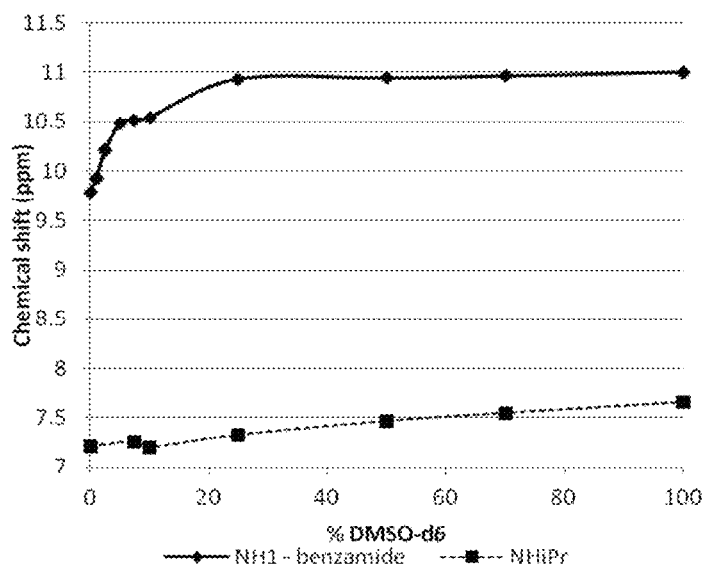
FIG. 2B shows NMR chemical shift (ppb) of the amide and semicarbazide protons of compound 14 in CDCl3 as a function of increasing DMSO-$d_6$ concentration.

In contrast to amino lactams, the planar geometry of the N-amino-imidazalone causes the ψ1 dihedral angle to deviate by 33-46° from that of an ideal type II' β-turn (120°). In azapeptides, the α-nitrogen may adopt planar or pyramidal geometry depending on sequence, with preferences for type I, II, and VIa β-turns, in which the aza residue often neighbors a turn-inducing proline residue. Similarly, the N-amino imidazolinone residue may assume type II or II' geometry contingent on the stereochemistry of the C-terminal residue. In contrast, α-amino-γ-lactam-containing peptides (i.e., 16 and 17) adopt type II or II' β-turns contingent on the α-carbon stereochemistry of both the amino lactam and the C-terminal residue.[xxiii] The conformation of N-amino imidazolin-2-one 14 was next studied in solution using NMR spectroscopy (FIGS. 2A and B). Initially, variations in the amide proton chemical shifts of 14 were monitored as a function of concentration in CDCl$_3$ between 1 mM and 20 mM, which indicated the invariability of the isopropylamide NH signal, suggesting that no aggregation occurred at the studied concentrations (FIG. 2A). By measuring the amide chemical shift values as a function of DMSO-d$_6$% in CDCl$_3$, the isopropylamide NH signal demonstrated very little variation (0.45 ppm) going from 1 to 100% DMSO-d$_6$, whereas the benzamide chemical shift varied by 1.21 ppm (FIG. 2B). These results are consistent with solvent-shielded (hydrogen-bonded) and solvent-exposed hydrogens,[xxiv] as well as with the X-ray crystal structures of 14.

In order to prepare N-amino indolizidinones possessing side-chains, attention was turned towards the modification of the aza-propargylglycine residue, with the inherent goal to access constrained Phe, Tyr, Trp and His peptidomimetics. Sonogashira couplings were performed on dipeptide 1, using the appropriate aryl iodides, Pd(PPh$_3$)$_2$Cl$_2$, and CuI in a 1:1 DMF:Et$_2$NH mixture (Table 6). Electron rich and electron poor aryl iodides as well as N-protected indole and imidazole iodides, all reacted in the coupling reaction to furnish the desired products in 50-90% yields.

TABLE 6

Sonogashira coupling of aryliodides and azapropargylglycine dipeptide 1.

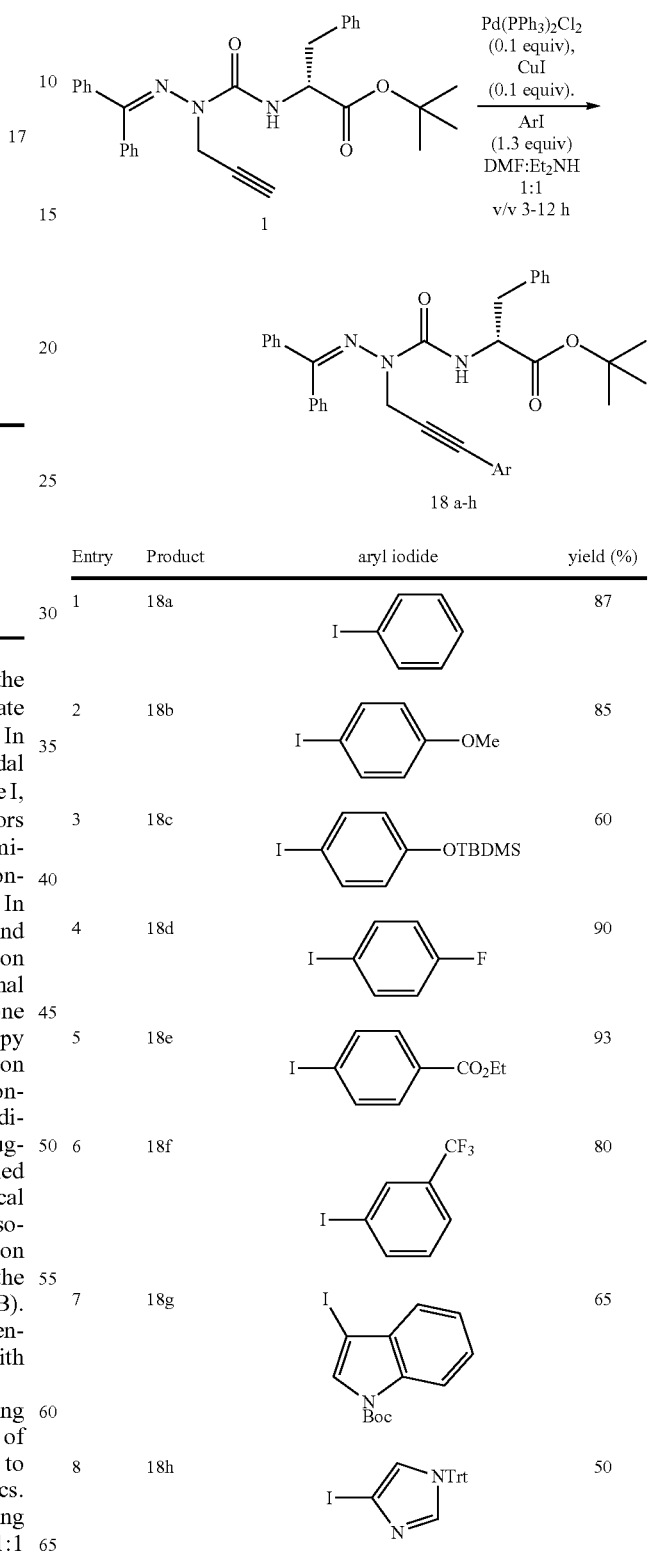

Alternatively, under the same reaction conditions, 4-iodonitrobenzene failed to give the desired Sonogashira adduct; instead, ketone 20 was obtained in 87% yield after purification by silica gel chromatography (Scheme 3). In the Sonogashira reaction, the electrophilic 4-nitrophenylsubstituted alkyne may have underwent an oxapalladation reaction to afford intermediate 19, which may be hydrolyzed to ultimately give ketone 20. Consequently, alkyne 22 was prepared from aza-glycinyl-D-phenylalanine tert-butyl ester 7 by alkylation with 1-(3-bromoprop-1-ynyl)-4-nitrobenzene using potassium tert-butoxide.[11]

Scheme 3. (a) Synthesis of ketone 20 using Sonagashira coupling conditions. (b) Synthesis of alkyne 22 via the alkylation route.

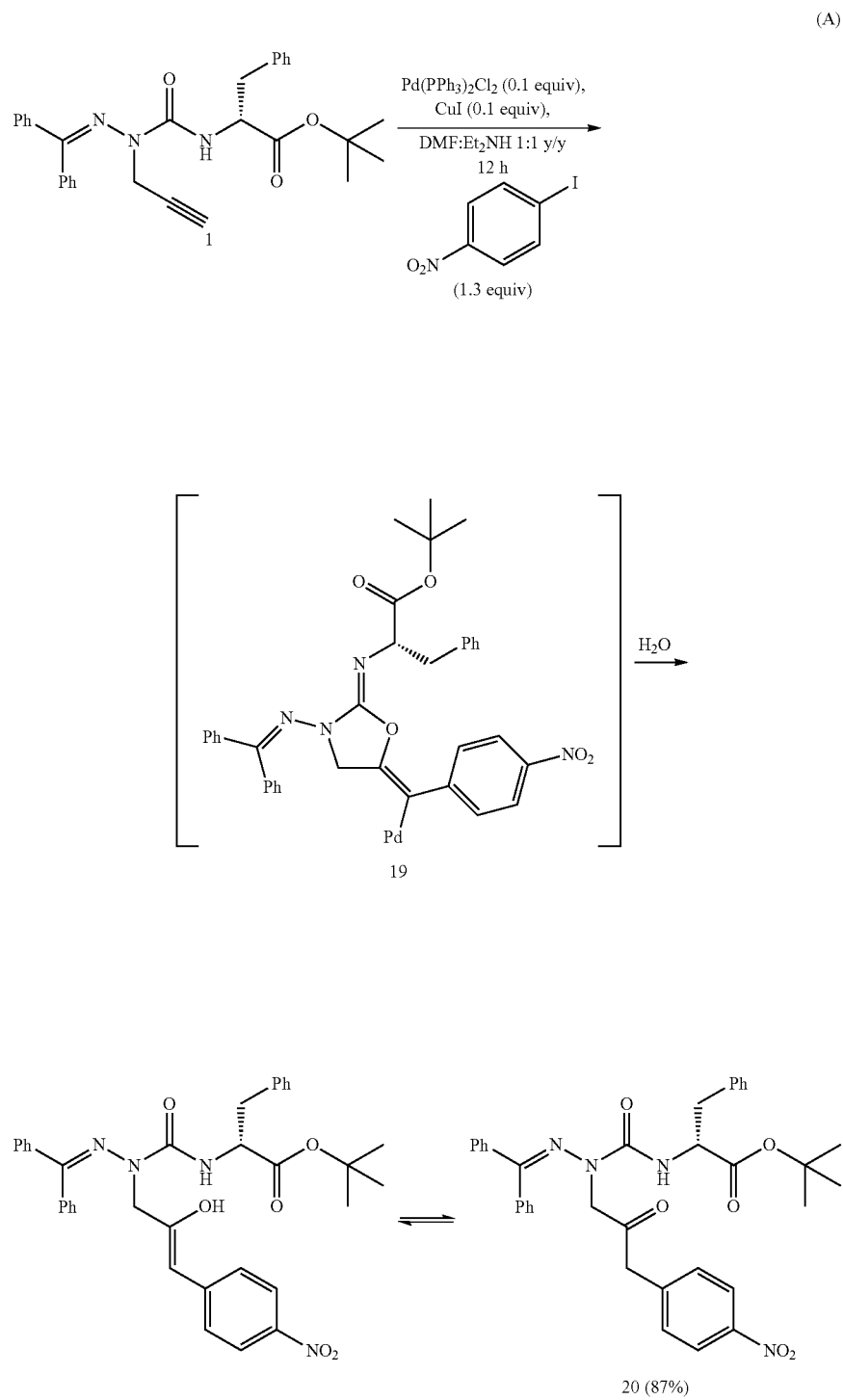

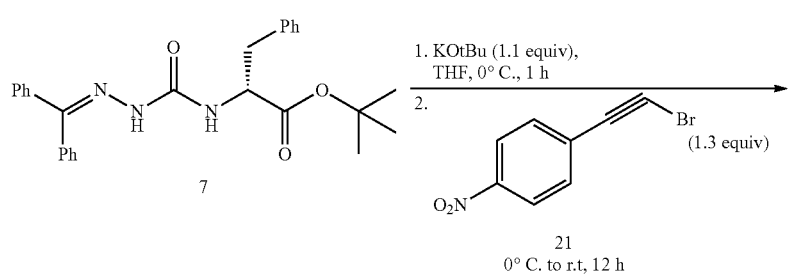

(B)

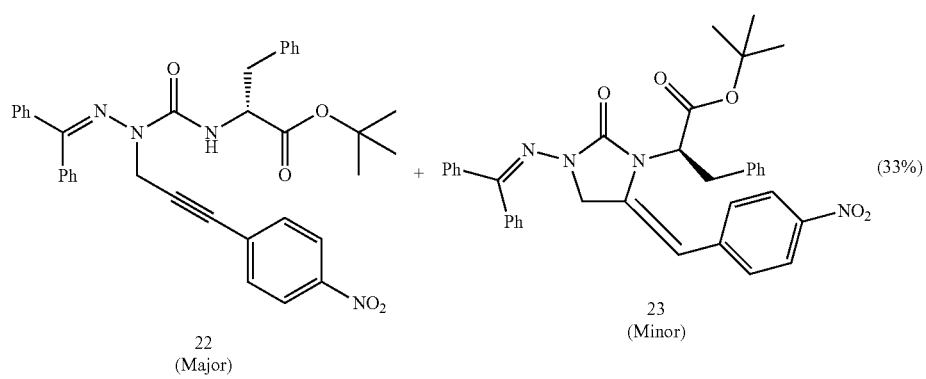

With nine aza-propargylglycines 18 in hand, the synthesis of substituted N-amino-imidazolin-2-ones was pursued employing our base-promoted 5-exo-dig cyclization strategy. Products possessing endocyclic and exocyclic double bonds were obtained from the cyclization of aryl-substituted alkynes 18. For example, imidazolin-2-ones 24a and 25a were isolated as isomeric mixtures in 69% yield. Although cis and trans geometry were possible, a two-dimensional NOESY experiment revealed only the exocyclic cis double bond geometry through coupling between the vinyl proton and the CH$_2$ of the imidazolidinone, and absence of coupling between the vinyl proton and the Cα. Finally, the acidic conditions for cleavage of the tert-butyl ester promoted double bond migration inside the five membered ring to furnish 26a (Table 7), albeit partial racemization (26%)[xxv] of the phenylalanine tert-butyl ester was observed, likely due to the alkaline cyclization conditions. Attempts at a one-pot amino-palladation/cross-coupling reaction sequence failed to synthesize N-amino imidazolin-2-one 24a using Pd(PPh$_3$)$_4$, iodobenzene, and a variety of bases; instead, Sonogashira adduct 18a was isolated.

Employing the various aryl substituted acetylenes in the cyclization chemistry, a fluorine p-substituent was found to be well tolerated and gave the desired product in a similar yield (64%, Table 4, entry 4). Substrates with electron withdrawing substituents (i.e., trifluoromethyl and nitro) reacted rapidly giving complete consumption of starting material, albeit with lower yields due to decomposition. In the case of the nitro substituent, partial cyclization was observed under the alkylation conditions (Scheme 3b). On the other hand, electron rich substituents exhibited poor reactivity. For example, aza-p-methoxyphenylpropargylglycine 18b afforded the desired N-amino imidazolin-2-one in only 10% yield with recovery of starting material (Table 7, entry 2). Silyloxyphenyl alkyne 18c underwent a base-promoted deprotection of the silyl group, without cyclization, and imidazolyl alkyne 18i failed to react under the reaction conditions returning starting material exclusively. In contrast, N-Boc-3-indolyl alkyne 18g underwent base-promoted cyclization to afford constrained tryptophan mimic imidazolin-2-one 24 g in 40% yield with recovery of starting material.

TABLE 7
Synthesis of substituted N-amino imidazolin-2-one building blocks.
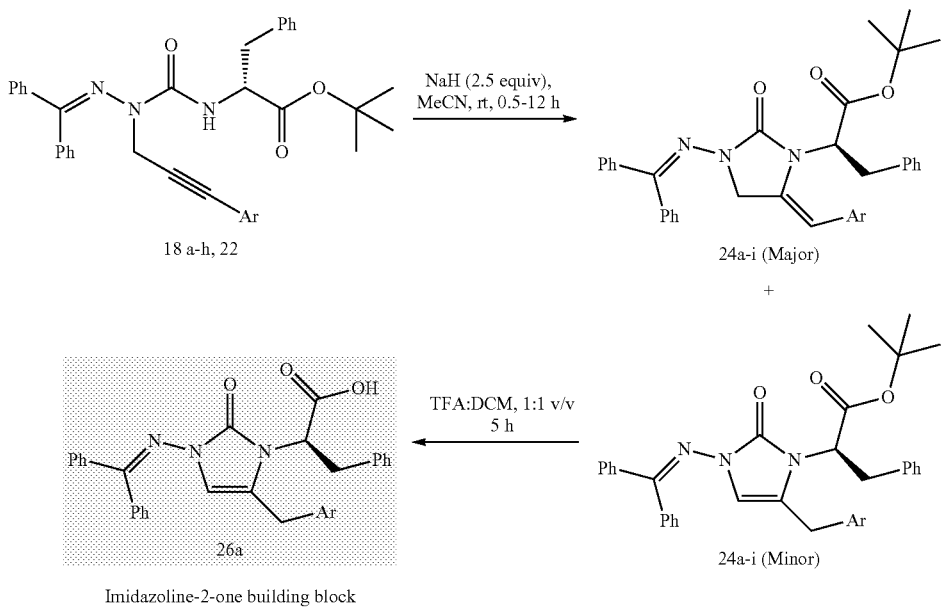
| Entry | Product | aryl | yield of 24 + 25 (%) |
|---|---|---|---|
| 1 | 24a + 25a | phenyl | 69 |
| 2 | 24b + 25b | 4-OMe-phenyl | 10 |
| 3 | 24c + 25c | 4-OTBDMS-phenyl | 0[a] |
| 4 | 24d + 25d | 4-F-phenyl | 64 |
| 5 | 24e + 25e | 4-CO$_2$Et-phenyl | 42 |
| 6 | 24f + 25f | 3-CF$_3$-phenyl | 34 |
| 7 | 24g + 25g | 3-(N-Boc-indolyl) | 40 |

TABLE 7-continued

Synthesis of substituted N-amino imidazolin-2-one building blocks.

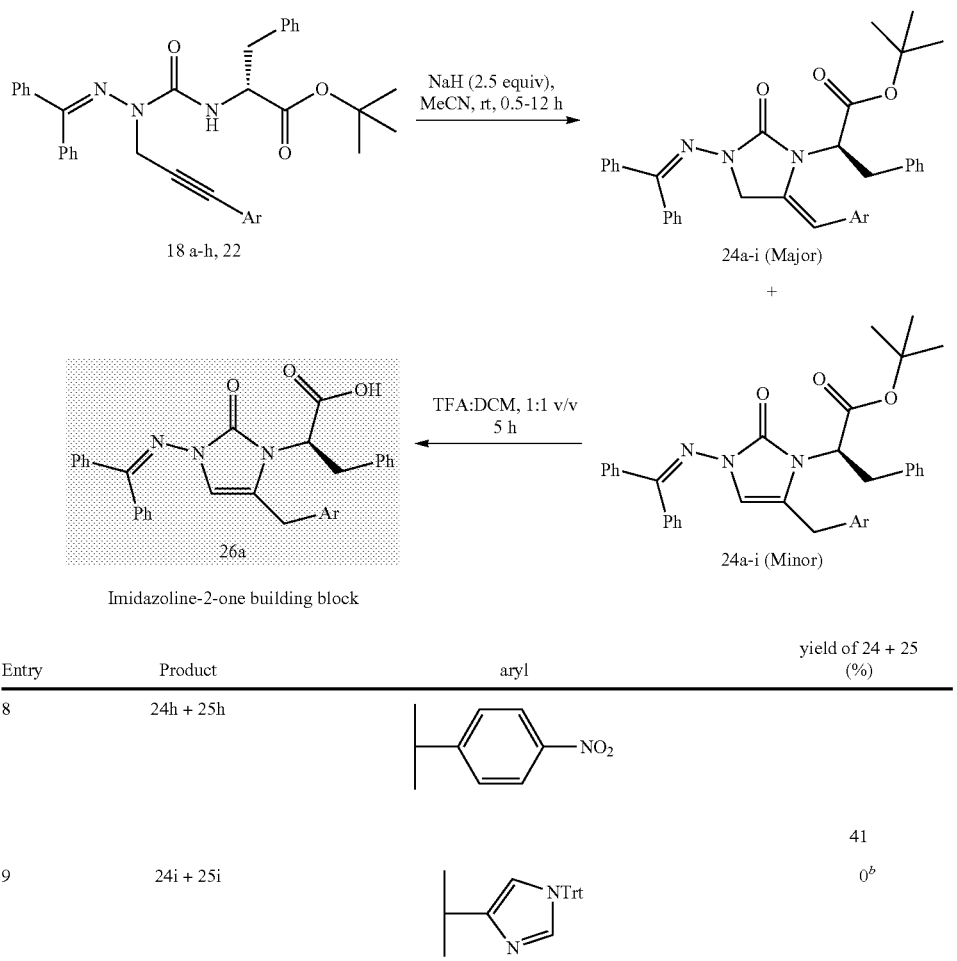

| Entry | Product | aryl | yield of 24 + 25 (%) |
|---|---|---|---|
| 8 | 24h + 25h | —C₆H₄—NO₂ | 41 |
| 9 | 24i + 25i | imidazole-NTrt | 0[b] |

[a]The only product observed resulted from deprotection of the TBDMS.
[b]Starting material was recovered.

The influences of the N-amino imidazolin-2-one mimics on peptide conformation and biology were examined by replacing the Trp[4]-D-Phe[5] residues of GHRP-6 with imidazolin-2-one dipeptide building blocks 4 and 26a. The synthetic hexapeptide, GHRP-6 has been shown to exhibit affinity for two distinct receptors: the Growth Hormone Secretagogue Receptor 1a (GHS-R1a)[xxvi] and the Cluster of Differentiation 36 (CD36) scavenger receptor.[xxvii] Towards the development of GHRP-6 analogs with improved stability and receptor selectivity for the CD36 receptor as potential treatments of age-related macular degeneration, [azaPhe[4]] GHRP-6 was previously demonstrated to exhibit preferential CD36 receptor selectivity attributed to a β-turn conformation about the aza-residue, as demonstrated by CD spectroscopy in water.[xi] In contrast, α- and β-amino-γ-lactam (Agl and Bgl) scans of the GHRP-6 peptide sequence produced [(S)-Agl[4]]- and [(S)-Bgl[4]]GHRP-6 analogs with decreased affinity for both the GHS-R1a and CD36 receptors (Jamieson, A. G.; Boutard, N.; Beauregard, K.; Bodas, M. S.; Ong, H.; Quiniou, C.; Chemtob, S.; Lubell, W. D. Positional Scanning for Peptide Secondary Structure by Systematic Solid-Phase Synthesis of Amino Lactam Peptides. *J. Am. Chem. Soc.* 2009, 131, 7917-7927. Boutard, N.; Jamieson, A. G.; Ong, H.; Lubell, W. D. Structure-activity analysis of the growth hormone secretagogue GHRP-6 by alpha- and beta-amino gamma-lactam positional scanning. *Chem. Biol. Drug. Des.* 2010, 75, 40-50). Loss of side-chain functionality from insertion of the Agl and Bgl residues may be responsible for the observed drop in binding affinity. Similarly, the benzyl side chain in [azaPhe[4]]GHRP-6 was involved in maintaining high affinity for the CD36 receptor.[xxia,b] N-Amino imidazolin-2-ones 4 and 26a were thus employed to furnish GHRP-6 analogs with restricted backbone and side chain geometry to achieve affinity for the CD36 receptor (Scheme 4).

Scheme 4. Solid-phase incorporation of N-amino imidazolin-2-ones 4 and 26a at the Trp$^4$-D-Phe$^5$ position of GHRP-6.
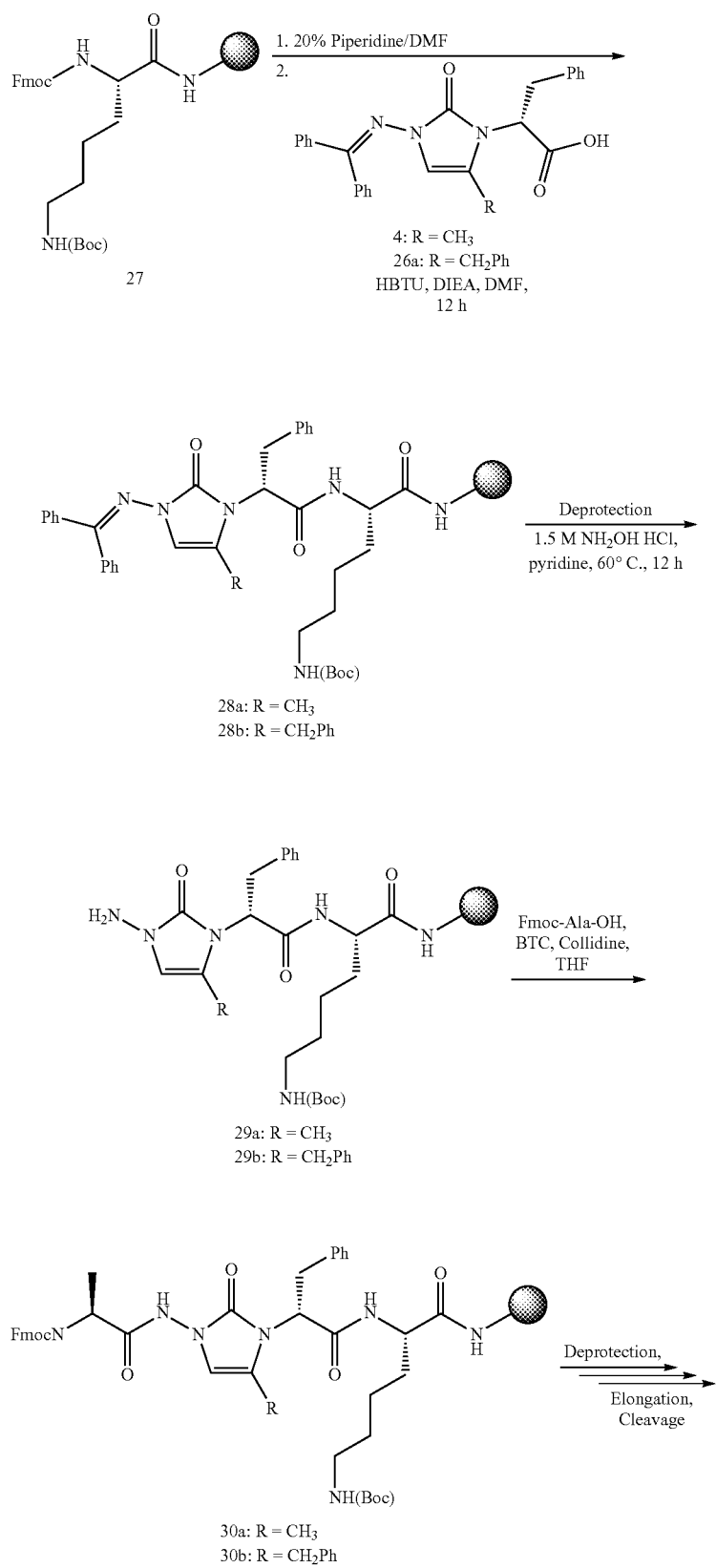

-continued

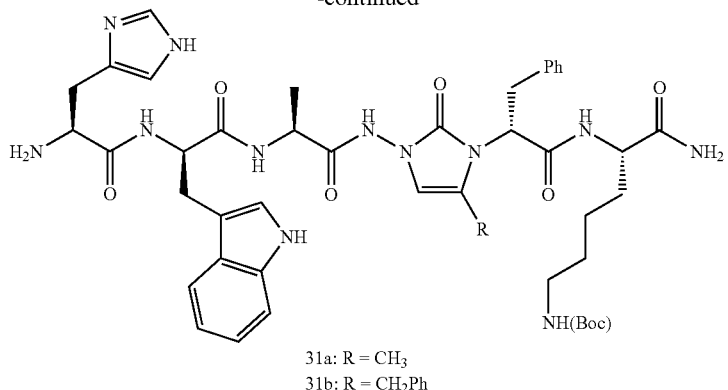

31a: R = CH₃
31b: R = CH₂Ph

● = Rink amide resin

Hydrazone-protected N-amino imidazolin-2-ones 4 and 26a were respectively coupled to ε-(Boc)lysine linked to Rink amide resin using standard conditions (HBTU, DIEA). The hydrazone was removed using NH₂OH.HCl in pyridine,[11] and the resulting semicarbazides were acylated with Fmoc-Ala activated using triphosgene to give the corresponding tetrapeptide resins 30a and 30b. Fmoc deprotection, peptide elongation and cleavage from the resin afforded N-amino imidazolin-2-one-containing GHRP-6 analogs 31a and 31b with 71% and 68% crude purities, respectively. Material of >99% purity was subsequently isolated using reverse-phase HPLC to afford peptides 31a and 31b in 10% and 5% overall yields, respectively (Table 8).

dazolin-2-one⁴]GHRP-6 31b exhibited similar negative and positive maxima with lower ellipticity. The nature of the side chain on the imidazolinone and stereochemistry of the preceding residue may thus affect the overall peptide conformation.

N-Amino-imidazolinone peptide mimics 31a and 31b were subsequently tested for binding affinity towards the CD36 receptor using a surface plasmon resonance (SPR) spectroscopy assay,[xxviii] as well as for inhibitory activity on MAP kinase JNK phosphorylation induced by the mildly oxidized low-density lipoprotein (oxLDL)-derived phospholipid, 1-palmitoyl-2(5-oxovaleroyl)-sn-glycero-3-phosphocholine (POVPC) in a cellular assay using RAW 264.7

TABLE 8

Yields and purities of GHRP-6 analogs 31a and 31b.

| peptide | crude purity[a] (%) | purity[b] (%) MeOH | purity[b] (%) MeCN | yield[c] (%) | HRMS [H + 1]⁺ or [H + 2]⁺² ions m/z (calcd) | HRMS [H + 1]⁺ or [H + 2]⁺² ions m/z (obsd) |
|---|---|---|---|---|---|---|
| 31a His-D-Trp-Ala-(4-Me-imidazolin-2-one)-D-Phe-Lys-NH₂ | 71 | >99 | >99 | 10 | 392.20609 | 392.20752 |
| 31b His-D-Trp-Ala-(4-Bu-imidazolin-2-one)-D-Phe-Lys-NH₂ | 68 | >99 | >99 | 5 | 859.4362 | 859.43642 |

[a]RP-HPLC purity at 214 nm of the crude peptide in MeOH/H₂O containing 0.1% formic acid.
[b]RP-HPLC purity at 214 nm of the purified peptide in MeOH/H₂O and MeCN/H₂O containing 0.1% formic acid.
[c]Yields after purification by RP-HPLC are based on resin loading.

Figure 3A:
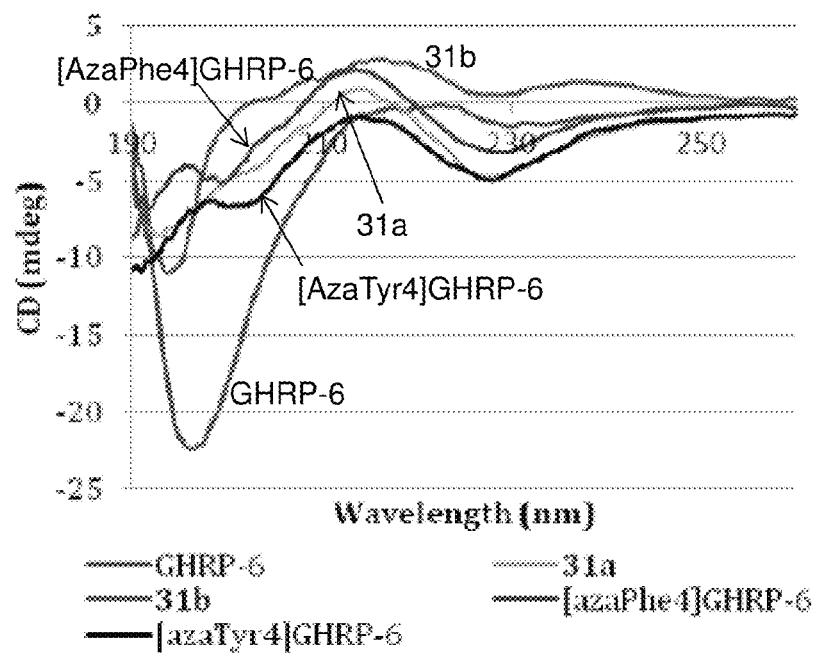
FIG. 3A shows the circular dichroism spectra of RS-31a and 31b compared with GHRP-6, [azaTyr4]GHRP-6 and [azaPhe4]GHRP-6.
Figure 3B:
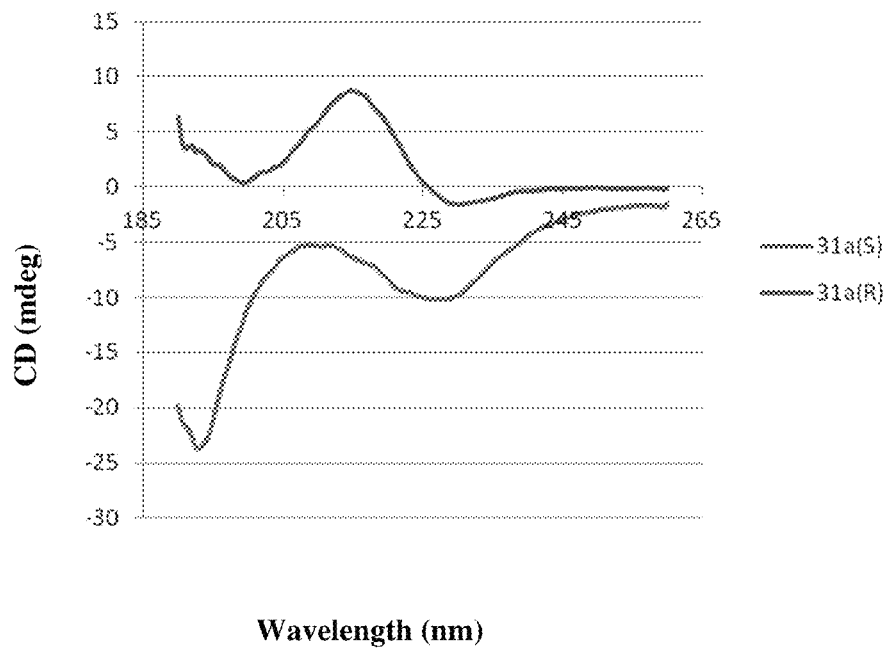

Circular dichroism spectroscopy was used to assess the effect of the N-amino imidazolin-2-one moieties on peptide conformation in water (FIG. 3A). The CD signature of GHRP-6 was characteristic of a random coil, exhibiting a negative maximum around 190 nm. Introduction of N-amino-imidazolin-2-ones residues at the Trp4 position of the GHRP-6 peptide gave analogs with CD spectra indicative of turn conformation contingent on the side-chain functionality. Specifically, peptide mimic RS-31a, which possesses a methyl substituent at the 4-position of the imidazolin-2-one ring, exhibited an apparent curve shape indicative of a turn conformation similar to that of [azaPhe⁴]GHRP-6 and [azaTyr⁴]GHRP-6, with distinctive negative maxima at 230 and 190 nm and a positive maximum at 215 nm. The curve shape of RS-31a is due to a composite of the curves shapes for the CD spectra of S- and R-31a (FIG. 3B) which may be respectively characterized as type II polyproline helix and turn conformations. The CD curve of [N-amino 4-benzylimimurine macrophage cells (Table 9). In these studies, [azaTyr⁴]GHRP-6, a GHRP-6 azapeptide derivative which was previously shown to bind to the CD36 receptor using SPR spectroscopy, was used as a positive control.[xxviii] In the binding and cellular assays, [N-amino-4-methyl-imidazolin-2-one⁴]GHRP-6 RS-31a exhibited respectively similar affinity for the CD36 receptor and increased inhibitory activity on MAP kinase JNK phosphorylation relative to [azaTyr⁴] GHRP-6. On the other hand, [N-amino-4-benzyl-imidazolin-2-one⁴]GHRP-6 31b exhibited comparable affinity to that of [azaTyr⁴]GHRP-6; yet, relatively lower inhibitory activity in the kinase assay. The observed conformational differences exhibited in their circular dichroism spectra correlated with the CD36 binding affinity ascertained by the SPR assay and inhibitory activity in the JNK kinase assay. Interestingly, contrary to the decreased affinity induced by the [(S)-Agl⁴]- and [(S)-Bgl⁴]GHRP-6 analogs, the restriction of the backbone conformation caused by the imidazolin-2-one moiety appears to favor binding to the CD36 receptor, in spite of the loss of the aromatic side-chain.

TABLE 9

Binding values for GHRP-6 analogs RS-31a and 31b.

| peptide squence | SPR | | JNK-kinase cellular assay |
| --- | --- | --- | --- |
| | $K_d$ (M) | $\Delta\lambda_{SPR}$ (nm) | $EC_{50}$ (M) |
| [azaTyr⁴]GHRP-6 His-D-Trp-Ala-AzaTyr-D-Phe-Lys-NH₂ | $5.0 \times 10^{-6}$ | 1.8 | $2.14 \times 10^{-7}$ |
| 31a His-D-Trp-Ala-(4-Me-imidazolin-2-one)-D-Phe-Lys-NH₂ | $4.9 \times 10^{-6}$ | 1.1 | $5.54 \times 10^{-8}$ |
| 31b His-D-Trp-Ala-(4-Bu-imidazolin-2-one)-D-Phe-Lys-NH₂ | $1.1 \times 10^{-5}$ | 1.6 | $\gg 1 \times 10^{-5}$ |

Pursuing a better understanding of the importance of conformation at the 3-position, as well as positive charge at the 1- and 3-positions, a set of [4-methyl-aminoimidazol-2-one⁴] GHRP-6 analogs were prepared by elongating resin-bound tripeptide 29a using Fmoc-D- and L-Pro, as well as Fmoc-D- and L-Lys(Boc) to acylate the aminoimidazolone moiety and either Fmoc-Ala or Fmoc-His(Tr) at the terminal residue of the peptide sequence: [His¹, Lys³, N-Amino-4-methylimidazol-2-one⁴]GHRP-6 (His-D-Trp-Lys-(N-amino-4-methyl-imidazol-2-one)-D-Phe-Lys-NH₂, 422A), [Ala¹, Lys³, N-Amino-4-methylimidazol-2-one⁴]GHRP-6 (Ala-D-Trp-Lys-(N-amino-4-methyl-imidazol-2-one)-D-Phe-Lys-NH₂, 422B), [His¹, D-Lys³, N-Amino-4-methylimidazol-2-one⁴] GHRP-6 (His-D-Trp-D-Lys-(N-amino-4-methyl-imidazol-2-one)-D-Phe-Lys-NH₂, 423A), [Ala¹, D-Lys³, N-Amino-4-methylimidazol-2-one⁴]GHRP-6 (Ala-D-Trp-D-Lys-(N-amino-4-methylimidazol-2-one)-D-Phe-Lys-NH₂, 423B), [His¹, Pro³, N-Amino-4-methylimidazol-2-one⁴]GHRP-6 (His-D-Trp-Pro-(N-amino-4-methyl-imidazol-2-one)-D-Phe-Lys-NH₂, 424A), [Ala¹, Pro³, N-Amino-4-methylimidazol-2-one⁴]GHRP-6 (Ala-D-Trp-Pro-(N-amino-4-methyl-imidazol-2-one)-D-Phe-Lys-NH₂, 424B), [His¹, D-Pro³, N-Amino-4-methylimidazol-2-one⁴]GHRP-6 (His-D-Trp-Pro-(N-amino-4-methyl-imidazol-2-one)-D-Phe-Lys-NH₂, 425A), and [Ala¹, D-Pro³, N-Amino-4-methylimidazol-2-one⁴]GHRP-6 (Ala-D-Trp-D-Pro-(N-amino-4-methyl-imidazol-2-one)-D-Phe-Lys-NH₂, 425B).

Solid-phase synthesis of [N-amino-4-methylmidazolin-2-one⁴]GHRP-6 analogs

A series of [N-amino-4-methylimidazolin-2-one⁴] GHRP-6 analogs were prepared by a general method employing Fmoc-Rink Amide Resin (300 mg, loading 0.9 mmol/g, 0.27 mmol). The resin was washed for 2×1 min with DMF and for 2×1 min with DCM. The Fmoc group was removed by treating the solid support with 5 mL of a 20% piperidine in DMF for 2×1 min and for 2×10 min. After the resin was washed with DMF for 2×1 min and with DCM for 2×1 min, Fmoc-Lys(Boc) (375 mg, 0.81 mmol, 3 eq) was coupled following the standard conditions: DIEA (282 μL, 1.62 mmol, 6 eq) was added to a solution of the amino acid in 3 mL of DMF, followed by the addition of HBTU (322 mg, 0.81 mmol, 3 eq) in 2 mL of DMF, and after activation for 2 min, the mixture was added to the resin. After 1 h the solid support was washed with DMF for 2×1 min and DCM for 2×1 min. A negative ninhydrin test indicated that the coupling was complete. After Fmoc cleavage and resin washing as described above, (2'S)- or (2'R)-1-((diphenylmethylene)amino)-3-(3'-phenyl-2'-propanoate)-4-methylimidazolin-2-one (S- or R-4) (230 mg, 0.54 mmol, 2 eq) was coupled to the resin using HBTU (215 mg, 0.54 mmol, 2 eq) and DIEA (188 μL, 1.1 mmol, 4 eq) in 5 mL of DMF for 16 h. After the resin was washed with DMF for 2×1 min and DCM for 2×1 min, an aliquot of 10 mg of dry resin was treated with 1 mL of TFA:H₂O (95:5) and the residue was examined by HPLC to verify that coupling was complete. Removal of the diphenylketamine was carried out using a 5 mL solution of 1.5 M hydroxylamine hydrochloride in pyridine at 60° C. with sonication for 16 h. After the resin was washed with DMF for 2×1 min and DCM for 2×1 min, the peptide was elongated with either Fmoc-D- or L-Lys(Boc) (1 g, 2.16 mmol, 8 eq), or Fmoc-D- or L-Pro (729 mg, 2.16 mmol, 8 eq), which was pre-activated with diisopropyl carbodiimide (167 μL, 1.1 mmol, 4 eq) in 5 mL of DCM for 1 min prior to addition to the resin and shaken for 16 h. Double coupling was performed to achieve a higher conversion, as monitored by HPLC analysis of the cleavage product from treatment of 10 mg of resin with 1 mL of TFA:H₂O (95:5). The final resin-bound peptides were prepared by removal of the Fmoc groups, resin washings and elongation of the peptides with Fmoc-D-Trp(Boc) (427 mg, 0.81 mmol, 3 eq) using HBTU (322 mg, 0.81 mmol, 3 eq) and DIEA (282 μL, 1.62 mmol, 6 eq) in 5 mL of DMF for 1 h, followed by Boc-His(Trt) (201.5 mg, 0.41 mmol, 3 eq) or Boc-Ala (77 mg, 0.41 mmol, 3 eq) using HBTU (161 mg, 0.41 mmol, 3 eq) and DIEA (141 μL, 0.81 mmol, 6 eq) in 5 mL of DMF. Final cleavage of the solid support was performed using 5 mL of a solution of TFA:TES:H₂O (95:2.5:2.5) for 1 h. The resin was filtered off, and the filtrate was treated with cold diethyl ether to precipitate the [N-amino-4-methylimidazolin-2-one⁴]GHRP-6 analogs as white solids, which were washed twice with diethyl ether, freeze-dried and purified by semi-preparative HPLC.

[His¹, Lys³, N-Amino-4-methylimidazolin-2-one⁴] GHRP-6 (His-D-Trp-Lys-(N-amino-4-methyl-imidazol-2-one)-D-Phe-Lys-NH₂, 422A)

LCMS (5-50% MeOH, 12 min) R.T.=10.2 min; (5-50% MeCN, 12 min) R.T.=8.4 min; HRMS Calcd m/z for C₄₂H₅₈N₁₃O₆ 840.4627. Found 840.4629.

[Ala¹, Lys³, N-Amino-4-methylimidazolin-2-one⁴] GHRP-6 (Ala-D-Trp-Lys-(N-amino-4-methyl-imidazolin-2-one)-D-Phe-Lys-NH₂, 422B)

LCMS (10-40% MeOH, 12 min) R.T.=8.3 min; (5-50% MeCN, 12 min) R.T.=5.1 min; HRMS Calcd m/z for C₃₉H₅₆N₁₁O₆ 774.4410. Found 774.4414.

[His¹, D-Lys³, N-Amino-4-methylimidazolin-2-one⁴] GHRP-6 (His-D-Trp-D-Lys-(N-amino-4-methyl-imidazolin-2-one)-D-Phe-Lys-NH₂, 423A)

LCMS (5-50% MeOH, 12 min) R.T.=7.7 min; (5-50% MeCN, 12 min) R.T.=9.1 min; HRMS Calcd m/z for C₄₂H₅₈N₁₃O₆ 840.4627. Found 840.4626.

[Ala[1], D-Lys[3], N-Amino-4-methylimidazolin-2-one[4]]GHRP-6 (Ala-D-Trp-D-Lys-(N-amino-4-methyl-imidazolin-2-one)-D-Phe-Lys-NH$_2$, 423B)

LCMS (10-40% MeOH, 12 min) R.T.=10.6 min; (10-40% MeCN, 12 min) R.T.=9.8 min; HRMS Calcd m/z for $C_{39}H_{56}N_{11}O_6$ 774.4410. Found 774.4411.

[His[1], Pro[3], N-Amino-4-methylimidazolin-2-one[4]] GHRP-6 (His-D-Trp-Pro-(N-amino-4-methyl-imidazolin-2-one)-D-Phe-Lys-NH$_2$, 424A)

LCMS (20-60% MeOH, 12 min) R.T.=5.8 min; (10-50% MeCN, 12 min) R.T.=5.5 min; HRMS Calcd m/z for $C_{41}H_{53}N_{12}O_6$ 809.4205. Found 809.4211.

[Ala[1], Pro[3], N-Amino-4-methylimidazolin-2-one[4]] GHRP-6 (Ala-D-Trp-Pro-(N-amino-4-methyl-imidazolin-2-one)-D-Phe-Lys-NH$_2$, 424B)

LCMS (20-60% MeOH, xx min) R.T.=9.8 min; (10-50% MeCN, 12 min) R.T.=10.2 min; HRMS Calcd m/z for $C_{38}H_{51}N_{10}O_6$ 743.3988. Found 743.3988.

[His[1], D-Pro[3], N-Amino-4-methylimidazolin-2-one[4]] GHRP-6 (His-D-Trp-D-Pro-(N-amino-4-methyl-imidazolin-2-one)-D-Phe-Lys-NH$_2$, 425A)

LCMS (20-50% MeOH, 12 min) R.T.=7.4 min; (10-50% MeCN, 12 min) R.T.=9.5 min; HRMS Calcd m/z for $C_{41}H_{53}N_{12}O_6$ 809.4205. Found 809.4204.

[Ala[1], D-Pro[3], N-Amino-4-methylimidazolin-2-one[4]]GHRP-6 (Ala-D-Trp-D-Pro-(N-amino-4-methyl-imidazolin-2-one)-D-Phe-Lys-NH$_2$, 425B)

LCMS (20-60% MeOH, 12 min) R.T.=10.2 min; (10-50% MeCN, 12 min) R.T.=10.2 min; HRMS Calcd m/z for $C_{38}H_{51}N_{10}O_6$ 743.3988. Found 743.3988.

Example 2

Synthesis and Application of Amino-Imidazolidinone, Tetrahydropyrimidinone and Dihydrodiazapinone Peptidomimetics Methods
General.

Polystyrene Rink Amide resin (0.80 mmol/g, 75-100 mesh) was purchased from Advanced Chemtech® and the loading of the resin was determined by standard Fmoc loading test (C. Kay, O. E. Lorthioir, N. J. Parr, M. Congreve, S. C. McKeown, J. J. Scicinski, S. V. Ley. *Biotechnology and Bioengineering.* 2000/2001, 71: 110-118). Reagents including benzaldehyde, hydrazine hydrate, p-nitrophenyl chloroformate, tert-butylimino-tri(pyrrolidino)phosphorane (BTPP), potassium tert-butoxide, hydroxylamine hydrochloride, pyridine, triphosgene, formic acid (FA), N,N-diisopropylethylamine (DIEA) and 2,4,6-collidene, all were purchased from Aldrich and used without further purification. 1,2-Dibromoethane, 1,3-dibromopropane, and cis-1,4-dichloro-2-butene were purchased from Aldrich and purified by filtration through a plug of silica gel prior to use. Fmoc amino acids were purchased from Novabiochem® (EMD Bioscience® Inc., San Diego, Calif.) or GL Biochem Ltd. (Shangai, China). All solvents were obtained from VWR international. Anhydrous solvents (THF, MeCN, DCM and DMF) were obtained by passage through solvent filtration systems (Glass-Contour®, Irvine, Calif.). Analytical LCMS and HPLC analyses were performed on a 5 µM, 150 or 50 mm×4.6 mm C18 Phenomenex Gemini® column with a flow rate of 0.5 mL/min using a distilled water/MeOH gradient with 0.1% formic acid (FA). Peptide analogues were purified on a semi-preparative column (5 µM, 250 mm×21.2 mm, C18 Gemini column) using various gradients of distilled water/MeOH with 0.1% FA at a flow rate of 10.6 mL/min.

Fmoc-Based SPPS: Fmoc Deprotection and HBTU Couplings.

Peptide syntheses were performed under standard conditions (W. D. Lubell, J. W. Blankenship, G. Fridkin, and R. Kaul (2005) "Peptides." Science of Synthesis 21.11, Chemistry of Amides. Thieme, Stuttgart, 713-809) on an automated shaker using polystyrene Rink Amide resin (0.80 mmol/g, 75-100 mesh). Couplings of amino acids (3 equiv.) were performed in DMF using HBTU (3 equiv) as coupling reagent and DIEA (6 equiv). Fmoc deprotections were performed by treating the resin with 20% piperidine in DMF for 30 min. Resin was washed after each coupling and deprotection step sequentially with DMF (3×10 mL), MeOH (3×10 mL), THF (3×10 mL), and DCM (3×10 mL). The purity of peptide fragments was determined by LCMS analysis after cleavage and deprotection of a small aliquot of resin as described below.

Representative Protocol for Deprotection of Semicarbazone on Solid Support (as Described in: D. Sabatino, C. Proulx, S. Klocek, C. B. Bourguet, D. Boeglin, H. Ong, W. D. Lubell. Org. Lett. 2009, 11, 3650).

Resin-bound semicarbazone 5 (200 mg, 0.160 mmol) was treated with a stock solution of 1.5 M NH$_2$OH.HCl in pyridine (5 mL) and heated in a water bath with a sonicator at 60° C. for 12 h. The resin was filtered and washed with 10% DIEA: DMF (3×10 mL), DMF (3×10 mL), MeOH (3×10 mL), THF (3×10 mL), and DCM (3×10 mL). The extent of reaction conversion was monitored on an aliquot (3 mg) of resin, which was subjected to 1 mL of TFA/TES/H$_2$O (95:2.5:2.5, v/v/v) for resin cleavage, before filtration and analysis of the crude filtrate by LCMS. In cases where LCMS analysis revealed incomplete semicarbazone deprotection, the procedure was repeated.

Deprotection and Cleavage of N-amino Cyclic Urea Peptidomimetics 6-18 from the Resin.

The Rink resin-bound peptide was deprotected and cleaved from the support using a freshly made solution of TFA/H$_2$O/TES (95:2.5:2.5, v/v/v, 20 mL/g of peptide resin) at room temperature for 2 h. The resin was filtered and rinsed with TFA. The filtrate and rinses were concentrated until a crude oil persisted, from which a precipitate was obtained by addition of cold ether (10-15 mL). After centrifugation, the supernatant was removed and the crude peptide was taken up in aqueous acetonitrile (10% v/v) and freeze-dried to a white solid prior to analysis.

Analysis and Purification of N-amino Cyclic Urea Peptidomimetics.

Analyses and characterization of crude peptidomimetics were performed on either an Agilent Technologies® 1100 Series LCMS instrument with ESI ion-source, single quadropole mass detection and positive mode ionization or a ThermoFinnigan® LCQ Advantage MS, with ESI ion-source, ion-trap mass detection, and positive mode ionization, equipped with a Gilson® LC 322 pump containing auto-sampler and injector. Peptidomimetic samples were dissolved in 10% H$_2$O in MeOH. The LCMS analyses were performed on a Gemini® C18 reverse-phase column (150×4.60 mm, 5 µm), using a binary solvent system consisting of 0.1% FA in H$_2$O, and 0.1% FA in MeOH at a flow rate of 0.5 mL/min and UV detection at 254 nm. Linear gradients of the mobile phase (0.1% FA in methanol, 2-80% over 15 min) were used for analyses of crude peptides.

Purification of peptides was conducted on a Waters® PrepLC instrument equipped with a reverse-phase Gemini® C18 column (250×21.2 mm, 5 µm), using binary solvent systems consisting of 0.1% FA in $H_2O$, and 0.1% FA in MeOH at a flow rate of 10.6 mL/min and UV detection at 214 nm. Fractions containing pure peptidomimetic were combined, freeze-dried and lyophilized to a white powder. Each purified peptidomimetic sample was analyzed for purity by LCMS with a Gemini® C18 reverse-phase column (150×4.60 mm, 5 µm) at a flow rate of 0.5 mL/min and UV detection at 214 nm. The purity of each compound was analysed using both a binary solvent system consisting of MeOH in $H_2O$ with 0.1% FA, and a solvent system consisting of acetonitrile in $H_2O$ with 0.1% FA, with solvent gradients of 2-80% and 2-40%, respectively.

Circular Dichroism (CD) Spectroscopy.

CD spectra were recorded using a Chirascan® CD Spectrometer (Applied Photophysics®, Leatherhead, United Kingdom) using a 1.0 cm path-length quartz cell containing a 20 µM solution of peptide analogue dissolved in Milli-Q® water. The experimental settings were: 1 nm bandwidth; 0.5 nm step size; 3 sec sampling time.

Intercalation of CyQUANT NF® Fluodye (Adapted from: Boutard, N.; Turcotte, S.; et al. J. Pep. Sci. 2011, 17, 288-296).

Immune cell proliferation was assessed by DNA intercalation of CyQUANT NF® fluorescent dye (Invitrogen, Carlsbad, Calif., USA). Essentially, human TF-1 cells (CRL-2003, American Type Culture Collection) were cultured in complete RPMI 1640 (WISENT Inc., Montréal, Quebec, Canada) supplemented with human GM-CSF (2 ng/ml, PeptroTech, Rocky Hill, N.J., USA). Cells (passage 5 and at least 85% viable, as verified by trypan blue dying) were reincorporated into RPMI 1640 medium deprived of phenol red (Gibco Invitrogen®, Carlsbad, Calif., USA) and of growth factors [i.e. fetal bovine serum (FBS) and GM-CSF] for 18 h and split ($5×10^3$ cells in 200 µL/well) into 96-well non-adherent flat bottom culture plates (Sarstedt®, Nümbrecht, Germany). Following 15 min pre-incubation with peptide or peptidomimetic (1 µM), the cells were treated with human IL-1β (25 ng/mL, PeptroTech®, Rocky Hill, N.J., USA) and re-incubated. After 48 h, the cells were centrifuged for 7 min at 300 g, reincorporated into Hank's Buffered Salt Solution (1×HBSS, 50 µL/well, Gibco Invitrogen®, Carlsbad, Calif., USA) and transferred into a 96-well polystyrene black plate (Corning Incorporated, Corning, N.Y., USA). An additional 50 µL solution made of CyQUANT NF® dye (component A, 1×) and CyQUANT NF™ delivery agent (component B, 1×) in 1×HBSS was added to the cells in each well, which were covered with aluminum foil and incubated for 45 min. Fluorescence intensity was measured using a microplate reader (Perkin Elmer Wallac Envision® 2104; Perkin Elmer®, California, USA) with excitation at 485 nm and emission detection at 530 nm (FITC 485 and FITC 531 filters, respectively). Hexaplicate experiments were repeated three times and results were analyzed by one-way analysis of variance (ANOVA) factoring for treatments, and data are presented as mean±standard error of the mean (SEM).

HEK Blue SEAP Reporter Gene Assay.

Activation of the NF-κB pathway upon interaction with IL-1β (or IL-33) receptor complex at the membrane was assessed via HEK-Blue SEAP reporter gene assay (InvivoGen®, California, USA). Basically, HEK Blue IL-33/IL-1β sensor cells were cultured in growth medium made of complete Dulbecco's modified Eagle medium (DMEM; 4.5 g/L glucose, 2 mM L-glutamine, 100 mM sodium pyruvate, 10% fetal bovine serum, 50 U/mL penicillin, 50 µg/mL streptomycin; Gibco Invitrogen®, Ontario, Canada) supplemented with selection antibiotics (30 µg/mL Blasticidin®, 200 µg/mL HygroGold® and 100 µg/mL Zeocin®; InvivoGen, California, USA). Upon reaching almost 70% confluency, HEK Blue cells were reincorporated into complete DMEM medium and split ($2.5×10^4$ cells in 180 µL/well) into 96-well membrane-treated flat bottom culture plates (Plate #3595, Corning Life Sciences, Massachusetts, USA). Cells were pretreated with 10 µL of peptide or peptidomimetic (1 µM) for 15 min., after which 10 µL of human IL-1β (2.5 ng/mL, PeproTech®, Rocky Hill, N.J., USA) was added. Following 24 h of incubation, 40 µL of the cells supernatant was added to a UV-transparent 96-well plate (Plate #3635, Corning Life Sciences®, Massachusetts, USA) already filled with 160 µL of resuspended Quanti-Blue® dye (1×, InvivoGen, California, USA). The plate was covered and incubated for 20 min. The level of SEAP was measured by reading absorbance (or optical density, OD) at 620 nm using a multiplate reader equipped with a monochromator (Perkin Elmer Wallac Envision® 2104; Perkin Elmer®, California, USA). Hexaplicate results were normalized over complete DMEM background signal and analyzed by one-way analysis of variance (ANOVA) factoring for treatments, and data are presented as mean±standard error of the mean (SEM).

A universal approach has been developed for the synthesis of N-amino cyclic urea peptidomimetics and their incorporation into peptide sequences, and featured by the construction of three types of N-amino cyclic urea residues: N-amino-imidazolidinone (Nai), N-amino-tetrahydropyrimidinone (Nap), and N-amino-dihydrodiazapinone (Nad) (FIG. 3). In light of the effects of ring size on amino lactam peptide conformation and activity (R. M. Freidinger, D. S. Perlow, D. F. Veber. J. Org. Chem. 1982, 47: 104-109), a method capable of producing 5-, 6, and 7-membered rings from a common intermediate was developed and evaluated at a strategic residue of a biologically active peptide.

N-Amino cyclic urea residues were introduced into peptides by an analogous solid-phase strategy to submonomer azapeptide synthesis, utilizing a method featuring selective installation and alkylation of a semicarbazone residue (Scheme 5) (D. Sabatino, C. Proulx, S. Klocek, C. B. Bourguet, D. Boeglin, H. Ong, W. D. Lubell. Org. Lett. 2009, 11, 3650-3653. b) D. Sabatino, C. Proulx, P. Pohankova, H. Ong, W. D. Lubell. J. Am. Chem. Soc. 2011, 133, 12493-12506). The intreleukin-1 (IL-1) receptor negative modulator 101.10, a D-heptapeptide (C. Quiniou et al. J. Immunol. 2008, 180, 6977-6987) and Growth Hormone-Releasing Peptide-6 (His-D-Trp-Ala-Trp-D-Phe-Lys-$NH_2$, GHRP-6), a synthetic hexapeptide with affinity for the ghrelin and CD36 receptors (C. Y. Bowers, A. O. Sartor, G. A. Reynolds, T. M. Badger. Endocrinology. 1991, 128, 2027-2035), both were selected as model peptides for developing this methodology, because of their interesting biology and challenging chemical structures. In particular, substitution of D-$Thr^3$ in 101.10 by Nai, Nap, and Nad, respectively, was explored to compare the conformation and activity of the N-amino cyclic urea derivatives with previously synthesized amino-γ-lactam analogues (A. G. Jamieson, N. Boutard, K. Beauregard, M. S. Bodas, H. Ong, C. Quiniou, S. Chemtob, W. D. Lubell. J. Am. Chem. Soc. 2009, 131, 7917-7927. b) L. Ronga, A. G. Jamieson, K.

Beauregard, C. Quiniou, S. Chemtob, W. D. Lubell. *Biopolymers*. 2010, 94, 183-191. c) N. Boutard, S. Turcotte, K. Beauregard, C. Quiniou, S. Chemtob, W. D. Lubell. *J. Peptide Sci.* 2011, 17, 288-296). GHRP-6 was scanned systematically with Nap to demonstrate the synthetic scope of the process, because the sequence possesses nucleophilic side chains of His, Trp, and Lys residues. In addition, five GHRP-6 analogues were pursued containing Nai and Nad substitutions at key positions (D. Sabatino et al., supra).

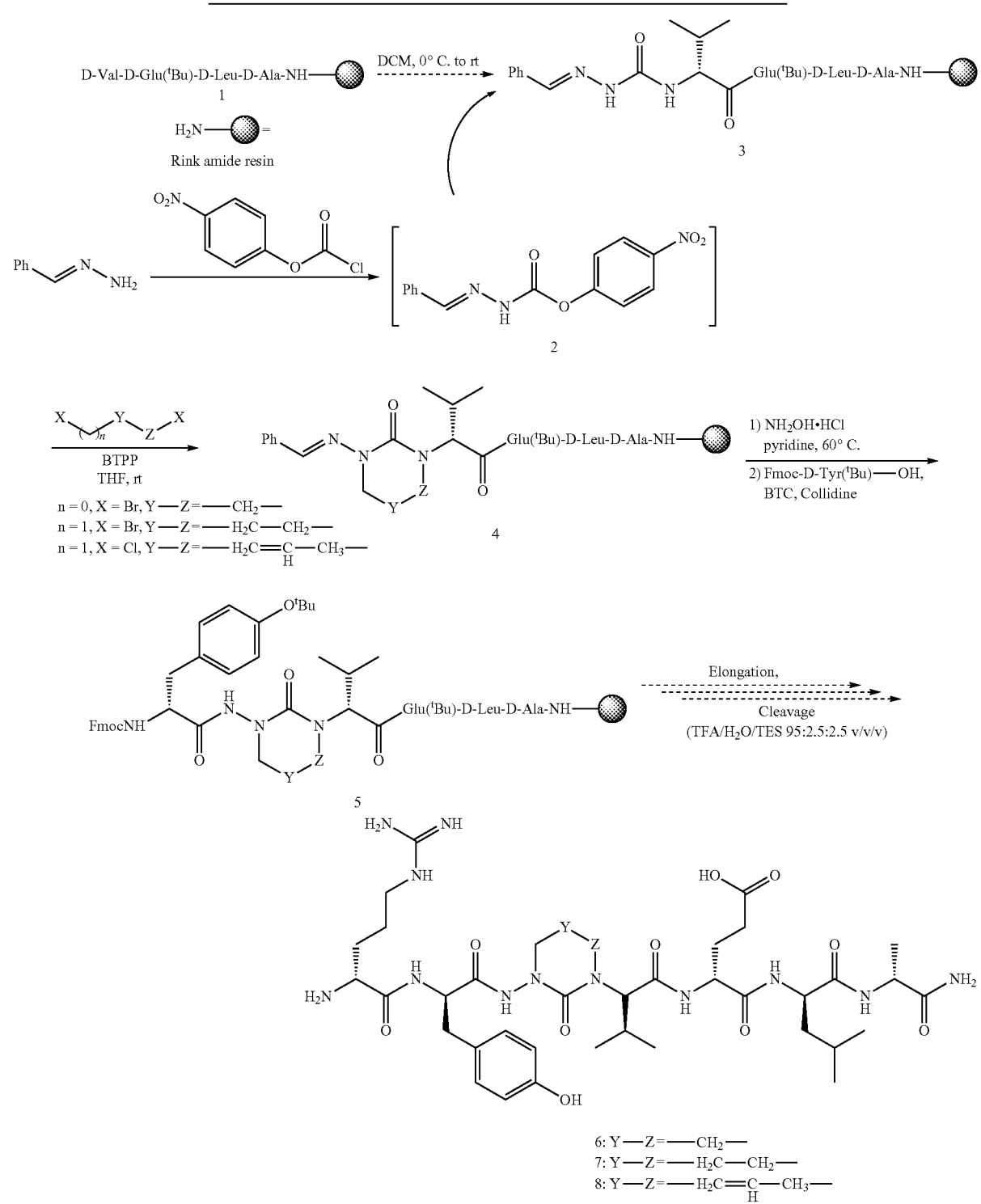

Semicarbazone N-alkylation was best achieved by swelling peptide resin 3 in THF and treating with 500 mol % of the non-ionic phosphazene base BTPP and 500 mol % of the respective biselectrophile:1,2-dibromoethane, 1,3-dibromopropane and cis-1,4-dichloro-2-butene (Scheme 5). Alkylation of the aza-glycine residue is presumed to occur initially at the acidic nitrogen of the semicarbazone (D. Sabatino et al., supra), followed by the urea nitrogen. Attempts to employ potassium t-butoxide as base gave less satisfying results. Certain alkyl halides, such as 1,2-diiodoethane, failed to give the alkylation product, likely due to elimination under the basic conditions. In contrast to cis-1,4-dichloro-2-butene, which was pre-organized for ring formation and afforded material exhibiting molecular ions corresponding to the 7-membered cyclic urea 4, the corresponding 1,4-dihalobutanes gave predominantly alkyl-bridged products as indicated by the molecular ions of cross-linked dimers in the LC-MS chromatogram of the crude mixture after resin cleavage. Although molecular ions corresponding to ring formation were readily observed in the synthesis of the analogues of 101.10, formation of the cyclic urea moiety within the GHRP-6 analogues was often difficult, likely due to side-chain nucleophilicity and a predilection for the sequence to adopt secondary structure on resin. Incomplete alkylation and unidentified side-reactions gave mixtures of products that often made separation of the final crude GHRP-6 peptidomimetics challenging. For example, seven-member ring formation was particularly difficult, due to less favorable kinetics for closure of the larger ring, and multiple attempts to substitute Nad at the D-Trp$^2$, Ala$^3$ and D-Phe$^4$ positions of GHRP-6 were unsuccessful.

After alkylation, the semicarbazone was removed using hydroxylamine hydrochloride in pyridine (D. Sabatino et al., supra). In contrast to the syntheses of parent peptides, milder coupling reagents (i.e., HBTU) often gave insufficient yields for completion of the cyclic urea peptide sequences, suggesting that on solid support, the N-amino cyclic urea moiety may induce secondary structures that hinder coupling. In these cases, triphosgene proved the reagent of choice for activation and addition of the remaining amino acids (E. Falb, T. Yechezkel, T. Y. Salitra, Y., C. Gilon. *J. Pept. Res.* 1999, 53, 507-517). After resin cleavage with TFA, analytical HPLC showed peaks having molecular ions corresponding to N-amino cyclic urea peptides with crude purities ranging from 8-53% (Table 10), and were isolated by reverse-phase HPLC in ≥95% purity, eluting with a gradient of MeOH in H$_2$O.

Figure 4:
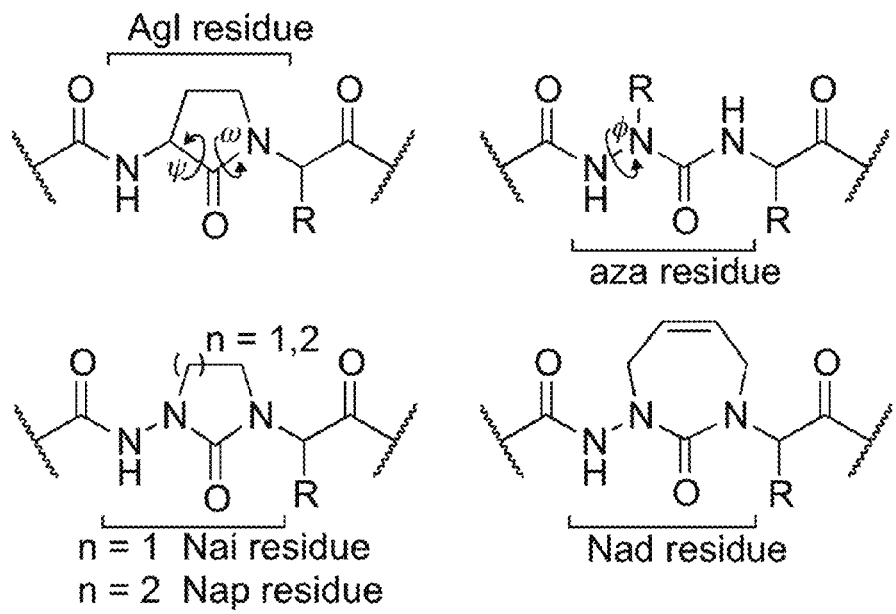
FIG. 4 shows the conformational restriction of the peptide backbone via amino-lactam, azapeptide and N-amino cyclic ureas.

Circular dichroism (CD) spectroscopy in water was used to study the influence on conformation of the different ring constraints at the 3-position of 101.10 (FIG. 4). CD spectra were plotted with the corresponding [(R)-Agl$^3$]-101.10 spectrum to compare the influence of replacement of the chiral α-carbon of the γ-lactam by nitrogen in the Nai residue. The parent peptide, 101.10 exhibited a CD curve shape characteristic of a random coil conformation in water, albeit CD spectra were inverted for the D-peptide and analogs relative to those characteristic of L-peptide structures (D. Sabatino et al., supra). N-Amino cyclic urea peptidomimetics of 101.10 exhibited curve shapes characteristic of secondary structure. For example, the Nai and Agl five-member analogues, both exhibited curve shapes indicative of turn conformations; however, the positions of their positive and negative maxima, as well as the intensity of their ellipticity differed. The lower ellipticity of [Nai$^3$]-101.10 (7) may likely be due to the absence of a chiral center within the 5-membered ring. Moreover, the CD curve shapes of the [Nap$^3$]- and [Nad$^3$]-101.10 analogues (6 and 8) exhibited points of inflection near 205 nm and 215 nm, suggestive of turn-like character. Notably, the maxima and the intensity of the ellipticity were distinct for all four 101.10 analogues, suggesting peptide conformation varies subtly with the change in ring size and the absence of stereochemistry. Their effective synthesis from a common precursor and collective potential for exploring different conformational space suggest application of a combination of N-amino cyclic ureas to study peptide conformation-activity relationships.

Figure 5:
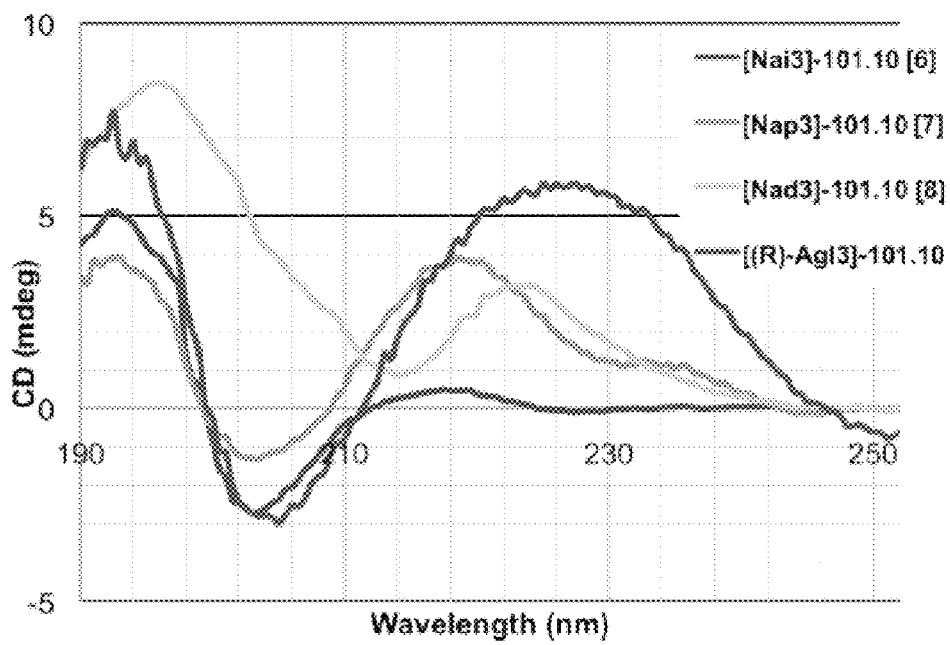
FIG. 5 shows circular dichroism spectra of N-amino cyclic ureas and (R)-Agl analogues of 101.10 in water.
Figure 6:
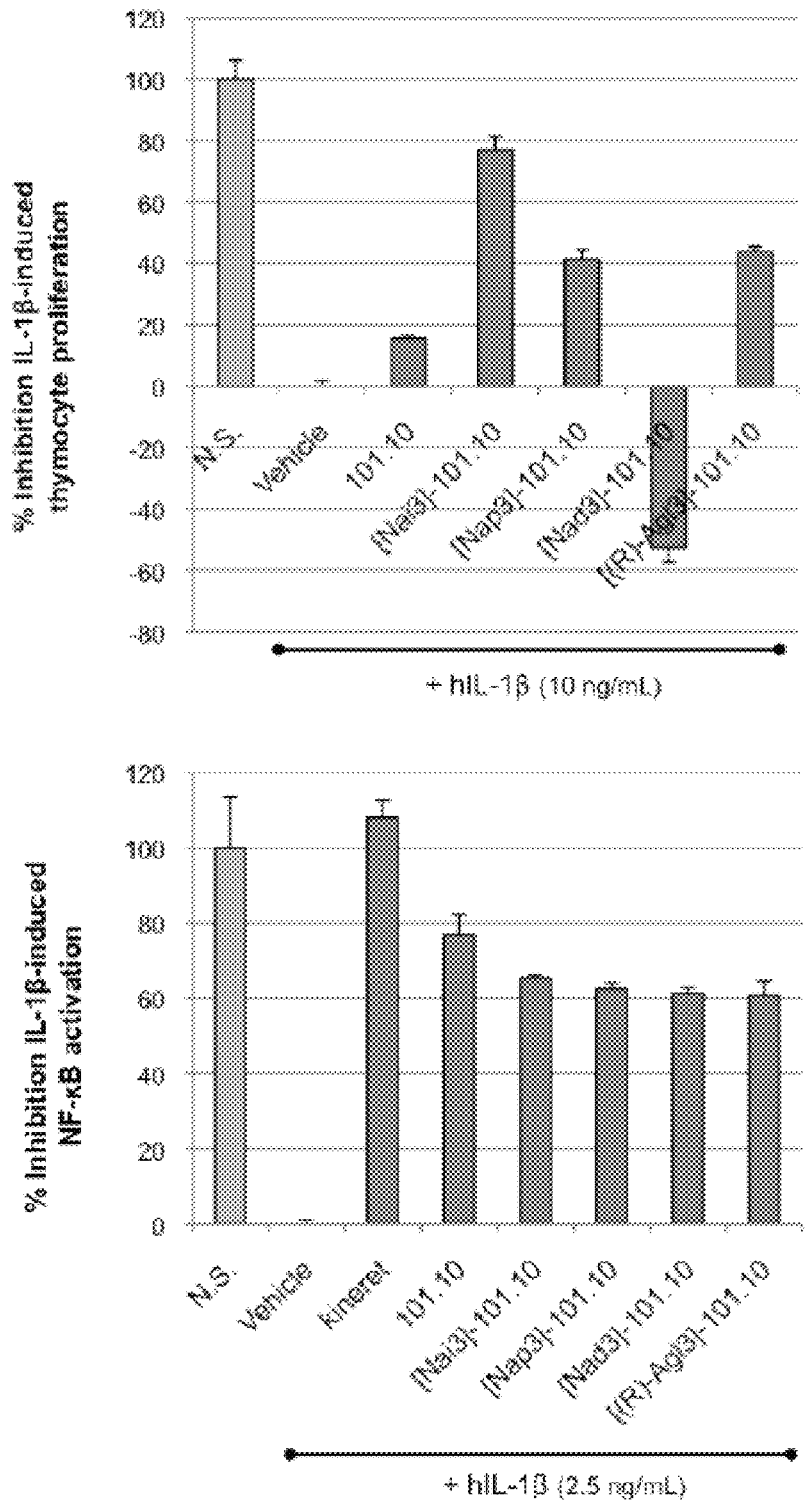
FIG. 6 shows the biological activity of analogues in IL-1β-induced thymocyte proliferation (upper panel) and NF-κB activation (lower panel). Results are presented as percentage of inhibition of IL-1β-stimulation of fluorescence and optical density at 620 nm, respectively. N.S. column represents cells that were not stimulated with IL-1β; vehicle column refers to the cells that were not treated by a peptide; sample columns were stimulated by an exogenous amount of human IL-1β.
Figure 7:
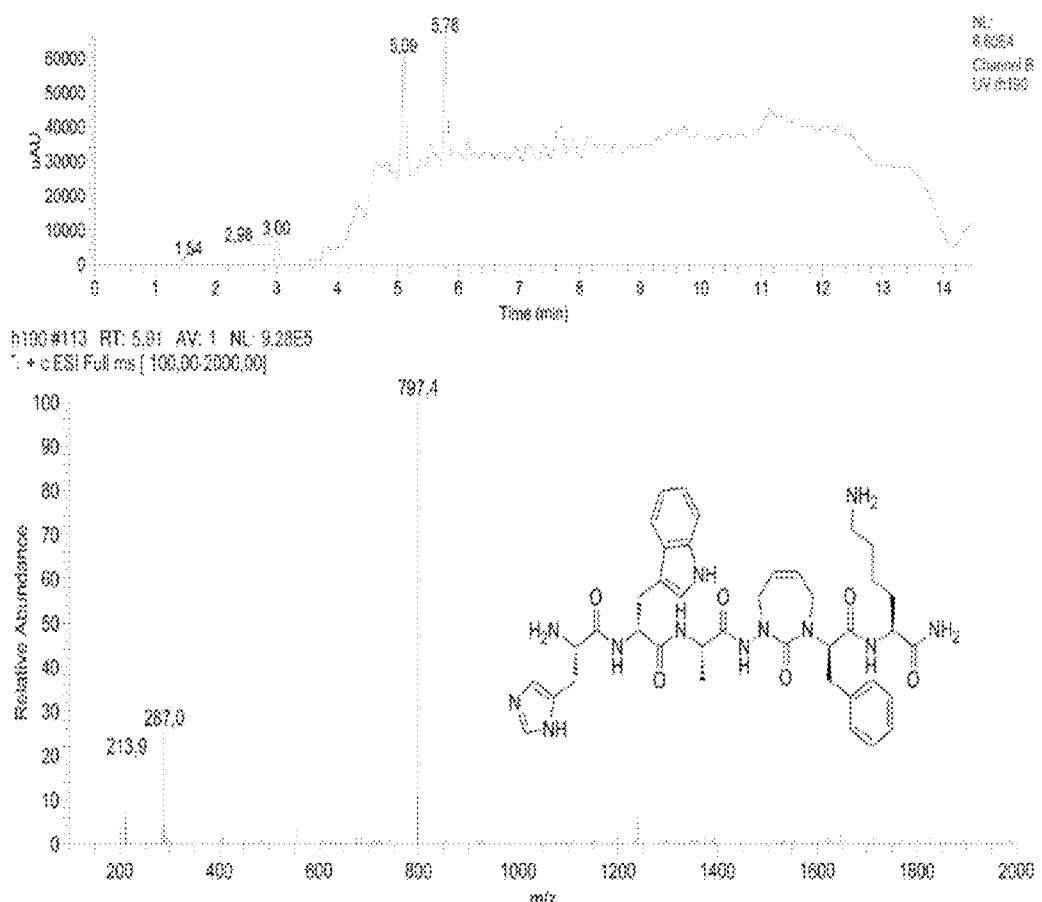
FIG. 7 shows HPLC/MS spectrographs of peptidomimetics described herein.
Figure 7:
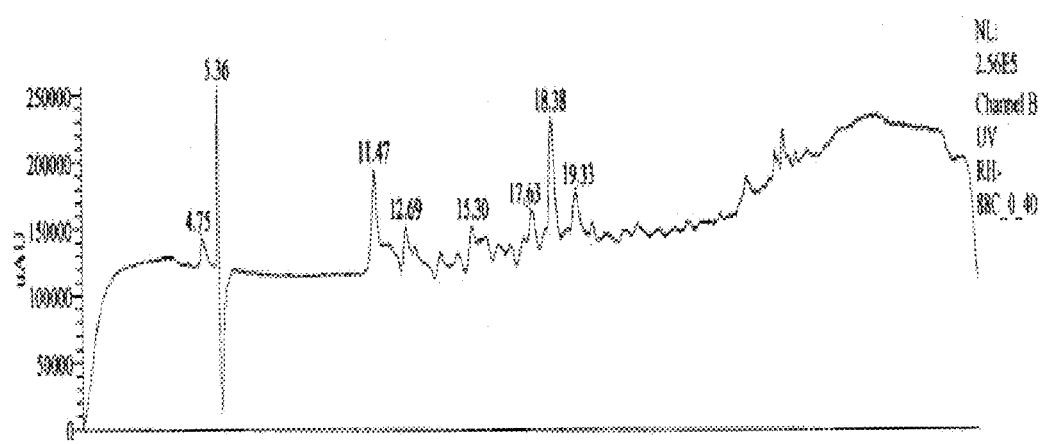
Figure 7:
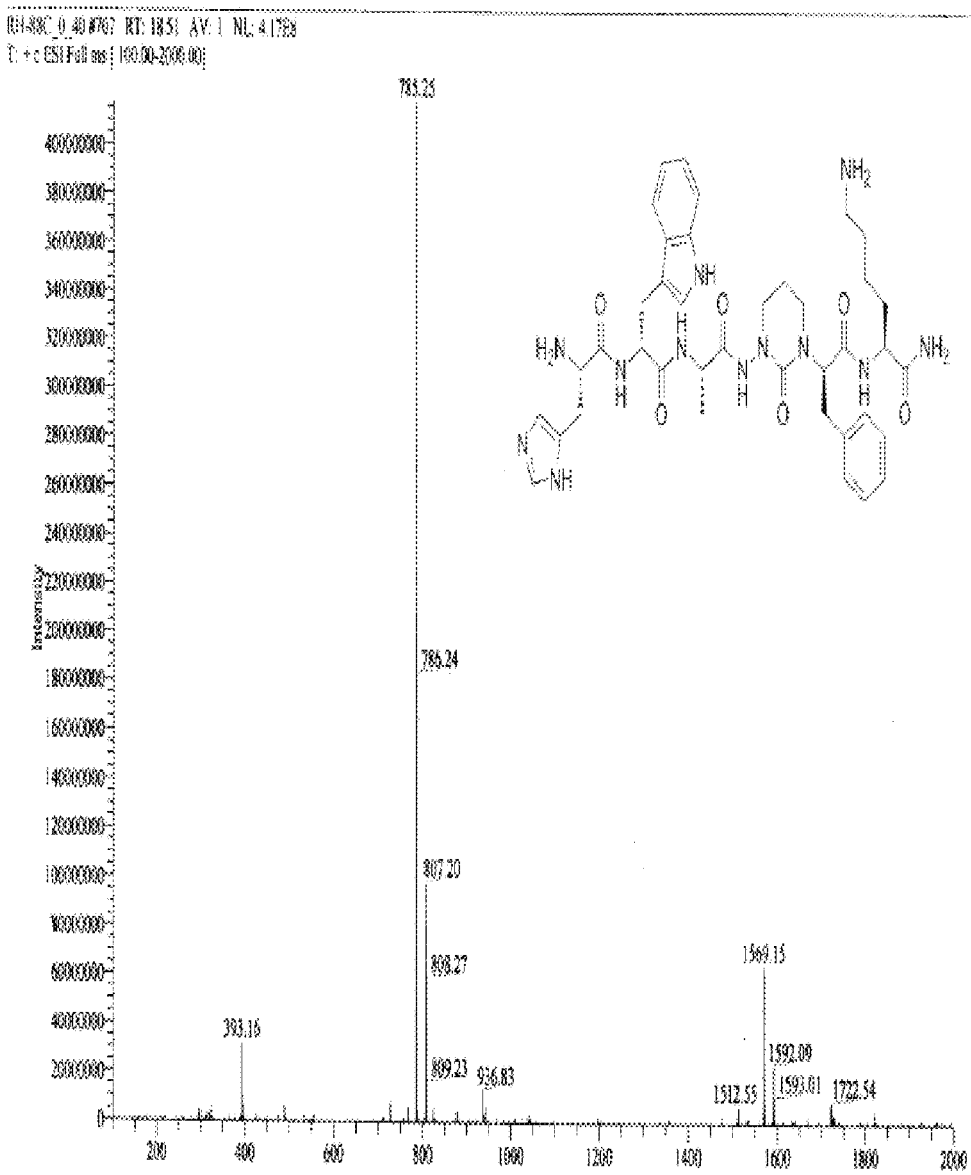

The biological activity of the N-amino cyclic ureas of 101.10 was measured in two distinct cellular assays: IL-1β-induced human thymocyte (TF-1) proliferation, and nuclear factor-κB (NF-κB) activation in HEK Blue cells (FIG. 5). In the former assay, the intensity of the fluorescent signal correlates with the degree of cell proliferation, which is induced by treatment with IL-1β. Although no peptide blocked completely the induced thymocyte proliferation, [Nai$^3$]-101.10 diminished 77% of IL-1β-induced proliferation, compared to 41% for [Nap$^3$]-101.10 and 15% for 101.10. Contrarily, [Nad$^3$]-101.10 exacerbated proliferation by 53% over the level of exogenous IL-1β. Relative to [(R)-Agl$^3$]-101.10, which diminished 41% of IL-1β-induced proliferation, the 5- and 6-member α-aminoaza-lactam analogues exhibited improved and similar activity.

TABLE 10

Yields and Purities of 101.10 and GHRP-6 N-Amino Cyclic Urea Analogues

| Entry | Peptide [a] | crude purity [%][b] | purity [%][c] | isolated yield [%][d] | HRMS m/z (calcd) | m/z (obsd) |
|---|---|---|---|---|---|---|
| 6 | D-Arg-D-Tyr-Nai-D-Val-D-Glu-D-Leu-D-Ala-NH$_2$ | 53 | 99 | 21 | 833.4628 | 833.4620 |
| 7 | D-Arg-D-Tyr-Nap-D-Val-D-Glu-D-Leu-D-Ala-NH$_2$ | 49 | 99 | 19 | 847.4785 | 847.4796 |
| 8 | D-Arg-D-Tyr-Nad-D-Val-D-Glu-D-Leu-D-Ala-NH$_2$ | 19 | 99 | 5 | 859.4785 | 859.4758 |
| 9 | His-Nai-Ala-Trp-D-Phe-Lys-NH$_2$ | 26 | 96 | 7 | 771.4049 | 771.4043 |
| 10 | His-D-Trp-Nai-Trp-D-Phe-Lys-NH$_2$ | 29 | 99 | 5 | 886.4471 | 886.4456 |
| 11 | His-D-Trp-Ala-Nai-D-Phe-Lys-NH$_2$ | 14 | 99 | 6 | 771.4049 | 771.4038 |
| 12 | Nap-D-Trp-Ala-Trp-D-Phe-Lys-NH$_2$ | 42 | 95 | 5 | 834.4410 | 834.4415 |
| 13 | His-Nap-Ala-Trp-D-Phe-Lys-NH$_2$ | 37 | 99 | 9 | 785.4206 | 785.4218 |
| 14 | His-D-Trp-Nap-Trp-D-Phe-Lys-NH$_2$ | 21 | 99 | 7 | 900.4628 | 900.4639 |
| 15 | His-D-Trp-Ala-Nap-D-Phe-Lys-NH$_2$ | 29 | 99 | 11 | 785.4206 | 785.4212 |
| 16 | His-D-Trp-Ala-Trp-Nap-Lys-NH$_2$ | 8 | 99 | 2 | 824.4315 | 824.4323 |
| 17 | Nad-D-Trp-Ala-Trp-D-Phe-Lys-NH$_2$ | 16 | 98 | 4 | 846.4410 | 846.4421 |
| 18 | His-D-Trp-Ala-Nad-D-Phe-Lys-NH$_2$ | 20 | 99 | 3 | 797.4206 | 797.4199 |

[a] Bold lettering indicates N-Amino cyclic urea residue.
[b] RP-HPLC purity at 214 nm of crude peptide after resin cleavage and precipitation.
[c] RP-HPLC purity at 214 nm of purified peptide.
[d] Yields after purification by RP-HPLC were based on Fmoc loading of Rink amide. Analyses were preformed using MeOH/H$_2$O eluent (2-80% MeOH) containing 0.1% formic acid.

The NF-κB pathway is an intracellular inflammatory cascade activated by IL-1β binding to its membrane receptor (IL-1R), which upon nuclear translocation triggers activation of the SEAP reporter gene in HEK Blue cells. This SEAP reporter gene serves to trigger the expression of an alkaline phosphatase, which, in the presence of colored substrate, causes a shift in absorption at 620 nm. The level of NF-κB activation was ascertained by measuring sample optical density (OD620). Kineret, a competitive IL-1R antagonist, and 101.10 inhibited respectively NF-κB activation by 100% and 77%. The N-amino cyclic ureas diminished OD620 with varying efficacy. The most potent analogue was [Nai³]-101.10 which gave 65% inhibition; however, the [Nap³]-, [Nad³]- and [(R)-Agl³]-101.10 analogues exhibited similar inhibitory effects. With respect to their abilities to inhibit NF-κB activation, substitution of D-Thr³ in the parent peptide for N-amino cyclic ureas had beneficial anti-inflammatory effects; however, none demonstrated antagonism of IL-1β-induced effects on par with 101.10. The trade-off of the loss of the hydroxyethyl side-chain for the gain in conformational restriction may account for the tempered biological activity. In both assays, the 5- and 7-membered amino-aza-lactams exhibited the most and least efficacy, respectively. Considering the CD curves are distinct for these peptidomimetics, ring size may evidently influence the conformation and activity of the peptide analogues.

The LCMS and CD characterization of products from the synthesis of N-amino cyclic urea peptide illustrate that mimics bearing 5-, 6-, and 7-membered rings may be prepared from a common intermediate on solid-phase. These novel peptidomimetic scaffolds possess achiral heterocycles, which combine electronic and structural constraints to induce conformational rigidity. Study of this approach to make N-amino cyclic ureas at the 3-position of 101.10 which were examined by CD spectroscopy demonstrated their potential to induce different peptide turn conformations contingent on ring size. Their collective use for assessing structure-activity relationships of biologically active peptides has been demonstrated in the study of the IL-1 allosteric modulator 101.10 using IL-1β-induced human thymocyte proliferation and nuclear factor-κB (NF-κB) activation assays. In these biological assessments of effects of constraint at the 3-position, the 5-member [Nai³]-101.10 analog exhibited better efficacy relative to the 6- and 7-member counterparts. Moreover, [Nai³]-101.10 exhibited better inhibitory activity in the proliferation assay than the α-amino-γ-lactam analog, [(R)-Agl³]-101.10. An effective method for systematically introducing N-amino cyclic ureas of varying ring-sizes along peptide sequences offers a powerful means for employing conformational constraint to investigate structure-activity relationships towards understanding of active conformations of biologically relevant peptides.

Characterization of GHRP-6 and 101.10 Analogues

6: [Nai]³-101.10

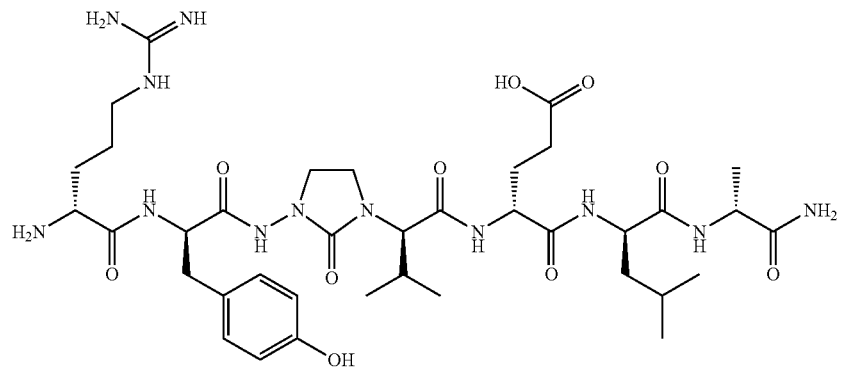 [SMILES: CC(C)C[C@@H](NC(=O)[C@@H](CCC(=O)O)NC(=O)[C@@H](C(C)C)N1CCN(NC(=O)[C@@H](Cc2ccc(O)cc2)NC(=O)[C@H](N)CCCNC(=N)N)C1=O)C(=O)N[C@H](C)C(N)=O]

LCMS (2-80% MeOH, 15 min) R.T.=2.60 min; (0-40% MeCN, 15 min) R.T.=2.77 min; HRMS Calcd m/z for $C_{37}H_{60}N_{12}O_{10}$ [M+H]+ 833.4628 m/z. found 833.4620 m/z.

7: [Nap]³-101.10

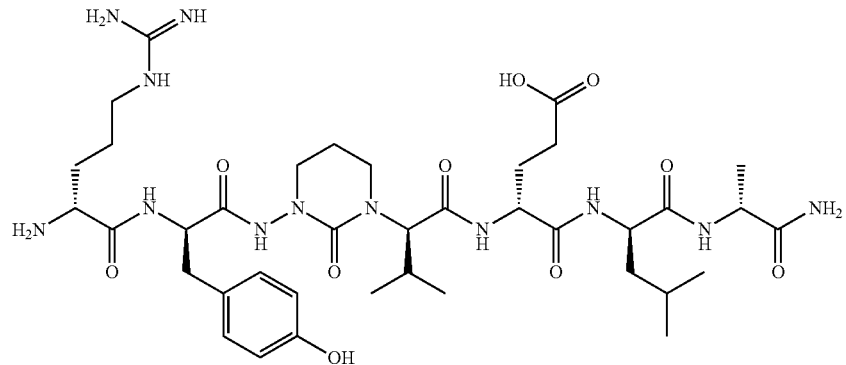 [SMILES: CC(C)C[C@@H](NC(=O)[C@@H](CCC(=O)O)NC(=O)[C@@H](C(C)C)N1CCCN(NC(=O)[C@@H](Cc2ccc(O)cc2)NC(=O)[C@H](N)CCCNC(=N)N)C1=O)C(=O)N[C@H](C)C(N)=O]

LCMS (2-80% MeOH, 15 min) R.T.=3.36 min; (0-40% MeCN, 15 min) R.T.=3.58 min; HRMS Calcd m/z for $C_{38}H_{62}N_{12}O_{10}$ [M+H]+ 847.4785 m/z. found 847.4796 m/z.
8: [Nad]³-101.10
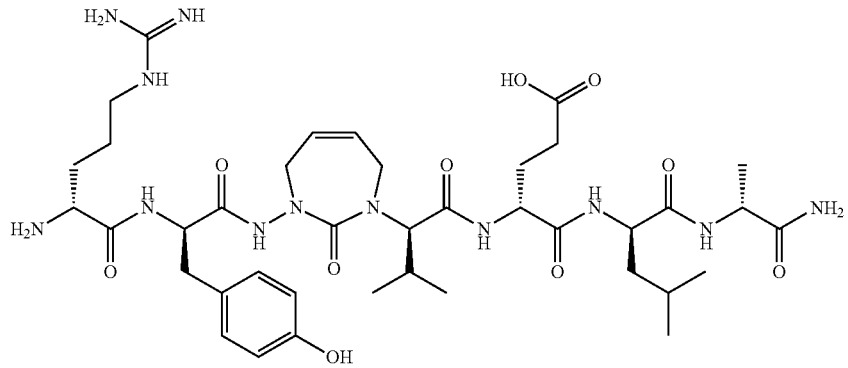 [SMILES: CC(C)C[C@@H](NC(=O)[C@@H](CCC(=O)O)NC(=O)[C@@H](C(C)C)N1CC=CCN(NC(=O)[C@@H](Cc2ccc(O)cc2)NC(=O)[C@H](N)CCCNC(=N)N)C1=O)C(=O)N[C@H](C)C(N)=O]
LCMS (2-80% MeOH, 15 min) R.T.=4.69 min; (0-40% MeCN, 15 min) R.T.=4.62 min; HRMS Calcd m/z for $C_{39}H_{62}N_{12}O_{10}$ [M+H]+ 859.4785 m/z. found 859.4758 m/z.
9: [Nai]²-GHRP-6
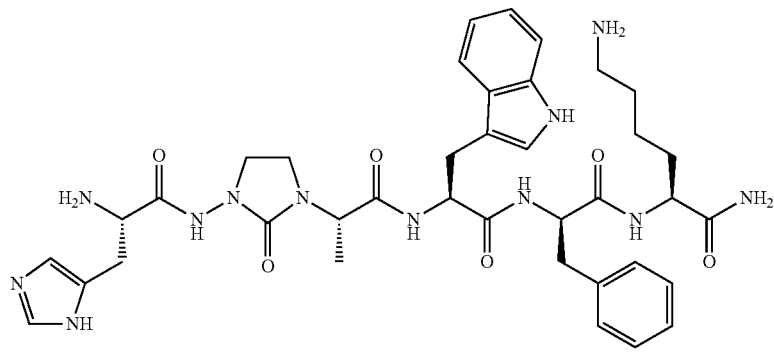 [SMILES: C[C@@H](C(=O)N[C@@H](Cc1c[nH]c2ccccc12)C(=O)N[C@H](Cc1ccccc1)C(=O)N[C@@H](CCCCN)C(N)=O)N1CCN(NC(=O)[C@@H](N)Cc2cnc[nH]2)C1=O]
LCMS (2-80% MeOH, 15 min) R.T.=2.64 min; (0-40% MeCN, 15 min) R.T.=2.53 min; HRMS Calcd m/z for $C_{38}H_{50}N_{12}O_{6}$ [M+H]+ 771.4049 m/z. found 771.4043 m/z.
10: [Nai]³-GHRP-6
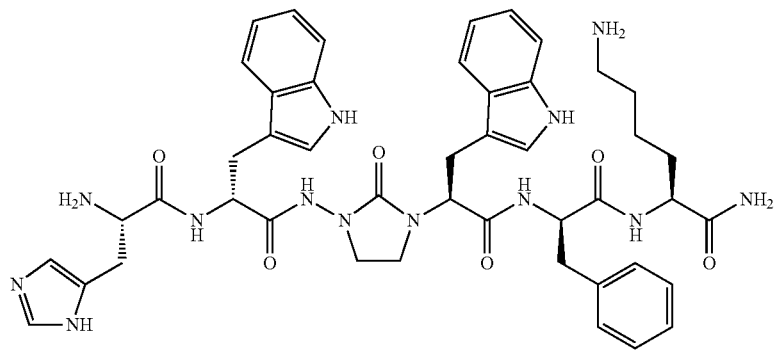 [SMILES: NCCCC[C@H](NC(=O)[C@@H](Cc1ccccc1)NC(=O)[C@H](Cc1c[nH]c2ccccc12)N1CCN(NC(=O)[C@@H](Cc2c[nH]c3ccccc23)NC(=O)[C@@H](N)Cc2cnc[nH]2)C1=O)C(N)=O]

LCMS (2-80% MeOH, 15 min) R.T.=5.25 min; (0-40% MeCN, 15 min) R.T.=5.63 min; HRMS Calcd m/z for $C_{46}H_{55}N_{13}O_6$ [M+H]+ 886.4471 m/z. found 886.4456 m/z.
11: [Nai]⁴-GHRP-6
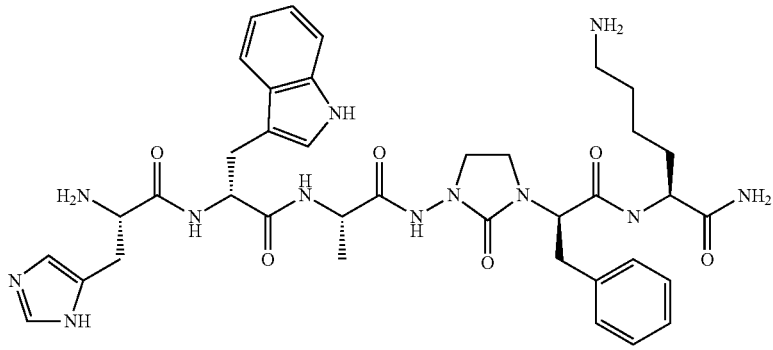 [SMILES: C[C@H](NC(=O)[C@@H](Cc1c[nH]c2ccccc12)NC(=O)[C@@H](N)Cc1cnc[nH]1)C(=O)NN1CCN([C@H](Cc2ccccc2)C(=O)N[C@@H](CCCCN)C(N)=O)C1=O]
LCMS (2-80% MeOH, 15 min) R.T.=4.81 min; (0-40% MeCN, 15 min) R.T.=4.55 min; HRMS Calcd m/z for $C_{38}H_{50}N_{12}O_6$ [M+H]+ 771.4049 m/z. found 771.4038 m/z.
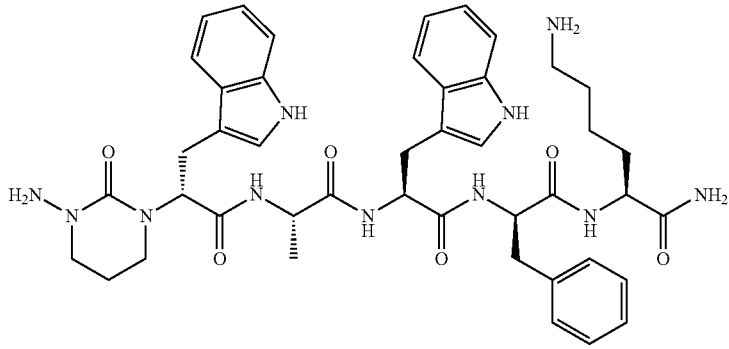 [SMILES: C[C@H](NC(=O)[C@@H](Cc1c[nH]c2ccccc12)N1CCCN(N)C1=O)C(=O)N[C@@H](Cc1c[nH]c2ccccc12)C(=O)N[C@H](Cc1ccccc1)C(=O)N[C@@H](CCCCN)C(N)=O]
LCMS (2-80% MeOH, 15 min) R.T.=7.89 min; (0-40% MeCN, 15 min) R.T.=7.09 min; HRMS Calcd m/z for $C_{44}H_{55}N_{11}O_6$ [M+H]+ 834.4410 m/z. found 834.4415 m/z.
13: [Nap]²-GHRP-6
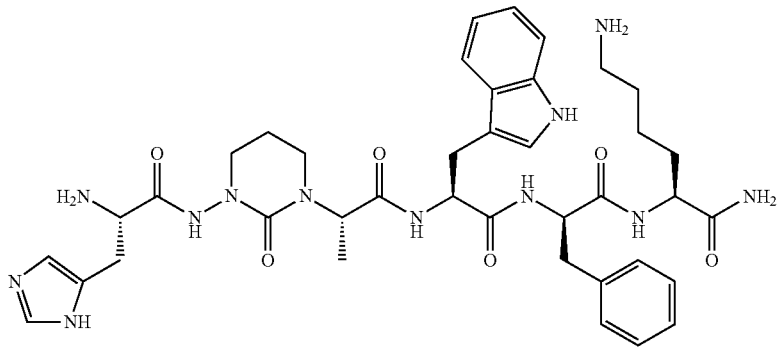 [SMILES: C[C@@H](C(=O)N[C@@H](Cc1c[nH]c2ccccc12)C(=O)N[C@H](Cc1ccccc1)C(=O)N[C@@H](CCCCN)C(N)=O)N1CCCN(NC(=O)[C@@H](N)Cc2cnc[nH]2)C1=O]

LCMS (2-80% MeOH, 15 min) R.T.=3.30 min; (0-40% MeCN, 15 min) R.T.=2.84 min; HRMS Calcd m/z for $C_{39}H_{52}N_{12}O_6$ [M+H]+ 785.4206 m/z. found 785.4218 m/z.
14: [Nap]³-GHRP-6
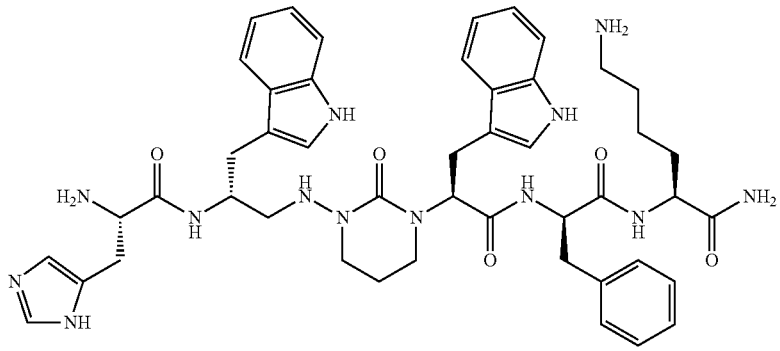 [SMILES: NCCCC[C@H](NC(=O)[C@@H](Cc1ccccc1)NC(=O)[C@H](Cc1c[nH]c2ccccc12)N1CCCN(NC[C@@H](Cc2c[nH]c3ccccc23)NC(=O)[C@@H](N)Cc2cnc[nH]2)C1=O)C(N)=O]
LCMS (2-80% MeOH, 15 min) R.T.=9.84 min; (0-40% MeCN, 15 min) R.T.=9.60 min; HRMS Calcd m/z for $C_{47}H_{57}N_{13}O_6$ [M+H]+ 900.4628 m/z. found 900.4639 m/z.
15: [Nap]⁴-GHRP-6
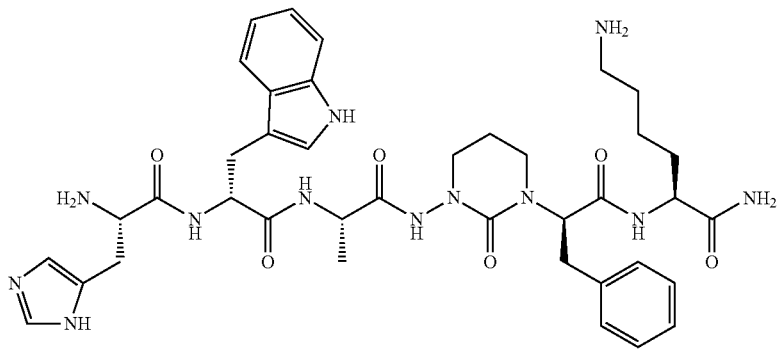 [SMILES: C[C@H](NC(=O)[C@@H](Cc1c[nH]c2ccccc12)NC(=O)[C@@H](N)Cc1cnc[nH]1)C(=O)NN1CCCN([C@H](Cc2ccccc2)C(=O)N[C@@H](CCCCN)C(N)=O)C1=O]
LCMS (2-80% MeOH, 15 min) R.T.=9.12 min; (0-40% MeCN, 15 min) R.T.=8.78 min; HRMS Calcd m/z for $C_{39}H_{52}N_{12}O_6$ [M+H]+ 785.4206 m/z. found 785.4212 m/z.
16: [Nap]⁵-GHRP-6
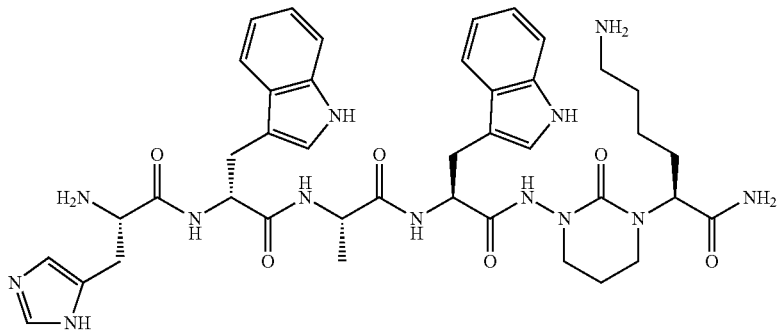 [SMILES: C[C@H](NC(=O)[C@@H](Cc1c[nH]c2ccccc12)NC(=O)[C@@H](N)Cc1cnc[nH]1)C(=O)N[C@@H](Cc1c[nH]c2ccccc12)C(=O)NN1CCCN([C@@H](CCCCN)C(N)=O)C1=O]

LCMS (2-80% MeOH, 15 min) R.T.=3.45 min; (0-40% MeCN, 15 min) R.T.=2.38 min; HRMS Calcd m/z for $C_{41}H_{53}N_{13}O_6$ [M+H]+ 824.4315 m/z. found 824.4323 m/z.

17: [Nad]$^1$-GHRP-6

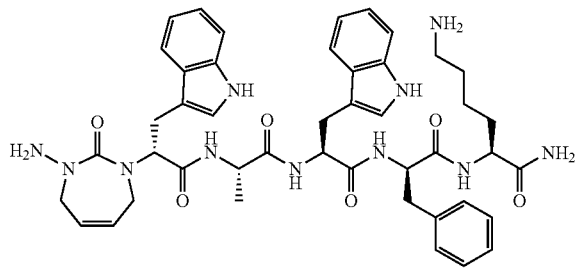 [SMILES: C[C@H](NC(=O)[C@@H](Cc1c[nH]c2ccccc12)N1CC=CCN(N)C1=O)C(=O)N[C@@H](Cc1c[nH]c2ccccc12)C(=O)N[C@H](Cc1ccccc1)C(=O)N[C@@H](CCCCN)C(N)=O]

LCMS (2-80% MeOH, 15 min) R.T.=9.47 min; (0-40% MeCN, 15 min) R.T.=10.01. min; HRMS Calcd m/z for $C_{45}H_{55}N_{11}O_6$ [M+H]+ 846.4410 m/z. found 846.4421 m/z.

18: [Nad]$^4$-GHRP-6

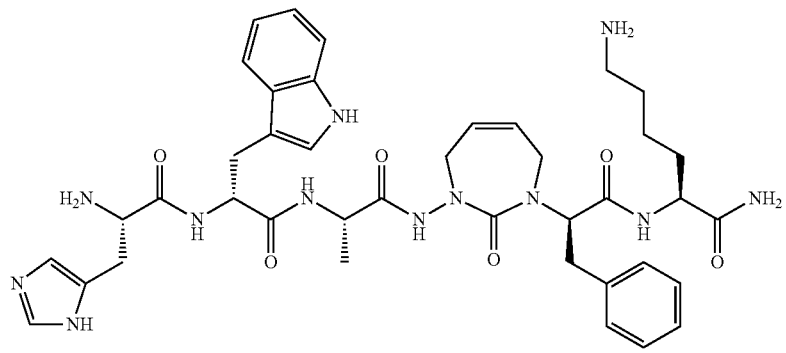

LCMS (2-80% MeOH, 15 min) R.T.=5.80 min; (0-40% MeCN, 15 min) R.T.=5.28 min; HRMS Calcd m/z for $C_{40}H_{52}N_{12}O_6$ [M+H]+ 797.4206 m/z. found 797.4199 m/z.

Example 3

N-amino-imidazolin-2one Peptide Mimics as Regulators of Inflammatory Responses in Macrophages in the Treatment of Atherosclerosis (Harb 2009), in Inflammatory-Related Diseases Involving Macrophageslglia Such as Age-Related Macular Degeneration Dry Form, Fibrinogenesis in Chronic Kidney Disease (Okamura 2009)

Figure 8:
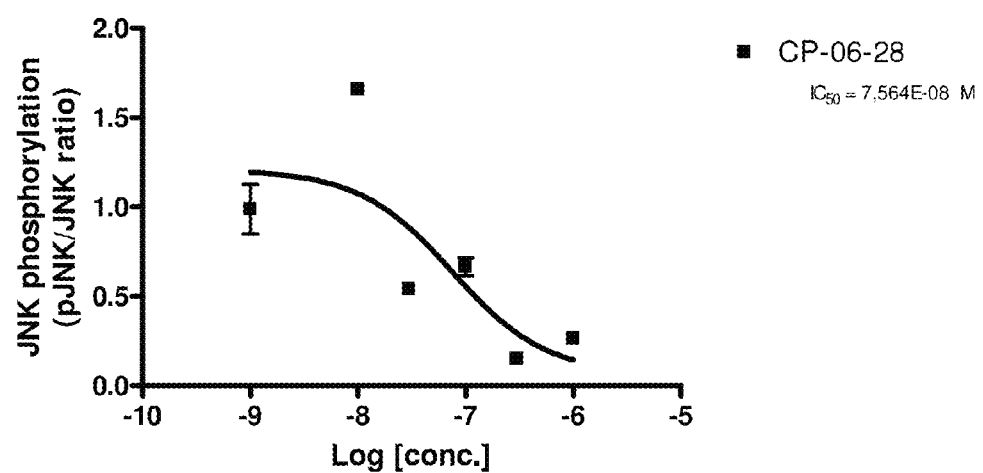
FIG. 8 shows the effect of the N-amino-imidazolin-2-one peptide mimic CP-06-28 (corresponding to N-amino cyclic urea peptidomimetic RS-31a) on JNK1/2 kinase phosphorylation induced by POVPC in the RAW 264.7 murine macrophages cell model.
Figure 9A:
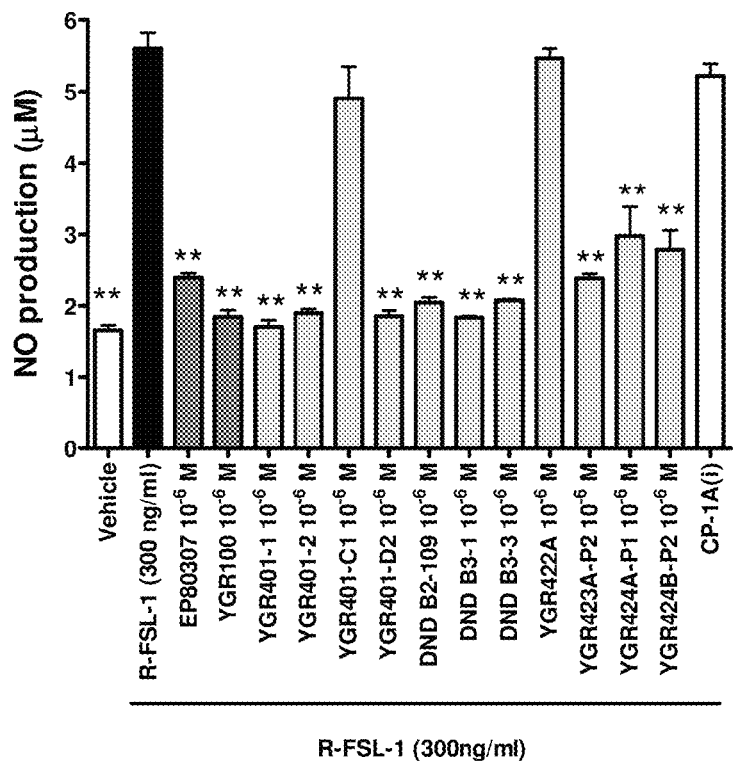
FIG. 9A shows that N-aminoimidazol-2-one derivatives inhibitory effect on nitrite production induced by TLR2 agonist R-FSL-1 in J774 cells. , P<0.01 vs. R-FSL-1 treated cells
Figure 9B:
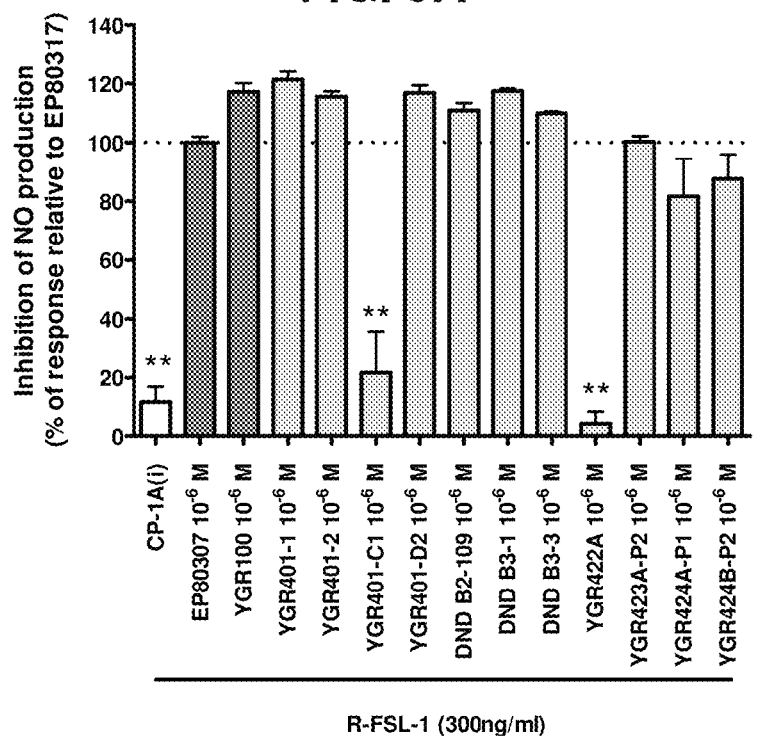
FIG. 9B shows the modulatory effect of N-aminoimidazol-2-one derivatives on nitrites production induced by TLR-2 specific agonist R-FSL-1, relative to EP80317. , P<0.01 vs. EP80317 treated cells.

CD36-dependent signal transduction has been shown to be involved in the regulation of inflammatory and apoptotic responses in macrophages and endothelial cells (Moore 2002) Exposure of macrophages to oxidized LDL or oxLDL-derived phospholipid POVPC induced the activation of MAP kinases JNK1/2 phosphorylation leading in foam cell formation (Rahaman 2006) and generating proinflammatory chemokines and cytokines. Pre-treatment of macrophages with imidazolinone as CD36 ligands reversed JNK1/2 activation induced by POVPC, in a dose-dependent manner (FIG. 8), thus down-regulating pro-inflammatory pathways responsible of atherosclerotic plaques and the sub-retinal dysfunction (Picard 2010).

JNK Assay

RAW 264.7 murine macrophage cells were seeded at $2 \times 10^6$ cells/well in a 6-well plate and starved in serum-free media overnight at 37° C. Cells were first pre-treated with the N-amino-imidazolin-2one peptide mimic at concentrations ranging from $10^{-9}$ to $10^{-6}$ M for 2 h and then stimulated with 10 μg/mL POVPC (Cayman chemical, Ann Arbor, Mich.) for 30 min at 37° C. Medium was then removed and cell plates were immediately frozen at −80° C. Cells were then scrapped into 100 μl of RIPA (50 mM Tris-HCl pH 7.5, 150 mM NaCl, 1% Triton X™-100, 0.1% SDS, 25 mM NaF) containing 1 mM PMSF and 1 mM $Na_3VO_4$, and incubated on ice for 30 min. The soluble fractions were isolated by centrifugation at 12,000×g for 30 min. The supernatant was collected and proteins were assayed with BCA reagent. Aliquots (30 μg/mL) were analyzed on 10% SDS-PAGE and electrotransferred on nitrocellulose membrane. Membrane was blocked with 5% BSA in TBS-T and incubated overnight with primary antibody against phospho-JNK or total-JNK (1:500) (Cell signalling, Pickering, Canada) in 5% BSA TBS-T. The membranes were then washed 5 times with TBS-T and incubated with secondary HRP-conjugated goat anti-rabbit IgG antibody (1:10,000) in 5% BSA TBS-T for 1 h at room temperature. The reaction was visualized by chemiluminescence using SuperSignal™ West Dura (Thermo scientific, Rockford, Ill.) and signals analyzed with Chemilmager™ 5500 (Alpha Innotech, San Leandro, Calif.). The intensity of each band was measured by densitometry using Image Quant™ software (Molecular Dynamics, Sunnyvale, Calif.) and the phosphorylation state was determined from the intensity ratio of phospho-JNK/total-JNK. To determine $IC_{50}$ of inhibition curves, intensity ratio data were plotted using Prism™ 4 software (GraphPad, La Jolla, Calif.).

Example 4

Effect of N-aminoimidazol-2-one Derivatives on the Inhibition of NO Production Induced by the TLR-2 Agonist R-FSL-1 in J774 Cells It is now well known that Toll-like receptors (TLRs) play a key role in the development of inflammation in stimulating the pro-inflammatory cytokines transcription including TNFα, CXCL8, IL-β as well as NO production (Seneviratne, A N, et al. (2012) *Clin Chim Acta*, 413, 3-14; Paul-Clark et al. (2012) *Pharmacol Ther*, 135, 200-215). Among the activated TLRs, the activation of TLR2 by diacylglycerides has been shown to be CD36-dependent (Triantafilou et al. (2006) *J Biol Chem.* 281(41):31002-11—Epub 2006 Jul. 31) as CD36 acts as co-receptor of heterodimeric TLR2 complex. TLR-2 specific activators such as lipopeptides R-FSL-1 or R-MALP-2 have been reported to stimulate TNFα production in a CD36-dependent manner (Hoebe et al. (2005). *Nature*, 433, 523-527; Jimenez-Dalmaroni et al. (2009) *PLoS One*, 4, e7411; Stewart et al. (2010) *Nat Immunol*, 11, 155-161)

Previous work on EP80317, a prototype of growth hormone-releasing peptides as CD36 ligand, was shown to reduce the inflammatory process with the reduction of the expression of proinflammatory proteins, inducible nitric oxide synthase as well as that of vascular endothelial cell adhesion-1 and CCL2 chemokine (Harb D et al. (2009), *Cardiovasc Res*, 83, 42-51). In investigating the molecular mechanisms involved in the anti-inflammatory effect of EP80317, it was found that this compound acts as indirect antagonist of TLR-2 receptors in reducing the NO production induced by TLR-2 agonist R-FSL-1 in J774 cultured macrophage cell line. This model was used to investigate the activity of imidazolones derivatives described herein.

Experimental Protocol:

J774 cells (ATCC passage 10 to 15) were cultured ($2\times10^5$ cells/ml) in 24-well plates (Costar 3524 NY) in DMEM supplemented with FBS (10%).Three hours after plating, cell culture medium was replaced with 0.5 mL of the same medium containing $10^{-6}$M of imidazolones derivatives for 2 hr pretreatment. Cells were then exposed to R-FSL1 (300 ng/ml) for 17 hr at 37° C. Cell culture media were collected and aliquots (10 µL) were mixed with 10 µL of 2,3 diaminonapthalene reagent (0.05 mg/mL in HCl 0.62M) for nitrite levels determination by fluorescence ($\lambda$exc 365 nm and $\lambda$em 430 nm) (Misko et al. (1993) *Anal Biochem*, 214, 11-16).

N-aminoimidazol-2-one derivatives and other peptidomimetics tested:

CP-1A(i)=His-azaPheAla-Trp-DPhe-Ala-NH$_2$;
EP80317=HAlC-2MeDTrp-DLys-Trp-DPhe-Lys-NH$_2$;
YGR-100=[azaTyr4]-GHRP-6 (His-DTrp-Ala-azaTyr-Lys-DPhe-NH$_2$);
YGR401-2=compound 31a (or R-31) described above;
YGR401-D2=compound 31b described above;
YGR401-1=S-31, the diastereomer of compound 31a described above in which the D-Phe has been replaced by L-Phe at the 5 position;
YGR401-C1=diastereomer of compound 31b described above in which the D-Phe has been replaced by L-Phe at the 5 position;
DND B2-109, DND B3-1, DND B3-3 correspond respectively to compounds DND-B2-109, DND-B3-1 and DND-B3-3 described above; and
YGR422A; YGR423A-P2; YGR424A-P1 and YGR424B-P2 correspond respectively to compounds 422A; 423A; 424A and 424B described above.

Results:

Treatment of J774 cells with R-FSL-1 (300 ng/mL) for 17 hrs induced a 3-fold increase of nitrite production as compared to basal conditions. Pre-exposure (2 hr) to the CD36 ligand EP80317 (positive control at $10^{-6}$ M) or to imidazolones analogs ($10^{-6}$M) negatively modulated nitrite production induced by R-FSL-1. The efficacy of N-aminoimidazol-2-one derivatives on the inhibition of NO production, (YGR401-1, YGR 401-2, DNDB3-01, DNDB3-03, DND B2-109) was found comparable to that of EP80317. Azapeptide analogue CP-1A(i) did not modulate NO production elicited by R-FSL1, and was used as negative control.

The scope of the claims should not be limited by the preferred embodiments set forth in the examples, but should be given the broadest interpretation consistent with the description as a whole. In the claims, the word "comprising" is used as an open-ended term, substantially equivalent to the phrase "including, but not limited to". The singular forms "a", "an" and "the" include corresponding plural references unless the context clearly dictates otherwise.

REFERENCES i (a) Kemp, D. S.; Bowen, B. R.; Muendel, C. C. *J. Org. Chem.* 1990, 55(15), 4650-4657. (b) Smith, A. B. Ill.; Keenan, T. P.; Holcomb, R. C.; Sprengeler, P. A.; Guzman, M. C.; Wood, J. L.; Carroll, P. J.; Hirshmann, R. *J. Am. Chem. Soc.* 1992, 114, 10672-10674. (c) Damewood, J. R. Jr.; Edwards, P. D.; Feeney, S.; Gomes, B. C.; Steelman, P. A. T.; Williams, J. C.; Warner, P.; Woolson, S. A.; Wolanin, D. J.; Veale, C. A. *J. Med. Chem.* 1994, 37, 3303-3312. (d) Veale, C. A.; Bernstein, P. R.; Bryant, C.; Ceccarelli, C.; Damewood, J. R. Jr.; Earley, R.; Feeney, S. W.; Gomes, B.; Kosmider, B. J.; Steelman, G. B.; Thomas, R. M.; Vacek, E. P.; Williams, J. C.; Wolanin, D. J.; Woolson, S. *J. Med. Chem.* 1995, 38, 98-108. (e) Nowick, J. S. *Acc. Chem. Res.* 2008, 41, 1319-1330. (f) Phillips, S. T.; Rezac, M.; Abel, U.; Kossenjans, M.; Bartlett, P. A. *J. Am. Chem. Soc.* 2002, 124(1), 58-66. (g) Austin, R. E.; Maplestone, R. A.; Sefler, A. M.; Liu, K.; Hruzewicz, W. N.; Liu, C. W.; Cho, H. S.; Wemmer, D. E.; Bartlett, P. A. *J. Am. Chem. Soc.* 1997, 119, 6461-6472. (h) Kemp, D. S.; Allen, T. J.; Oslick, S. L.; Boyd, J. G. *J. Am. Chem. Soc.* 1996, 118, 4240-4248.

ii (a) Freidinger, R. M., Veber, D. F.; Perlow, D. S.; Brooks, J. R.; Saperstein, R. *Science*. 1980, 210, 656. (b) Freidinger, R. M.; Perlow, D. S.; Veber, D. F. *J. Org. Chem.* 1982, 47, 104. (c) Freidinger, R. M. *J. Org. Chem.* 1985, 50, 3631. (d) Jamieson, A. G.; Boutard, N.; Beauregard, K.; Bodas, M. S.; Ong, H.; Quiniou, C.; Chemtob, S.; Lubell, W. D. *J. Am. Chem. Soc.* 2009, 131, 7917-7927.

iii Proulx, C.; Sabatino, D.; Hopewell, R.; Spiegel, J.; Garcia Ramos, Y.;. Lubell, W. D. *Future Medicinal Chemistry*. 2011, 3(9), 1139-1164.

iv (a) Congiu, C.; Cocco, M. T.; Onnis, V. *Bioorg. Med. Chem. Lett.* 2008, 18, 989-993. (b) Xue, N.; Yang, X.; Wu, R.; Chen, J.; He, Q.; Yang, B.; Lu, X.; Hu, Y. Bioorg. Med. Chem. 2008, 16, 2550-2557.

v Bronson, J. J.; DenBleyker, F. L.; Falk, P. J.; Mate, R. A.; Ho, H.-T. Pucci, M. J.; Snyder, L. B. *Bioorg. Med. Chem. Lett.* 2003, 13, 873-875.

vi Carling, R. W.; Moore, K. W.; Moyes, C. R.; Jones, E. A.; Bonner, K.; Emms, F.; Marwood, R.; Patel, S.; Patel, S.; Fletcher, A. E.; Beer, M.; Sohal, B.; Pike, A.; Leeson, P. D. *J. Med. Chem.* 1999, 42, 2706-2715.

vii (a) Burgey, C. S.; Stump, C. A.; Nguyen, D. N.; Deng, J. Z.; Quigley, A. G.; Norton, B. R.; Bell, I. M.; Mosser, S. D.; Salvatore, C. A.; Rutledge, R. Z.; Kane, S. A.; Koblan, K. S.; Vacca, J. P.; Graham, S. L.; Williams, T. M. *Bioorg. Med. Chem. Lett.* 2006, 16, 5052-5056. (b) Shaw, A.; Paone, D. V.; Nguyen, D. N.; Stump, C. A.; Burgey, C. S.; Mosser, S. D.; Salvatore, C. A.; Rutledge, R. Z.; Kane, S. A.; Koblan, K. S.; Graham, S. L.; Vacca, J. P.; Williams, T. M. *Bioorg. Med. Chem. Lett.* 2007, 17, 4795-4798.

Viii (a) Smith, R. C.; Reeves, J. C. *Biochem. Pharmacol.* 1987, 36, 1457. (b) Watanabe, K.; Morinaka, Y.; Hayashi, Y.; Shinoda, M.; Nishi, H.; Fukushima, N.; Watanabe, T.; Ishibashi, A.; Yuki, S.; Tanaka, M. *Bioorg. Med. Chem. Lett.* 2008, 18, 1478-1483.

Ix (a) Hirao, I.; Kimoto, M.; Harada, Y.; Fujiwara, T.; Sato, A., Yokoyama, S. *Nucleic Acids Res. Suppl.* 2002, 2, 37-38. (b) Hirao, I.; Harada, Y.; Kimoto, M.; Mitsui, T.; Fujiwara, T.; Yokoyama, S. *J. Am. Chem. Soc.* 2004), 13298-13305.

x
- (a) Durant, G. J. *Chem. Soc. Rev.* 1985, 84, 375. (b) Cheng, Y. G.; Hu, Y. Z. *Chinese Chem. Lett.* 2004, 15(11), 1281-1284. (c) Hafner, T.; Kunz, D. *Synthesis.* 2007, 9, 1403-1411.

xi (a) Sabatino, D.; Proulx, C.; Klocek, S.; Bourguet, C. B.; Boeglin, D.; Ong, H.; Lubell, W. D *Org. Lett.* 2009, 11, 3650. (b) Sabatino, D.; Proulx, C.; Pohankova, P.; Ong, H.; Lubell, W. D. Structure-Activity Relationships of GHRP-6 Azapeptide Ligands of the CD36 Scavenger Receptor by Solid-Phase Submonomer Azapeptide Synthesis. *J. Am. Chem. Soc.* 2011, 133, 12493-12506.

xii Proulx, C.; Lubell, W. D. *Org. Lett.* 2010. 12(13), 2916-2919.

xiii Proulx, C.; Lubell, W. D. *J. Org. Chem.* 2010. 75(15), 5385-5387.

Xiv (a) Chiu, S.-K.; Keifer, L.; Timberlake, J. W. *J. Med. Chem.* 1979, 22(6), 746-748. (b) Easton, N. R.; Cassady, D. R.; Dillard, R. D. *J. Org. Chem.* 1964, 29, 1851-1855.

xv Peshkov, V. A.; Pereshivko, O. P.; Sharma, S.; Meganathan, T.; Parmar, V. S.; Ermolat'ev, D. S.; Van der Eycken, E. V. *J. Org. Chem.* 2011, 76, 5867-5872.

xvi (a) Lei, A.; Lu, X. *Org. Lett.* 2000, 2(17), 2699-2702. (b) Fritz, J. A.; Wolfe, J. P. *Tetrahedron.* 2008, 64(29), 6838-6852.

xvii
- (a) Zhang, G.; Luo, Y.; Wang, Y.; Zhang, L. Angew. Chem. Int. Ed. 2011, 50, 1-6. (b) Verniest, G.; Padwa, A. *Org. Lett.* 2008, 10(19), 4379-4382.

xviii Wolf, L. B.; Tjen, K. C. M. F.; ten Brick, H. T.; Blaauw, R. H.; Hiemstra, H.; Schoemaker, H. E.; Rutjes, F. P. J. T. *Adv. Synth. Catal.* 2002, 344, 70-83.

Xix Van Esseveldt, B. C. J.; Vervoort, P. W. H.; van Delft, F. L.; Rutjes, F. P. J. T. *J. Org. Chem.* 2005, 70, 1791-1795.

Xx Bourguet, C. B.; Proulx, C.; Klocek, S.; Sabatino, D.; Lubell, W. D. *J. Pept. Sci.* 2010, 16, 284-296.

xxi (a) André, F.; Boussard, G.; Bayeul, D.; Didierjean, C.; Aubry, A.; Marraud, M. *J. Pept. Res.* 1997, 49(6), 556-562. (b) Andre, F.; Vicherat, A.; Boussard, G.; Aubry, A.; Marraud, M. *J. Pept. Res.* 1997, 50(5), 372-381. (c) Lecoq, A.; Boussard, G.; Marraud, M.; Aubry, A. Biopolymers. 1993, 33(7), 1051-1059. (d) Marraud, M.; Aubry, A. *Pept. Sci.* 1996, 40(1), 45-83. (e) Benatalah, Z.; Aubry, A.; Boussard, G.; Marraud, M. *Int. J. Pept. Protein. Res.* 1991, 38(6), 603-605.

xxii Baures, P. W.; Ojala, W. H.; Gleason, W. B.; Mishra, R. K.; Johnson, R. L. *J. Med. Chem.* 1994, 37(22), 3677-3683.

xxiii St-Cyr, D. J.; Maris, T.; Lubell, W. D. *Heterocycles.* 2010, 82(1), 729-737.

xxiv (a) Zouikri, M.; Vicherat, A.; Aubry, A.; Marraud, M.; Boussard, G. *J. Pept. Res.* 1998, 52, 19-26. (b) Rai, R.; Raghothama, S.; Sridharan, S.; Balaram, P. Biopolymers, Peptide Sci. 2006, 88, 350-361.

xxv The extent of racemization is consistent with that (12-15%) observed during the NaH-promoted cyclization of phenylalaninecontaining methionine-sulfonium dipeptides, to provide α-amino-γ-lactams, in: Freidinger, R. M.; Perlow, D. S.; Veber, D. F. *J. Org. Chem.* 1982, 47 (1), 104-109.

xxvi Momany, F. A.; Bowers, C. Y.; Reynolds, G. A.; Chang, D.; Hong, A.; Newlander, K. *Endocrinology.* 1984, 114(5), 1531-1536.

xxvii Demers, A.; McNicoll, N.; Febbraio, M.; Serva, M.; Ong, H. *Biochem. J.* 2004, 382, 417-424.

xxviii Bolduc, O. R.; Lambert-Lanteigne, P.; Colin, D. Y.; Zhao, S. S.; Proulx, C.; Boeglin, D.; Lubell, W. D.; Pelletier, J. N.; Féthière, J.; Ong, H.; Masson, J.-F. *Analyst.* 2011, 136, 3142-3148.

J. B. Ball, P. F. Alewood. *J. Mol. Recogn.* 1990, 3, 55-64.

A. Giannis, T. Kolter. *Angew. Chem.* 1993, 105, 1303-1326; *Angew. Chem., Int. Ed.* 1993, 32, 1244-1267.

M. S. Wolfe, D. Dutta, J. Aubé. *J. Org. Chem.* 1997, 62, 654-663.

L. Ronga, A. G. Jamieson, K. Beauregard, C. Quiniou, S. Chemtob, W. D. Lubell. *Biopolymers.* 2010, 94, 183-191.

N. Boutard, S. Turcotte, K. Beauregard, C. Quiniou, S. Chemtob, W. D. Lubell. *J. Peptide Sci.* 2011, 17, 288-296.

W. A. Loughlin, J. D. A. Tyndall, M. P. Glenn, D. P. Fairlie. *Chem. Rev.* 2004, 104, 6085-6117.

H. Lee, J. Song, Y. Choi, H. Park, K. Lee. *J. Am. Chem. Soc.* 2002, 124, 11881-11893.

R. M. Freidinger, D. S. Perlow, D. F. Veber. *J. Org. Chem.* 1982, 47, 104-109.

C. Y. Bowers, A. O, Sartor, G. A. Reynolds, T. M. Badger. *Endocrinology.* 1991, 128, 2027-2035.

C. Quiniou et al. *J. Immunol.* 2008, 180, 6977-6987.

D. Sabatino, C. Proulx, S. Klocek, C. B. Bourguet, D. Boeglin, H. Ong, W. D. Lubell. *Org. Lett.* 2009, 11, 3650-3653.

b) D. Sabatino, C. Proulx, P. Pohankova, H. Ong, W. D. Lubell. *J. Am. Chem. Soc.* 2011, 133, 12493-12506.

E. Falb, T. Yechezkel, T. Y. Salitra, Y., C. Gilon. *J. Pept. Res.* 1999, 53, 507-517.

M. Crisma, G. D. Fasman, H. Balaram, P. Balaram. *Int. J. Peptide Protein Res.* 1984, 23, 411-419.

Harb et al., *Cardiovasc Res.* 2009 Jul. 1; 83(1):42-51. Epub 2009 Mar. 5.

Okamura et al., *J Am Soc Nephrol.* 2009 March; 20(3):495-505. Epub 2009 Feb. 11.

Picard et al., Aging (Albany N.Y.). 2010 December; 2(12): 981-989. Published online 2010 Nov. 9.

Jimenez B, O. V. Volpert, S. E. Crawford, M. Febbraio, R. L. Silverstein, & N. Bouck: Signals leading to apoptosis dependent inhibition of neovascularization by thrombospondin-1. *Nat Med* 6, 41-48 (2000)

Jimenez B, O. V. Volpert, F. Reiher, L. Chang, A. Munoz, M. Karin, & N Bouck: c-Jun N-terminal kinase activation is required for the inhibition of neovascularization by thrombospondin-1. *Oncogene* 7, 3443-3448 (2001)

Wiltulski, B.; Buschmann, N.; Bergsträber, U. *Tetrahedron* 2000, 56, 8473.

Cliff, M. D.; Pyne, S. G. *Synthesis* 1994, 681.

Armarego, W. L. F.; Perrin, D. D.; *Purification of Laboratory Chemicals*, Butterworth-Heinemann, 1996, p. 381.

Jamieson, A. G.; Boutard, N.; Beauregard, K.; Bodas, M. S.; Ong, H.; Quiniou, C.; Chemtob, S.; Lubell, W. D. Positional Scanning for Peptide Secondary Structure by Systematic Solid-Phase Synthesis of Amino Lactam Peptides. *J. Am. Chem. Soc.* 2009, 131, 7917-7927.

Boutard, N.; Jamieson, A. G.; Ong, H.; Lubell, W. D. Structure-activity analysis of the growth hormone secretagogue GHRP-6 by alpha- and beta-amino gamma-lactam positional scanning. *Chem. Biol. Drug. Des.* 2010, 75, 40-50

The invention claimed is:

1. A peptidomimetic of the sequence A:

$$Z^1\text{-Xaa}^1\text{-Xaa}^2\text{-Xaa}^3\text{-Xaa}^4\text{-Xaa}^5\text{-Xaa}^6\text{-Z}^2 \qquad (A);$$

wherein

Xaa$^1$ is D-His, L-His, D-Ala, L-Ala or an N-amino cyclic urea residue;

Xaa$^2$ is D-Trp, L-Trp, a Trp analog, or an N-amino cyclic urea residue;

Xaa³ is D-Ala, L-Ala, D-Pro, L-Pro, D-Lys, L-Lys, or an N-amino cyclic urea residue;

Xaa⁴ is D-Trp, L-Trp, a Trp analog, or an N-amino cyclic urea residue;

Xaa⁵ is D-Phe, L-Phe or an N-amino cyclic urea residue;

Xaa⁶ is D-Lys, L-Lys or an N-amino cyclic urea residue;

$Z^1$ is H or an amino-terminal modifying group; and $Z^2$ is a carboxyl group or a carboxy-terminal modifying group;

and wherein at least one of Xaa¹ to Xaa⁶ is an N-amino cyclic urea residue, or a pharmaceutically acceptable salt thereof.

2. The peptidomimetic or pharmaceutically acceptable salt thereof of claim 1, wherein said N-amino cyclic urea residue is of any one of formulas I to IX:

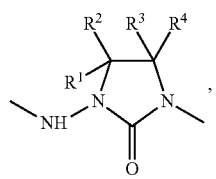
(I)

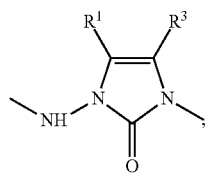
(II)

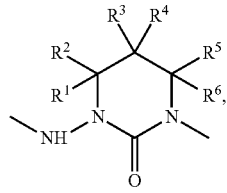
(III)

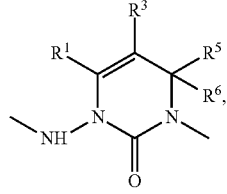
(IV)

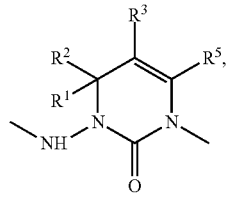
(V)

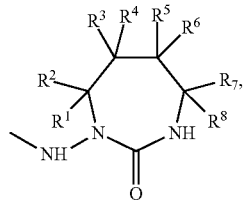
(VI)

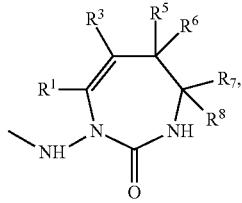
(VII)

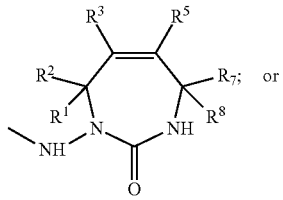
(VIII)

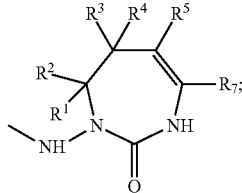
(IX)

wherein $R^1$, $R^2$, $R^3$, $R^4$, $R^5$, $R^6$, $R^7$ and $R^8$ are each independently R, halogen, —OR, —SR, —N(R)₂, —CN, —NO₂, —C(O)R, —CO₂R, —C(O)N(R)₂, —C(O)C(O)R, —C(O)CH₂C(O)R, —S(O)R, —SO₂R, —SO₂N(R)₂, —NRC(O)R, —NRC(O)N(R)₂, —NRSO₂R, —NRSO₂N(R)₂, —N(R)N(R)₂, —C=NN(R)₂, —C=NOR, —OC(O)R, or —OC(O)N(R)₂; wherein R is independently hydrogen or an optionally substituted group selected from $C_{1-6}$ aliphatic; phenyl; a 3- to 7-membered saturated or partially unsaturated carbocyclic ring; a 5- to 6-membered monocyclic heteroaryl ring having 1-3 heteroatoms independently selected from nitrogen, oxygen, and sulfur; or a 4- to 7-membered saturated or partially unsaturated heterocyclic ring having 1-3 heteroatoms independently selected from nitrogen, oxygen, and sulfur, or wherein two adjacent Rx groups and the carbon atom to which they are bound forms a C=O, C=S or C=NR group.

3. The peptidomimetic or pharmaceutically acceptable salt thereof of claim 2, wherein $R^1$, $R^2$, $R^3$, $R^4$, $R^5$, $R^6$, $R^7$ and $R^8$ are each independently H, an alkyl or an arylalkyl, substituted or unsubstituted; saturated or unsaturated; branched or unbranched.

4. The peptidomimetic or pharmaceutically acceptable salt thereof of claim 3, wherein said alkyl is a $C_1$ to $C_6$ alkyl.

5. The peptidomimetic or pharmaceutically acceptable salt thereof of claim 4, wherein said alkyl is a methyl.

6. The peptidomimetic or pharmaceutically acceptable salt thereof of claim 3, wherein said arylalkyl is CH₂-Ph.

7. The peptidomimetic or pharmaceutically acceptable salt thereof of claim 2, wherein the N-amino cyclic urea residue is of formula I.

8. The peptidomimetic or pharmaceutically acceptable salt thereof of claim 7, wherein $R^1$, $R^2$, $R^3$ and $R^4$ are H.

9. The peptidomimetic or pharmaceutically acceptable salt thereof of claim 7, wherein $R^1$, $R^2$ and $R^3$ are H and $R^4$ are is a $C_1$ to $C_6$ alkyl or an arylalkyl.

10. The peptidomimetic or pharmaceutically acceptable salt thereof of claim 2, wherein the N-amino cyclic urea residue is of formula II.

11. The peptidomimetic or pharmaceutically acceptable salt thereof of claim 10, wherein $R^1$ and $R^3$ are H.

12. The peptidomimetic or pharmaceutically acceptable salt thereof of claim 10, wherein $R^1$ is H and $R^3$ is a $C_1$ to $C_6$ alkyl or an arylalkyl.

13. The peptidomimetic or pharmaceutically acceptable salt thereof of claim 2, wherein the N-amino cyclic urea residue is of formula III.

14. The peptidomimetic or pharmaceutically acceptable salt thereof of claim 13, wherein $R^1, R^2, R^3, R^4, R^5$ and $R^6$ are H.

15. The peptidomimetic or pharmaceutically acceptable salt thereof of claim 2, wherein the N-amino cyclic urea residue is of formula VIII.

16. The peptidomimetic or pharmaceutically acceptable salt thereof of claim 15, wherein $R^1, R^2, R^3, R^5, R^7$ and $R^8$ are H.

17. The peptidomimetic or pharmaceutically acceptable salt thereof of claim 1, wherein $Xaa^1$ is His, $Xaa^2$ is D-Trp, $Xaa^3$ is Ala, $Xaa^5$ is D-Phe and $Xaa^6$ is Lys.

18. The peptidomimetic of claim 1, wherein $Z^2$ is $NH_2$.

19. The peptidomimetic or pharmaceutically acceptable salt thereof of claim 1, wherein said peptidomimetic is a compound having one of the following formulas: His-D-Trp-Ala-(N-amino-4-methyl-5-phenyl-imidazol-2-one)-L-Phe-Lys-NH$_2$, His-D-Trp-Ala-(N-amino-4-methyl-5-phenyl-imidazolin-2-one)-DL-Phe-Lys-NH$_2$, His-D-Trp-Ala-(N-amino-4-methyl-5-p-toluyl-imidazol-2-one)-DL-Phe-Lys-NH$_2$, His-D-Trp-Ala-(N-amino-4-methyl-5-m-trifluoromethylphenyl-imidazol-2-one)-DL-Phe-Lys-NH$_2$, His-D-Trp-Ala-(N-amino-4-methyl-5-p-nitrophenyl-imidazol-2-one)-DL-Phe-Lys-NH$_2$, His-D-Trp-Ala-(N-amino-imidazolidin-2-one)-D-Phe-Lys-NH$_2$, His-D-Trp-Ala-(N-amino-4-methyl-imidazolin-2-one)-D-Phe-Lys-NH$_2$, His-D-Trp-Ala-(N-amino-4-benzyl-imidazolin-2-one)-D-Phe-Lys-NH$_2$, His-D-Trp-Lys-(N-amino-4-methyl-imidazol-2-one)-D-Phe-Lys-NH$_2$, Ala-D-Trp-Lys-(N-amino-4-methyl-imidazolin-2-one)-D-Phe-Lys-NH$_2$, His-D-Trp-D-Lys-(N-amino-4-methyl-imidazolin-2-one)-D-Phe-Lys-NH$_2$, Ala-D-Trp-D-Lys-(N-amino-4-methyl-imidazolin-2-one)-D-Phe-Lys-NH$_2$, His-D-Trp-Pro-(N-amino-4-methyl-imidazolin-2-one)-D-Phe-Lys-NH$_2$, Ala-D-Trp-Pro-(N-amino-4-methyl-imidazolin-2-one)-D-Phe-Lys-NH$_2$, His-D-Trp-D-Pro-(N-amino-4-methyl-imidazolin-2-one)-D-Phe-Lys-NH$_2$, Ala-D-Trp-D-Pro-(N-amino-4-methyl-imidazolin-2-one)-D-Phe-Lys-NH$_2$, or a pharmaceutically acceptable salt thereof.

* * * * *